United States Patent
Lindemann et al.

(10) Patent No.: US 12,358,870 B2
(45) Date of Patent: Jul. 15, 2025

(54) SOLID DISPERSIONS AND PHARMACEUTICAL COMPOSITIONS COMPRISING A SUBSTITUTED INDANE AND METHODS FOR THE PREPARATION AND USE THEREOF

(71) Applicant: Peloton Therapeutics Inc., Kenilworth, NJ (US)

(72) Inventors: Christopher Lindemann, Fort Collins, CO (US); Peter J. Stengel, Longmont, CO (US)

(73) Assignee: Peloton Therapeutics, Inc., Dallas, TX (US)

( * ) Notice: Subject to any disclaimer, the term of this patent is extended or adjusted under 35 U.S.C. 154(b) by 981 days.

(21) Appl. No.: 17/286,581

(22) PCT Filed: Oct. 23, 2019

(86) PCT No.: PCT/US2019/057725
§ 371 (c)(1),
(2) Date: Apr. 19, 2021

(87) PCT Pub. No.: WO2020/092100
PCT Pub. Date: May 7, 2020

(65) Prior Publication Data
US 2021/0387946 A1 Dec. 16, 2021

Related U.S. Application Data

(60) Provisional application No. 62/752,685, filed on Oct. 30, 2018.

(51) Int. Cl.
C07C 317/22 (2006.01)
A61K 9/20 (2006.01)
(Continued)

(52) U.S. Cl.
CPC .......... *C07C 317/22* (2013.01); *A61K 9/2054* (2013.01); *A61K 9/2095* (2013.01); *C07B 2200/13* (2013.01); *C07C 2602/08* (2017.05)

(58) Field of Classification Search
CPC . C07C 317/22; C07C 2602/08; A61K 9/2054; A61K 9/2095; A61K 9/10;
(Continued)

(56) References Cited

U.S. PATENT DOCUMENTS 9,896,418 B2  2/2018  Dixon et al.
9,908,845 B2  3/2018  Dixon et al.
(Continued)

FOREIGN PATENT DOCUMENTS

| WO | 2010068794 A2 | 6/2010 | |
|---|---|---|---|
| WO | 2014043208 A1 | 3/2014 | |
| WO | WO-2016145045 A1 * | 9/2016 | ............ A61K 31/18 |

OTHER PUBLICATIONS

Translation of Search Report and Office Action from RU Counterpart of PCT/US2019/057725, dated Nov. 9, 2021, 9 pages.
(Continued)

*Primary Examiner* — Jeffrey H Murray
*Assistant Examiner* — Kevin S Martin
(74) *Attorney, Agent, or Firm* — Eric A. Meade; Emily K. Sauter

(57) ABSTRACT

Provided herein are solid dispersions comprising a HIF-2α inhibitor, pharmaceutical compositions comprising the solid dispersions, and methods for treating HIF-2α-mediated diseases and conditions.

12 Claims, 15 Drawing Sheets

(51) Int. Cl.

| | | |
|---|---|---|
| *A61K 9/10* | (2006.01) | |
| *A61K 9/14* | (2006.01) | |
| *A61K 9/28* | (2006.01) | |
| *A61K 9/48* | (2006.01) | |
| *A61K 31/277* | (2006.01) | |
| *A61K 47/38* | (2006.01) | |
| *A61P 9/12* | (2006.01) | |
| *A61P 35/00* | (2006.01) | |

(58) Field of Classification Search
CPC ...... A61K 9/146; A61K 9/4858; A61K 47/38; A61K 31/277; A61K 9/2077; A61K 9/2009; A61K 9/2013; A61K 9/2018; A61K 9/284; C07B 2200/13; A61P 9/12; A61P 35/00
See application file for complete search history.

(56) References Cited

U.S. PATENT DOCUMENTS

| | | |
|---|---|---|
| 9,969,689 B2 | 5/2018 | Dixon et al. |
| 10,144,711 B2 | 12/2018 | Dixon et al. |
| 10,597,366 B2 | 3/2020 | Dixon et al. |
| RE49,948 E | 4/2024 | Dixon |
| 2009/0143423 A1 | 6/2009 | Schroeder et al. |
| 2014/0100256 A1 | 4/2014 | Lorenz et al. |
| 2015/0182457 A1 | 7/2015 | Huang |
| 2016/0152565 A1 | 6/2016 | Tyavanagimatt et al. |
| 2016/0251307 A1 | 9/2016 | Dixon et al. |
| 2020/0190031 A1 | 6/2020 | Dixon et al. |

OTHER PUBLICATIONS

Shamma, Rehab N. et al., Soluplus®: A novel polymeric solubilizer for optimization of Carvedilol solid dispersions: Formulation design and effect of method of preparation, Powder Technology, 2013, 406-414, 237.

Wehn, Paul M. et al., Design and Activity of Specific Hypoxia-Inducible Factor-2α (HIF-2α) Inhibitors for the Treatment of Clear Cell Renal Cell Carcinoma: Discovery of Clinical Candidate (S)-3-((2,2-Difluoro-1-hydroxy-7-(methylsulfonyl)-2,3-dihydro-1H-inden-, Journal of Medicinal Chemistry, 2018, 9691-9721, 61.

Xu, Rui et al., 3-[(1S,2S,3R)-2,3-Difluoro-1-hydroxy-7-methylsulfonylindan-4-yl]oxy-5-fluorobenzonitrile (PT2977), a Hypoxia-Inducible Factor 2α (HIF-2α) Inhibitor for the Treatment of Clear Cell Renal Cell Carcinoma, Journal of Medicinal Chemistry, 2019, 6876-6893, 62.

Ghosh, Indrajit et al., Comparison of HPMC based polymers performance as carriers for manufacture of solid dispersions using the melt extruder, International Journal of Pharmaceutics, 2011, 12-19, 419(1).

Newman, Ann et al., Assessing the performance of amorphous solid dispersions, J Pharm Sci, 2012, 1355-1377, 101(4).

Wang, Ruyi, et al., Application of Hydroxypropyl Methylcellulose Acetate Succinate to Preparation of Solid Dispersions, Chinese Journal of Pharmaceuticals, 47(1), 2 pages (abstract only), 2016.

\* cited by examiner

1:3 Cmpd:HPMCAS-H

1:3 Cmpd:CAP

1:3 Cmpd:SOLUPLUS

SOLID DISPERSIONS AND PHARMACEUTICAL COMPOSITIONS COMPRISING A SUBSTITUTED INDANE AND METHODS FOR THE PREPARATION AND USE THEREOF

CROSS REFERENCE TO RELATED APPLICATIONS

This application is a U.S. National Phase application under 35 U.S.C. § 371 of PCT Application No. PCT/US2019/057725, filed Oct. 23, 2019, which claims the benefit of U.S. Provisional Application No. 62/752,685, filed Oct. 30, 2018, which is incorporated by reference in the disclosure of this application.

BACKGROUND OF THE INVENTION

An adequate supply of oxygen to tissues is essential in maintaining mammalian cell function and physiology. A deficiency in oxygen supply to tissues is a characteristic of a number of pathophysiologic conditions in which there is insufficient blood flow to provide adequate oxygenation. The hypoxic (low oxygen) environment of tissues activates a signaling cascade that drives the induction or repression of the transcription of a multitude of genes implicated in events such as angiogenesis (neo-vascularization), glucose metabolism, and cell survival/death. A key to this hypoxic transcriptional response lies in the transcription factors, the hypoxia-inducible factors (HIF). HIFs are dysregulated in a vast array of cancers through hypoxia-dependent and independent mechanisms and expression is associated with poor patient prognosis.

HIFs consist of an oxygen-sensitive HIFα subunit and a constitutively expressed HIFβ subunit. When HIFs are activated, the HIFα and HIFβ subunits assemble a functional heterodimer (the a subunit heterodimerizes with the β subunit). Both HIFα and HIFβ have two identical structural characteristics, a basic helix-loop-helix (bHLH) and PAS domains (PAS is an acronym referring to the first proteins, PER, ARNT, SIM, in which this motif was identified). There are three human HIFα subunits (HIF-1α, HIF-2α, and HIF-3α) that are oxygen sensitive. Among the three subunits, HIF-1α is the most ubiquitously expressed and induced by low oxygen concentrations in many cell and tissue types. HIF-2α is highly similar to HIF-1α in both structure and function, but exhibits more restricted cell and tissue-specific expression, and might also be differentially regulated by nuclear translocation. HIF-3α also exhibits conservation with HIF-1α and HIF-2α in the HLH and PAS domains. HIF-1β (also referred to as ARNT-Aryl Hydrocarbon Receptor Nuclear Translocator), the dimerization partner of the HIFα subunits, is constitutively expressed in all cell types and is not regulated by oxygen concentration.

SUMMARY OF THE INVENTION

In certain aspects, the present disclosure provides a solid dispersion comprising a compound of Formula (I):

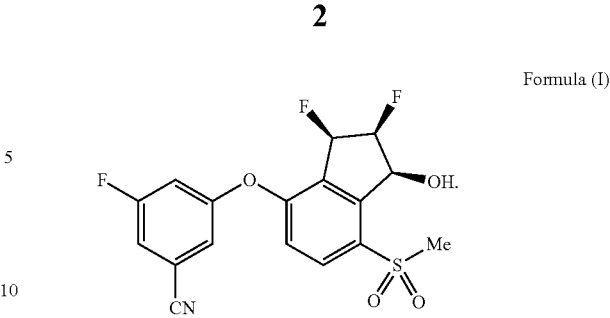

Formula (I)

In some embodiments, the solid dispersion further comprises a pharmaceutically acceptable polymer. The polymer may comprise hydrophobic regions and hydrophilic regions. In some embodiments, the polymer is selected from cellulose esters; cellulose ethers; polyalkylene oxides; polyvinyl chlorides; polyvinyl alcohols; polyacrylates; polymethacrylates; homopolymers and copolymers of N-vinyl lactams, polyacrylamides, and vinyl acetates; graft copolymers of polyethylene glycol, polyvinyl caprolactam, and polyvinyl acetate; oligosaccharides; polysaccharides; and mixtures thereof. In some embodiments, the polymer is a cellulose ester or a cellulose ether. In some embodiments, the polymer is selected from methyl cellulose, ethyl cellulose, hydroxyethyl cellulose, cellulose acetate phthalate (CAP), hypromellose (HPMC), hydroxypropyl cellulose, hypromellose phthalate (HPMCP), hypromellose acetate succinate (HPMCAS), poly(ethylene glycol) methyl, poly-ethylene glycol vinyl acetate vinylcaprolactam (Soluplus), polyethylene glycol 6000 (PEG 6000), polyvinylpyrrolidone (PVP), polyvinylpyrrolidone vinyl acetate (PVP-VA), Poly(ethyl acrylate-co-methyl methacrylate-co-trimethylammonioethyl methacrylate chloride) 1:2:0.1 (e.g., Eudragit RS 100), methyacrylic acid copolymer type B (e.g., Eudragit S 100), methyacrylic acid copolymer type B, polyvinyl acetate phthalate (e.g., Sureteric), polyoxyethylene-polyoxypropylene block copolymer (e.g., Pluronic F-68) and polyoxyethylene (20) sorbitan monooleate (Tween 80). In some embodiments, the polymer is selected from HPMCAS, CAP and poly-ethylene glycol vinyl acetate vinylcaprolactam (e.g., Soluplus). In some embodiments, the polymer is selected from HPMCAS-L, HPMCAS-M and HPMCAS-H, such as HPMCAS-H.

In some embodiments, the compound of Formula (I) is present in an amount from 1% to 50% by weight of the solid dispersion. In some embodiments, the polymer is present in an amount from 50% to 99% by weight of the solid dispersion. In some embodiments, the compound of Formula (I) is present in an amount from 15% to 35% by weight of the solid dispersion. In some embodiments, the polymer is present in an amount from 65% to 85% by weight of the solid dispersion. In some embodiments, the compound of Formula (I) is present in an amount from 22.5% to 27.5% by weight of the solid dispersion. In some embodiments, the polymer is present in an amount from 72.5% to 77.5% by weight of the solid dispersion. In some embodiments, the compound of Formula (I) is present in an amount of about 25% by weight of the solid dispersion. In some embodiments, the polymer is present in an amount of about 75% by weight of the solid dispersion. In some embodiments, the weight ratio of the compound of Formula (I) to the polymer is from 1:99 to 1:1, such as from 15:85 to 35:65. In some embodiments, the weight ratio of the compound of Formula (I) to the polymer is from 22.5:77.5 to 27.5:72.5, such as about 25:75.

In some embodiments, the solid dispersion is substantially non-crystalline. In some embodiments, the solid dispersion is amorphous. In some embodiments, the solid dispersion exhibits a glass transition temperature ($T_g$) between 80 to 100° C., such as between 82 to 92° C. In some embodiments, the solid dispersion exhibits a glass transition temperature ($T_g$) at about 87° C., such as 87±3° C. In some embodiments, the solid dispersion comprises less than 2% of impurities by weight. In some embodiments, the solid dispersion comprises less than 2% of impurities by weight after three months of storage at room temperature. In some embodiments, the solid dispersion comprises less than 2% of water by weight. In some embodiments, the solid dispersion comprises less than 2% of water after three months of storage at room temperature. In some embodiments, the solid dispersion comprises less than 5000 ppm of acetone. In some embodiments, the enantiomeric excess of the compound of Formula (I) is at least 95%, such as at least 99%.

In some embodiments, the particle size distribution of the solid dispersion is characterized by a $d_{10}$ of less than 6 µm. In some embodiments, the particle size distribution of the solid dispersion is characterized by a $d_{50}$ of less than 18 µm. In some embodiments, the particle size distribution of the solid dispersion is characterized by a $d_{90}$ of less than 45 µm. In some embodiments, the solid dispersion is characterized by a bulk density of at least 0.20 g/mL. In some embodiments, the solid dispersion is characterized by a tapped density of at least 0.35 g/mL. In some embodiments, the particle size distribution of the solid dispersion is characterized by a $d_{10}$ of less than 15 µm. In some embodiments, the particle size distribution of the solid dispersion is characterized by a $d_{50}$ of less than 45 µm. In some embodiments, the particle size distribution of the solid dispersion is characterized by a $d_{90}$ of less than 90 µm. In some embodiments, the solid dispersion is characterized by a bulk density of at least 0.15 g/mL. In some embodiments, the solid dispersion is characterized by a tapped density of at least 0.30 g/mL. In some embodiments, the solid dispersion is characterized by a $C_{max}$ GB of at least 300 µgA/mL. In some embodiments, the solid dispersion is characterized by a $C_{max}$ FaSSIF of at least 400 µgA/mL. In some embodiments, the solid dispersion is characterized by an AUC FaSSIF of at least 40,000 µgA/mL. In some embodiments, the solid dispersion is characterized by an AUC FaSSIF of at least 85,000 µgA/mL. In some embodiments, the solid dispersion is obtained by spray drying. In some embodiments, the solid dispersion is obtained by melting, solvent evaporation, spray drying, fusion, kneading, co-grinding, lyophilization, holt melt extrusion, melt agglomeration, or supercritical fluid technology.

In certain aspects, the present disclosure provides an amorphous solid dispersion comprising, by weight relative to the total weight of the solid dispersion:

(a) 22.5% to 27.5% of a compound of Formula (I):

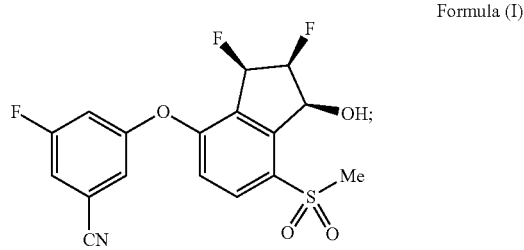 [SMILES: CS(=O)(=O)c1ccc(Oc2cc(F)cc(C#N)c2)c2c1[C@H](O)[C@H](F)[C@@H]2F]

Formula (I)

and (b) 72.5% to 77.5% of HPMCAS.

In certain aspects, the present disclosure provides a pharmaceutical composition comprising a solid dispersion described herein and a pharmaceutically acceptable excipient. In some embodiments, the pharmaceutical composition is a capsule or a tablet. In some embodiments, the pharmaceutical composition is formulated for oral delivery. In some embodiments, the pharmaceutically acceptable excipient comprises a binder, a filler, a disintegrant, a lubricant, a glidant, or a combination thereof. In some embodiments, the solid dispersion is present in an amount from 15% to 50% by weight of the pharmaceutical composition. In some embodiments, the pharmaceutical composition comprises, by weight relative to the total weight of the pharmaceutical composition: (a) 15% to 50% of the solid dispersion; (b) 20% to 50% of a binder; (c) 20% to 40% of a filler; (d) 1.0% to 5.0% of a disintegrant; and (e) 0.25% to 1.25% of a lubricant. In some embodiments, the binder is microcrystalline cellulose. In some embodiments, the filler is mannitol. In some embodiments, the disintegrant is croscarmellose sodium. In some embodiments, the lubricant is magnesium stearate. In some embodiments, the pharmaceutical composition further comprises, by weight relative to the total weight of the pharmaceutical composition, 0.1% to 1.25% of a glidant, optionally wherein the glidant is colloidal silicon dioxide. In some embodiments, the pharmaceutical composition further comprises a coating, optionally wherein the coating is a poly(vinyl) alcohol polymer-based coating. In certain embodiments, the poly(vinyl) alcohol polymer-based coating in the pharmaceutical composition further comprises polyethylene glycol. In specific embodiments, the pharmaceutical composition has a coating which is OpaDry II.

In certain aspects, the present disclosure provides a packaged solid dispersion comprising a solid dispersion described herein and a desiccant. In some embodiments, the desiccant is $SiO_2$. In some embodiments, the packaging comprises a low moisture vapor transmission container.

In certain aspects, the present disclosure provides a method of treating von Hippel-Lindau (VHL) disease, comprising administering to a subject in need thereof an effective amount of a solid dispersion or a pharmaceutical composition described herein. In some embodiments, the subject also suffers from a hemangioblastoma, a pheochromocytoma, a pancreatic neuroendocrine tumor or renal cell carcinoma, such as renal cell carcinoma. The present disclosure also provides a method of treating renal cell carcinoma, comprising administering to a subject in need thereof an effective amount of a solid dispersion or a pharmaceutical composition described herein. In some embodiments, the renal cell carcinoma is clear cell renal cell carcinoma.

In certain aspects, the present disclosure provides a method of treating a HIF-2α-mediated disease or condition, comprising administering to a subject in need thereof a therapeutically effective amount of a solid dispersion or a pharmaceutical composition described herein. In some embodiments, the disease or condition is cancer. In some embodiments, the disease or condition is selected from renal cell carcinoma, von Hippel-Lindau disease, pulmonary arterial hypertension, glioblastoma, and colitis. The present disclosure also provides a method of inhibiting HIF-2α, comprising contacting HIF-2α with an effective amount of a solid dispersion or a pharmaceutical composition described herein. The methods described herein may further comprise administering a second therapeutic agent.

In certain aspects, the present disclosure provides a process for preparing a solid dispersion described herein, comprising: (a) providing a solution of the compound of Formula (I) and the polymer in a solvent; and (b) removing the solvent to provide the solid dispersion. In some embodiments, the solvent comprises acetone, methyl ethyl ketone, tetrahydrofuran, water, or a combination thereof. In some embodiments, the solvent comprises acetone. In some embodiments, the solvent comprises up to 5% water. In some embodiments, the solvent is removed by freeze evaporation or spray drying. In some embodiments, the solvent is removed by spray drying. The process may further comprise drying the solid dispersion in a tray dryer, thereby removing residual solvent. In some embodiments, the solution comprises 8% to 14% solids by weight.

In certain aspects, the present disclosure provides a pharmaceutical solid dosage form for oral delivery of a compound of Formula (I),

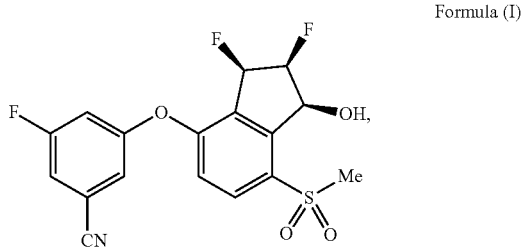 [SMILES: CS(=O)(=O)c1ccc(Oc2cc(F)cc(C#N)c2)c2c1[C@H](O)[C@H](F)[C@@H]2F]

Formula (I)

wherein the solid dosage form comprises (a) a solid dispersion comprising a compound of Formula (I); and (b) one or more pharmaceutically acceptable excipients. In some embodiments, the solid dosage form is a capsule or a tablet. In some embodiments, the solid dosage form is a tablet. In some embodiments, the one or more pharmaceutically acceptable excipients comprise a binder, a filler, a disintegrant and a lubricant. In some embodiments, the solid dispersion is present in an amount from 15% to 50% by weight of the solid dosage form. In some embodiments, the solid dispersion comprises a pharmaceutically acceptable polymer. In some embodiments, the pharmaceutically acceptable polymer is HPMCAS. In some embodiments, the polymer is present in an amount from 15% to 35% by weight of the solid dosage form. In some embodiments, the compound of Formula (I) is present in an amount from 1% to 15% by weight of the solid dosage form. The solid dosage form may comprise 5 mg to 100 mg of the compound of Formula (I), such as about 10 mg of the compound of Formula (I) or about 40 mg of the compound of Formula (I).

A solid dosage form of the present disclosure may comprise a binder in an amount from 20% to 50% by weight of the solid dosage form, optionally wherein the binder is microcrystalline cellulose. The solid dosage form may comprise a filler in an amount from 20% to 40% by weight of the solid dosage form. In some embodiments, the solid dosage form comprises an intragranular filler and an extragranular filler, wherein the intragranular filler is present in an amount from 12% to 22% by weight of the solid dosage form, and wherein the extragranular filler is present in an amount from 8% to 18% of the solid dosage form. In some embodiments, the filler is mannitol. The solid dosage form may comprise a disintegrant in an amount from 1.0% to 5.0% by weight of the solid dosage form. In some embodiments, the solid dosage form comprises an intragranular disintegrant and an extragranular disintegrant, wherein the intragranular disintegrant is present in an amount from 0.9% to 3.0% by weight of the solid dosage form, and wherein the extragranular disintegrant is present in an amount from 0.1% to 2.0% of the solid dosage form. In some embodiments, the disintegrant is croscarmellose sodium. The solid dosage form may comprise a lubricant in an amount from 0.25% to 1.25% by weight of the solid dosage form. In some embodiments, the solid dosage form comprises an intragranular lubricant and an extragranular lubricant, wherein the intragranular lubricant is present in an amount from 0.15% to 0.75% by weight of the solid dosage form, and wherein the extragranular lubricant is present in an amount from 0.10% to 0.50% of the solid dosage form. In some embodiments, the lubricant is magnesium stearate. In some embodiments, the solid dosage form comprises a glidant in an amount from 0.10% to 1.25% by weight of the solid dosage form. In some embodiments, the glidant is colloidal silicon dioxide, such as CabOSil. In some embodiments, the solid dosage form comprises a coating. In some embodiments, the coating is PVA-based, such as OpaDry II.

A solid dosage form of the present disclosure may exhibit a hardness of between 5 and 25 KP. In some embodiments, the weight of the solid dosage form is between 50 and 750 mg, such as about 125 mg or about 500 mg. In some embodiments, the solid dosage form comprises less than 2% of impurities by weight. In some embodiments, the solid dosage form comprises less than 2% of impurities by weight after six months of storage at room temperature. In some embodiments, the solid dosage form comprises less than 3% of water by weight. In some embodiments, the solid dosage form comprises less than 3% of water by weight after six months of storage at room temperature. In some embodiments, the solid dosage form is characterized by a disintegration time between 1 and 5 minutes.

In certain aspects, the present disclosure provides a packaged solid dosage form comprising a solid dosage form described herein and a desiccant. In some embodiments, the desiccant is $SiO_2$. In some embodiments, the packaging comprises a low moisture vapor transmission container. The packaged dosage form may further comprise a cotton, rayon or polyester coil. The present disclosure also provides a kit comprising a solid dosage form described herein and instructions for administering the solid dosage form to a subject in need thereof.

In certain aspects, the present disclosure provides a method of treating von Hippel-Lindau (VHL) disease, comprising administering to a subject in need thereof a solid dosage form described herein. In some embodiments, the subject also suffers from a hemangioblastoma, a pheochromocytoma, a pancreatic neuroendocrine tumor or renal cell carcinoma, such as renal cell carcinoma. The present disclosure also provides a method of treating renal cell carcinoma, comprising administering to a subject in need thereof a solid dosage form described herein. In some embodiments, the renal cell carcinoma is clear cell renal cell carcinoma.

In certain aspects, the present disclosure provides a method of treating a HIF-2α-mediated disease or condition, comprising administering to a subject in need thereof a solid dosage form described herein. In some embodiments, the disease or condition is cancer. In some embodiments, the disease or condition is selected from renal cell carcinoma, von Hippel-Lindau disease, pulmonary arterial hypertension, glioblastoma, and colitis. The present disclosure also provides a method of inhibiting HIF-2α, comprising contacting HIF-2α with a solid dosage form described herein. Any of the subject methods may further comprise administering a second therapeutic agent.

In certain aspects, the present disclosure provides a process for preparing a solid dosage form described herein, comprising: (a) mixing the compound of Formula (I) and the one or more pharmaceutically acceptable excipients to form milled granules; and (b) compressing the granules by applying a compression force of 5 kN to 20 kN. The present disclosure also provides a process for preparing a solid dosage form described herein, comprising: (a) blending a compound of Formula (I), a binder, a filler, a disintegrant and a lubricant, thereby forming a blended mixture; (b) granulating the blended mixture, optionally using a roller compactor, thereby forming a granulated mixture; (c) mixing a second filler, a second disintegrant and a second lubricant with the granulated mixture, thereby forming a tableting mixture; and (d) compressing the tableting mixture into a tablet, wherein the filler and the second filler are the same or different; the disintegrant and the second disintegrant are the same or different; and the lubricant and the second lubricant are the same or different. In some embodiments, the process further comprises mixing a glidant with the granulated mixture of (c). In some embodiments, the process further comprises coating the tablet with a coating, such as OpaDry II.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
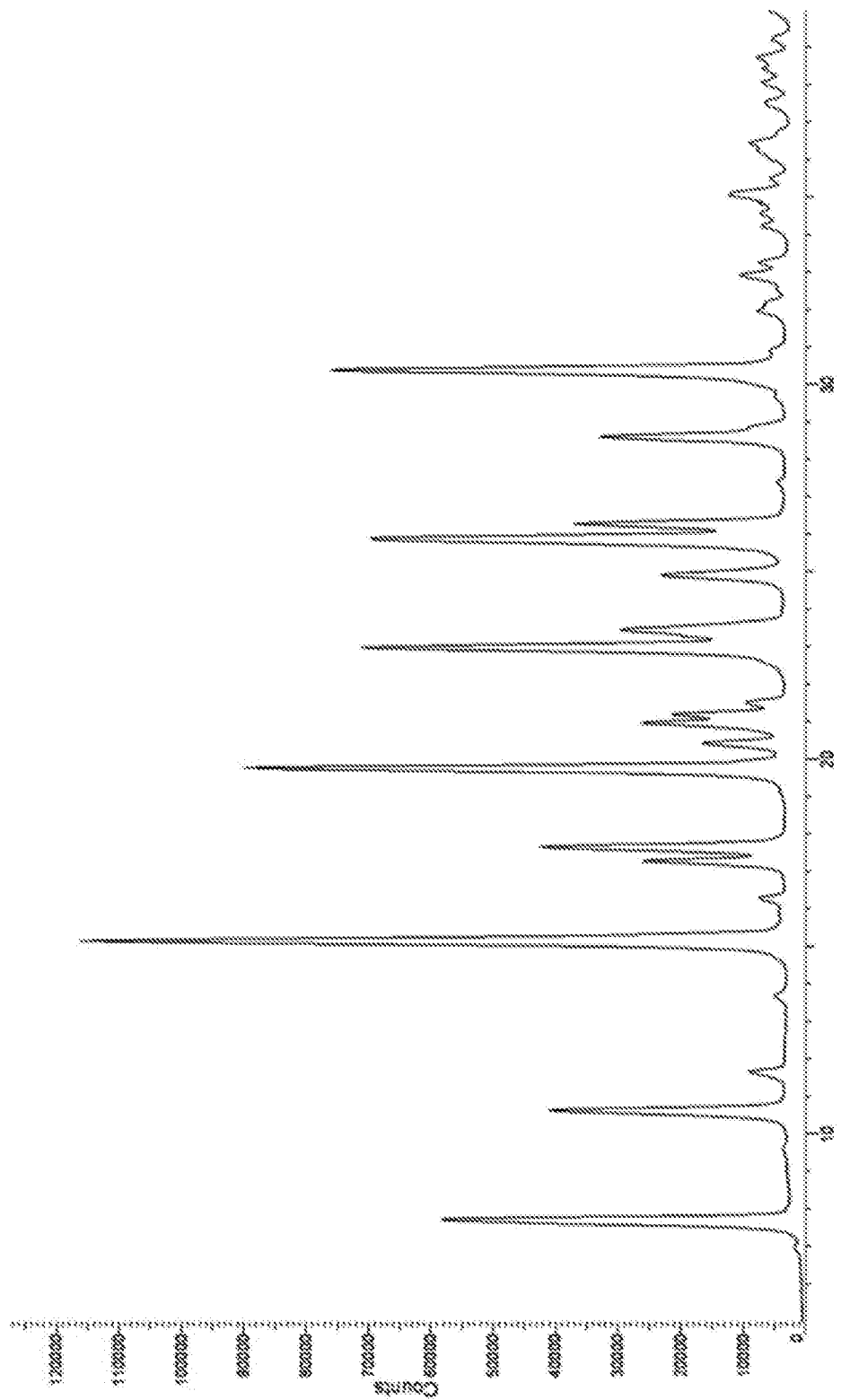
FIG. 1 depicts an XRPD pattern of crystalline compound of Formula (I).

Good manufacturing practices are typically required for large scale manufacture of clinically useful drug candidates. Provided herein are processes for preparing pharmaceutical compositions comprising a compound of Formula (I):

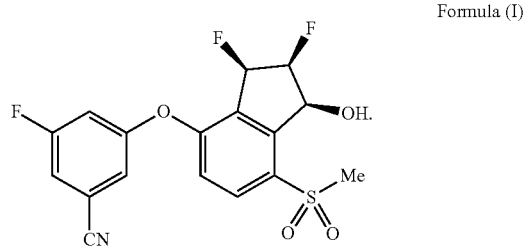 [SMILES: CS(=O)(=O)c1ccc(Oc2cc(F)cc(C#N)c2)c2c1[C@H](O)[C@H](F)[C@@H]2F]

Formula (I)

The compositions provided herein have advantageous physical properties, which may provide benefits in processing, formulation, stability, bioavailability, storage, and handling, among other important pharmaceutical characteristics. The methods described herein allow for large-scale production compliant with good manufacturing practice (GMP) guidelines.

As used herein, and unless otherwise specified, the compound referred to herein by the name 3-(((1S,2S,3R)-2,3-difluoro-1-hydroxy-7-(methylsulfonyl)-2,3-dihydro-1H-inden-4-yl)oxy)-5-fluorobenzonitrile corresponds to a compound of Formula (I), depicted below.

Formula (I)

Unless defined otherwise, all technical and scientific terms used herein have the same meaning as is commonly understood by one of skill in the art to which this invention belongs.

As used in the specification and claims, the singular form "a", "an" and "the" include plural references unless the context clearly dictates otherwise.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

The compound of Formula I also include crystalline and amorphous forms of the compound, pharmaceutically acceptable salts, and active metabolites of these compounds having the same type of activity, including, for example, cocrystals, polymorphs, pseudopolymorphs, solvates, hydrates, unsolvated polymorphs (including anhydrates), conformational polymorphs, and amorphous forms of the compound, as well as mixtures thereof.

The term "cocrystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals), There is no proton transfer between the dissimilar components and the solid phase is neither a simple salt nor a solvate. A discussion of co-crystals can be found, e.g., in S. Aitipamula et al., Crystal Growth and Design. 2012, 12 (5), pp. 2147-2152.

As used herein, the term "solid form" refers to a compound which is not predominantly in a liquid or a gaseous state. As used herein, the term solid form encompasses semi-solids. Solid forms may be crystalline, amorphous, partially crystalline, partially amorphous, or mixtures thereof. A "single-component" solid form comprising a compound of Formula (I) consists essentially of a compound of Formula (I). A "multiple-component" solid form comprising a compound of Formula (I) comprises one or more additional species, such as ions and/or molecules, within the solid form. For example, in particular embodiments, an amorphous multiple-component solid form comprising a compound of Formula (I) comprises one or more polymer(s) and a compound of Formula (I) dispersed in a solid matrix that comprises the polymer(s).

The term "crystalline", when used to describe a substance, compound, component, product, or form, means that the substance, compound, component, product, or form is substantially crystalline, for example, as determined by X-ray diffraction.

The term "crystal form" refers to crystalline modifications comprising a given substance, including single-component crystal forms and multiple-component crystal forms, and including, but not limited to, polymorphs, solvates, hydrates, co-crystals, other molecular complexes, salts, solvates of salts, hydrates of salts, co-crystals of salts, and other molecular complexes of salts, and polymorphs thereof. In some embodiments, a crystal form of a substance may be substantially free of amorphous forms and/or other crystal forms. In other embodiments, a crystal form of a substance may contain less than about 1%, 2%, 3%, 4%, 5%, 10%, 15%, 20%, 25%, 30%, 35%, 40%, 45%, or 50% of one or more amorphous form(s) and/or other crystal form(s) on a weight basis. Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

The terms "polymorph" and "polymorphic form" refer to two or more crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

The terms "amorphous" and "amorphous form" are used herein to describe a substance, component, or product that is not substantially crystalline as determined by X-ray diffraction. In certain embodiments, an amorphous form of a substance may be substantially free of crystal forms. In other embodiments, an amorphous form of a substance may contain less than about 1%, 2%, 3%, 4%, 5%, 10%, 15%, 20%, 25%, 30%, 35%, 40%, 45% or 50% of one or more crystal forms on a weight basis. In other embodiments, an amorphous form of a substance may comprise additional components or ingredients (for example, an additive, a polymer, or an excipient that may serve to further stabilize the amorphous form). In some embodiments, an amorphous form may be a solid solution. Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

Unless otherwise specified, the term "solid dispersion" refers to a solid state which comprises at least two constituents, wherein one constituent is homogenously dispersed significantly evenly throughout the other constituent or constituents. It includes solid or glassy solutions, i.e., the dispersion of the constituents is in such a way that the composition is chemically and physically homogenous in nature. In one embodiment, the first constituent is an active pharmaceutical ingredient (API), such as a compound of Formula (I), and the second constituent is a matrix that comprises a polymer, wherein the API is dispersed significantly uniformly within the matrix (the polymer). The API may be present in an amorphous state or in fine crystalline dispersed form. Also, the API may be available as a mixture of amorphous and crystalline forms. A solid dispersion can comprise more than two constituents. For example, two or more API can be dispersed into the matrix, and the matrix can comprise two or more polymers. Without limitation, solid dispersions may be physically classified as a eutectic mixture, a solid solution, a glass solution or suspension, an amorphous precipitate in a glassy or crystalline carrier, a complex, a complexed formation or a combination of the different systems. In addition, solid dispersions may be prepared using various techniques known to those skilled in the art, such as by co-dissolving the API and polymer in a solvent, then spray-drying, spray-congealing, evaporating, curing or microwaving, blending and direct compression, mechanical admixture at an elevated but non-melting temperature, wet granulation, extrusion-spheronization, melt fusion, hot melt extrusion and the like. A "solid matrix" refers to a matrix that is solid.

The term "polymer" refers to a compound comprising repeating structural units (monomers) connected by covalent chemical bonds. Polymers may be further derivatized, cross-linked, grafted or end-capped. Non-limiting examples of polymers include copolymers, terpolymers, quaternary polymers, and homologues. The term "copolymer" refers to a polymer consisting essentially of two or more different types of repeating structural units (monomers).

The terms "about" and "approximately", when used in connection with an amount, refer to an amount that is within 30%, such as within 20%, within 15%, within 10%, or within 5%, of the specified amount.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or(S)-. The present chemical entities, pharmaceutical compositions and methods are meant to include all such possible stereoisomers, including racemic mixtures, optically pure forms, mixtures of diastereomers and intermediate mixtures. Optically active (R)- and(S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "pharmaceutically acceptable excipient" includes, without limitation, any adjuvant, carrier, excipient, binder, filler, disintegrant, lubricant, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein or enzyme (e.g., HIF-2α). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with inflammation.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "heterodimerization" as used herein refers to the complex formed by the non-covalent binding of HIF-2α to HIF-1β (ARNT). Heterodimerization of HIF-2α to HIF-1β (ARNT) is required for HIF-2α DNA binding and transcriptional activity and is mediated by the HLH and PAS-B domains. Transcriptional activity following heterodimerization of HIF-2α to HIF-1β (ARNT) can affect five groups of target genes including angiogenic factors, glucose transporters and glycolytic enzymes, stem-cell factors, survival factors, and invasion factors.

The term "HIF-2α" refers to a monomeric protein that contains three conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, most commonly endothelial PAS domain-containing protein 1 (EPAS-1) which is encoded by the EPAS1 gene. Alternative names include basic-helix-loop-helix-PAS protein (MOP2). As a member of the bHLH/PAS family of transcription factors, "HIF-2α" forms an active heterodimeric transcription factor complex by binding to the ARNT (also known as HIF-1β) protein through non-covalent interactions.

The term "HIF-2α PAS-B domain cavity" refers to an internal cavity within the PAS-B domain of HIF-2α. The crystal structure of the PAS-B domain can contain a large (approximately 290 Å) cavity in its core. However, the amino acid side chains in the solution structure are dynamic. For example, those side chains can tend to intrude more deeply in the core, and can shrink the cavity to 1 or 2 smaller cavities or can even expand the cavity. The cavity is lined by amino acid residues comprising PHE-244, SER-246, HIS-248, MET-252, PHE-254, ALA-277, PHE-280, TYR-281, MET-289, SER-292, HIS-293, LEU-296, VAL-302, VAL-303, SER-304, TYR-307, MET-309, LEU-319, THR-321, GLN-322, GLY-323, ILE-337, CYS-339, and ASN-341 of HIF-2α PAS-B domain. The numbering system is from the known structures reported in the RCSB Protein Data Bank with PDB code 3H7W. Other numbering systems in the PDB could define the same amino acids, expressed above, that line the cavity.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to the ability of a biologically active agent to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

The term "OpaDry II" refers to an aqueous film coating manufactured by Colorcon with specifications outlined in the table below:

| Ingredients/Compendial Reference | Grade/Dye Strength | E Number | CFR Reference | CI Number |
|---|---|---|---|---|
| POLYVINYL ALCOHOL-PART. HYDROLYZED (USP, FCC, PhEur, JPE) | — | E1203 | — | — |
| TITANIUM DIOXIDE (USP, FCC, PhEur, JP, ChP, GB) | — | E171 | 73.575, 73.1575 | 77891 |
| MACROGOL/PEG (USP, FCC, PhEur, JECFA, JP) | MW 3350, MACROGOL 4000 JP | E1521 | 172.820 | — |
| TALC (USP, FCC, PhEur, JP, JECFA) | — | E553b | 73.1550 | — |
| FD&C BLUE #2/INDIGO CARMINE ALUMINUM LAKE (JECFA, JSFA, JP MO, GB) | 11%-14% | E132 | 82.51, 82.102 | 73015:1 |

The chemical naming protocol and structure diagrams used herein are a modified form of the I.U.P.A.C. nomenclature system, using ChemDraw Professional 15.1 or OpenEye Scientific Software's mol2nam application. For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Solid Dispersions

In certain aspects, the present disclosure provides a solid dispersion comprising a compound of Formula (I):

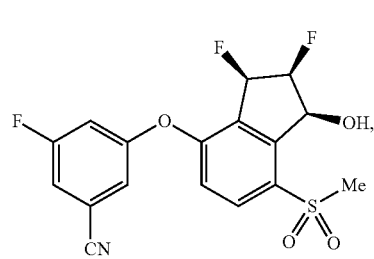

Formula (I)

or a pharmaceutically acceptable salt thereof.

In some embodiments, the solid dispersion further comprises a pharmaceutically acceptable polymer. The compound of Formula (I) may be dispersed in a solid matrix that comprises a polymer. In some embodiments the polymer comprises hydrophobic regions and hydrophilic regions. In some embodiments, the polymer is a water soluble polymer.

Suitable polymers for use in the subject solid dispersions include, but are not limited to cellulose esters; cellulose ethers; polyalkylene oxides; polyacrylates; polymethacrylates; homopolymers and copolymers of N-vinyl lactams, polyacrylamides, vinyl acetate polymers; graft copolymers of polyethylene glycol, polyvinyl caprolactam and polyvinyl acetate; oligosaccharides; polysaccharides; and mixtures thereof.

In some embodiments, the polymer is a cellulose ether polymer. For example, the polymer may be selected from methyl cellulose, ethyl cellulose, (hydroxyalkyl) cellulose (e.g., hydroxyethyl cellulose (HEC) or hydroxypropyl cellulose (HPC)), or (hydroxyalkyl)alkyl-cellulose (e.g., hydroxypropyl methyl cellulose (HPMC or hypromellose)). In some embodiments, the polymer is methyl cellulose. In some embodiments, the polymer is ethyl cellulose. In some embodiments, the polymer is HEC. In some embodiments, the polymer is HPC. In some embodiments, the polymer is HPMC.

In some embodiments, the polymer is a cellulose ester polymer. In some embodiments, the polymer is cellulose phthalate (e.g., cellulose acetate phthalate or hypromellose phthalate (HPMCP)) or cellulose succinate (e.g., hypromellose succinate (HPMCS) or hypromellose acetate succinate (HPMCAS)). In some embodiments, the polymer is HPMCP. In some embodiments, the polymer is HPMCAS.

Cellulose polymers described herein may be further defined by a particular grade. For example, an HPMC polymer may be selected from HPMC E3, HPMC E5, HPMC E6, HPMC E15, HPMC K3, HPMC A4, or HPMC A15. In some embodiments, the HPMCAS is HPMCAS-L, HPMCAS-M, HPMCAS-H, HPMCAS-LF, HPMCAS-MF, HPMCAS-HF, HPMCAS-LG, HPMCAS-MG, or HPMCAS-HG. In some embodiments, the HPMCP is HPMCP 50 or HPMCP 55. In some embodiments, the polymer is HPMCP. In some embodiments, the polymer is HPMCP 50. In some embodiments, the polymer is HPMCAS-L, HPMCAS-M, or HPMCAS-H. In some embodiments, the polymer is HPMCAS-H. In some embodiments, the polymer is HPMCAS-HG.

In some embodiments, the polymer is a polyalkylene oxide. In some embodiments, the polymer is a high molecular weight polyalkylene oxide. In some embodiments, the polymer is polyethylene oxide (PEG or PEO) or copolymers of ethylene oxide and propylene oxide (poloxamers). Suitable PEGs include, without limitation, PEG 400, PEG 600, PEG 1450, PEG 3350, PEG 4000, PEG 6000, PEG 8000, PEG 20000 and mixtures thereof. Suitable poloxamers include, without limitation, poloxamer 124, poloxamer 188, poloxamer 237, poloxamer 338, poloxamer 407 and mixtures thereof. In one embodiment, the polymer is poly (ethylene glycol) methyl. In some embodiments, the polymer is polyethylene glycol 6000 (PEG 6000).

In some embodiments, the polymer is a polyacrylate or polymethacrylate. In some embodiments, the polymer is methacrylic acid/ethyl acrylate copolymer, methacrylic acid/methyl methacrylate copolymer, butyl methacrylate/2-dimethylaminoethyl methacrylate copolymer, poly(hydroxyalkyl acrylates), or poly(hydroxyalkyl methacrylates). Suitable polyacrylate or polymethacrylate include, without limitation, those sold under the Eudragit™ trademark of Rohm GmbH as Eudragit RS 100, Eudragit L 100, Eudragit L 100-55, and Eudragit S 100, products of other manufacturer's equivalent thereto, and mixtures thereof. In one embodiment, the polymer is Eudragit RS 100. In some embodiments, the polymer is Eudragit S 100.

In some embodiments, the polymer is a homopolymer or copolymer of N-vinyl lactams. In some embodiments, the polymer is a homopolymer or copolymer of N-vinyl pyrrolidone. In some embodiments, the polymer is a homopolymer of polyvinylpyrrolidone (PVP or povidone) or a copolymer (e.g., those comprising monomers of N-vinyl pyrrolidone and vinyl acetate (copovidone) or N-vinyl pyrrolidone and vinyl propionate). Suitable povidones include, without limitation, those having a K-value (a measure of viscosity of an aqueous solution of the povidone) of about 12, about 15, about 17, about 25, about 30 or about 90, and mixtures thereof. In some embodiments, the polymer is polyvinylpyrrolidone K30. In some embodiments, the polymer is poly(l-vinylpyrrolidone-co-vinyl acetate).

In some embodiments, the polymer is a polyacrylamide. In some embodiments, the polymer is a vinyl acetate polymer (e.g., copolymers of vinyl acetate and crotonic acid, polyvinyl acetate, polyvinyl alcohol, or partially hydrolyzed polyvinyl acetate). In some embodiments, the polymer is a graft copolymer of polyethylene glycol, polyvinyl caprolactam and polyvinyl acetate (e.g., SOLUPLUS™ of BASF or equivalent product). In some embodiments, the polymer is an oligo- or polysaccharide (e.g., carrageenans, galactomannans, or xanthan gum).

In some embodiments, the polymer is selected from methyl cellulose, ethyl cellulose, hydroxyethyl cellulose, cellulose acetate phthalate (CAP), hypromellose (HPMC), hydroxypropyl cellulose, hypromellose phthalate (HPMCP), hypromellose acetate succinate (HPMCAS), poly(ethylene glycol) methyl, poly-ethylene glycol vinyl acetate vinyl-caprolactam (e.g., SOLUPLUS), polyethylene glycol 6000 (PEG 6000), polyvinylpyrrolidone (PVP), polyvinylpyrrolidone vinyl acetate (PVP-VA), Poly(ethyl acrylate-co-methyl methacrylate-co-trimethylammonioethyl methacrylate chloride) 1:2:0.1 (Eudragit RS 100), methyacrylic acid copolymer type B (Eudragit S 100), Sureteric, Pluronic F-68 and polyoxyethylene (20) sorbitan monooleate (Tween 80). Preferably, the polymer is selected from HPMCAS, CAP and SOLUPLUS, such as HPMCAS. In some embodiments, the polymer is selected from HPMCAS grade L (HPMCAS-L), HPMCAS grade M (HPMCAS-M) and HPMCAS grade H (HPMCAS-H). In some embodiments, the polymer is HPMCAS-H.

In some embodiments, the compound of Formula (I) is present in an amount from 1% to 50% by weight of the solid dispersion, such as from 1% to 45%, from 1% to 40%, from 1% to 35%, from 1% to 30%, from 5% to 50%, from 5% to 45%, from 5% to 40%, from 5% to 35%, from 5% to 30%, from 10% to 50%, from 10% to 45%, from 10% to 40%, from 10% to 35%, from 10% to 30%, from 15% to 50%, from 15% to 45%, from 15% to 40%, from 15% to 35%, from 15% to 30%, from 20% to 50%, from 20% to 45%, from 20% to 40%, from 20% to 35%, from 20% to 30%, from 22.5% to 50%, from 22.5% to 45%, from 22.5% to 40%, from 22.5% to 35%, from 22.5% to 30%, from 22.5% to 27.5%, from 25% to 50%, from 25% to 45%, from 25% to 40%, from 25% to 35%, from 25% to 30%, or from 25% to 27.5% by weight of the solid dispersion. In some embodiments, the compound of Formula (I) is present in an amount of at least 1% by weight of the solid dispersion, such as at least 2%, at least 3%, at least 4%, at least 5%, at least 7.5%, at least 10%, at least 12.5%, at least 15%, at least 17.5%, at least 20%, at least 22.5%, at least 25%, at least 27.5%, at least 30%, at least 32.5%, at least 35%, at least 37.5%, at least 40%, at least 42.5%, at least 45%, at least 47.5%, or at least 50% by weight of the solid dispersion.

In some embodiments, the compound of Formula (I) is present in an amount of about 1%, about 2%, about 3%, about 4%, about 5%, about 7.5%, about 10%, about 12.5%, about 15%, about 17.5%, about 20%, about 22.5%, about 25%, about 27.5%, about 30%, about 35%, about 40%, about 45%, or about 50% by weight of the solid dispersion.

In some embodiments, the compound of Formula (I) is present in an amount from 1% to 50% by weight of the solid dispersion. In some embodiments, the compound of Formula (I) is present in an amount from 15% to 35% by weight of the solid dispersion. In some embodiments, the compound of Formula (I) is present in an amount from at least 22.5% to 27.5% by weight of the solid dispersion. In some embodiments, the compound of Formula (I) is present in an amount of about 25% by weight of the solid dispersion.

In some embodiments, the polymer is present in an amount from 50% to 99% by weight of the solid dispersion, such as from 55% to 99%, from 60% to 99%, from 65% to 99%, from 70% to 99%, from 50% to 95%, from 55% to 95%, from 60% to 95%, from 65% to 95%, from 70% to 95%, from 50% to 90%, from 55% to 90%, from 60% to 90%, from 65% to 90%, from 70% to 90%, from 50% to 85%, from 55% to 85%, from 60% to 85%, from 65% to 85%, from 70% to 85%, from 50% to 80%, from 55% to 80%, from 60% to 80%, from 65% to 80%, from 70% to 80%, from 50% to 77.5%, from 52.5% to 77.5%, from 55% to 77.5%, from 57.5% to 77.5%, from 62.5% to 77.5%, from 65% to 77.5%, from 67.5 to 77.5%, from 70% to 77.5%, from 72.5% to 77.5%, from 50% to 75%, from 52.5% to 75%, from 55% to 75%, from 57.5% to 75%, from 60% to 75%, from 62.5% to 75%, from 65% to 75%, from 67.5 to 75%, from 70% to 75%, or from 72.5% to 75% by weight of the solid dispersion. In some embodiments, the polymer is present in an amount of at least 50% by weight of the solid dispersion, such as at least 55%, at least 57.5%, at least 60%, at least 62.5%, at least 65%, at least 67.5%, at least 70.5%, at least 72.5%, or at least 75% by weight of the solid dispersion.

In some embodiments, the polymer is present in an amount of about 60%, about 62.5%, about 65%, about 67.5%, about 70%, about 72.5%, about 75%, about 77.5%, about 80%, about 82.5%, about 85%, about 87.5%, or about 90% by weight of the solid dispersion.

In some embodiments, the polymer is present in an amount from 50% to 99% by weight of the solid dispersion. In some embodiments, the polymer is present in an amount from 65% to 85% by weight of the solid dispersion. In some embodiments, the polymer is present in an amount from at least 72.5% to 77.5% by weight of the solid dispersion. In some embodiments, the polymer is present in an amount of about 75% by weight of the solid dispersion.

In some embodiments, the weight ratio of the compound of Formula (I) to the polymer is from 1:99 to 1:1, such as from 5:95 to 1:1, from 10:90 to 1:1, from 15:85 to 1:1, from 20:80 to 1:1, from 25:75 to 1:1, from 1:99 to 35:65, from 5:95 to 35:65, from 10:90 to 35:65, from 15:85 to 35:65, from 20:80 to 35:65, from 25:75 to 35:65, from 1:99 to 27.5:72.5, from 5:95 to 27.5:72.5, from 10:90 to 27.5:72.5, from 15:85 to 27.5:72.5, from 20:80 to 27.5:72.5, or from 22.5:77.5 to 27.5:72.5. In some embodiments, the weight ratio of the compound of Formula (I) to the polymer is from 1:99 to 1:1. In some embodiments, the weight ratio of the compound of Formula (I) to the polymer is from 15:85 to 35:65. In some embodiments, the weight ratio of the compound of Formula (I) to the polymer is from 22.5:77.5, to 27.5:72.5. In some embodiments, the weight ratio of the compound of Formula (I) to the polymer is about 25:75.

A solid dispersion disclosed herein may be characterized by X-ray powder diffraction (XRPD), differential scanning calorimetry (DSC), modulated differential scanning calorimetry (mDSC), scanning electron microscopy (SEM), Karl Fischer water titration (KF), residual solvent, particle size, bulk density, tapped density, chiral high pressure liquid chromatography (HPLC) and achiral HPLC.

XRPD may be used to evaluate the crystallinity of the solid dispersion, such as to identify whether the solid dispersion is crystalline, semicrystalline or amorphous. In some embodiments, the solid dispersion is substantially non-crystalline. In some embodiments, no more than about 20%, no more than about 15%, no more than about 10%, no more than about 5%, no more than about 4%, no more than about 3%, no more than about 2%, or no more than about 1% of the solid dispersion is crystalline as observed by X-ray powder diffraction. In some embodiments, the solid dispersion is amorphous. The XRPD pattern of an amorphous solid dispersion is typically characterized by a broad background signal, i.e., a pattern lacking discrete peaks that would be found in a crystalline material. Preferably, XRPD is performed using a Bruker D2 Phaser X-ray diffractometer, with a scan type coupled θ/2θ, wherein the voltage is set to 30 kV and current is set to 10 mA at a rotation of 15 rpm held by a Zero-Background Cup, with slit width at 1.0 mm and knife-edge width set at 1.0 mm.

The glass transition temperature ($T_g$) and melting temperature ($T_m$) of a solid dispersion can be measured using any suitable technique, such as mDSC. In some embodiments, the solid dispersion exhibits a $T_g$ between 70 to 110° C., such as between 75 to 105° C., between 80 to 100° C., between 80 to 95° C., between 82 to 92° C., or between 83 to 89° C. In some embodiments, the solid dispersion exhibits a $T_g$ at about 87° C., such as 87.0±2.0° C. Preferably, the mDSC analysis is conducted on a TA Q2000, RCS 90 instrument at a temperature range of 0 to 250° C. with a heating rate of 1.5° C. per minute, wherein the scanning mode is modulated at a frequency of 60 seconds and an amplitude of 1° C. In some embodiments, the solid dispersion exhibits a $T_g$ between 60 to 145° C., such as between 65 to 140° C., between 70 to 135° C., between 75 to 130° C., between 77.5 to 120° C., between 80 to 110° C., between 82.5 to 100° C., or between 85 to 90° C.

SEM imaging may be used to visually characterize the morphology of the solid dispersion. In some embodiments, the solid dispersion comprises whole and collapsed spheres. The surfaces of the spheres may be smooth. In some embodiments, no crystalline material is detected in an SEM image of the solid dispersion. Preferably, SEM is performed using a FEI Quanta 200 SEM with a Polaron Autocoater E5200 Au/Pd target sputter coater, with a voltage of 15 kV, spot size of 3.0 mA, filament current of 2.52 A, and an emission current of 96 µA.

KF may be used to characterize the water content of the solid dispersion. In some embodiments the solid dispersion comprises less than 2% of water by weight. In some embodiments the solid dispersion comprises less than 2% of water after three months of storage at room temperature. A solid dispersion of the present disclosure may be hygroscopic. In some embodiments, exposure of the solid dispersion to humidity, such as 33%, 50% or 75% humidity, reduces the $T_g$ of the solid dispersion. In some embodiments, the $T_g$ of the solid dispersion decreases by 10% or more when exposed to 33% relative humidity for 24 hours. Not wishing to be bound by any particular theory, the impact of humidity on the glass transition temperature may indicate that molecular mobility is possible at room temperature when the humidity is greater than 33%, which could allow the compound of Formula (I) the ability to nucleate and/or crystallize. Preferably, a solid dispersion of the present disclosure is stored under conditions that maintain relative humidity levels of less than 50%, such as less than 33%. In some embodiments, the solid dispersion is packaged with a desiccant, such as $SiO_2$. In some embodiments, the solid dispersion is packaged in a low moisture vapor transmission container, such as a mylar or LDPE bag, optionally in an HDPE drum. In some embodiments, the solid dispersion is packaged and stored with desiccant in a low moisture vapor transmission container.

Residual solvent levels in a solid dispersion of the present disclosure may be determined using gas chromatography head space (GCHS) analysis. For example, an Agilent 6890A/7694 GC/HS instrument equipped with a 30 m×0.32 mm, 1.8 µm, JW Scientific DB-624 column may be used to analyze a sample using the following method parameters: sample temperature, 105° C.; loop temperature, 110° C.; transfer line temperature, 115° C.; GC cycle time, 45 min; vial equilibrium time, 30 min; injection loop size, 1 mL; vial pressure time, 20 sec; carrier gas pressure, 7 psi; and vial pressure, 15 psi. In some embodiments, the solid dispersion comprises residual solvent. In some embodiments the solid dispersion comprises less than 25000 ppm of acetone. In some embodiments the solid dispersion comprises less than 5000 ppm of acetone.

Laser light scattering may be performed on a powder, such a solid dispersion disclosed herein, to determine the particle size distribution. For example, a Malvern Aero S dry particle size analyzer having a 3 mm hopper height may be used at 0.7 bar pressure with a feed rate of 40% to analyze a sample. Preferably, samples are analyzed over the course of 10 seconds in triplicate. A refractive index of 1.681 and a density of 0.5 g/mL may be used for the analysis with a non-spherical algorithm and a sample obscuration between 0.1 and 15%. In some embodiments, the particle size distribution is reported using average $d_{10}$, $d_{50}$ and $d_{90}$ values, wherein 10% of the particles in the solid dispersion by mass have a diameter less than the $d_{10}$ value, 50% of the particles in the solid dispersion by mass have a diameter less than the $d_{50}$ value, and 90% of the particles in the solid dispersion by mass have a diameter less than the $d_{90}$ value. In some embodiments, the particle size distribution of the solid dispersion is characterized by a $d_{10}$ of less than 16 µm, such as less than 15 µm, less than 14 µm, less than 12 µm, less than 10 µm, less than 8 µm or less than about 6 µm. In some embodiments, the particle size distribution of the solid dispersion is characterized by a $d_{50}$ of less than 50 µm, such as less than 45 µm, less than 40 µm, less than 35 µm, less than 30 µm, less than 28 µm, less than 25 µm, less than 23 µm or less than about 18 µm. In some embodiments, the particle size distribution of the solid dispersion is characterized by a $d_{90}$ of less than 100 µm, such as less than 90 µm, less than 80 µm, less than 70 µm, less than 65 µm, less than 55 µm or less than about 45 µm.

The bulk density of a solid dispersion of the present disclosure may be obtained by measuring the mass and volume of a sample of the solid dispersion. In some embodiments, the solid dispersion is characterized by a bulk density of at least 0.10 g/mL, such as at least 0.15 g/mL, at least 0.20 g/mL, at least 0.25 g/mL, or at least 0.30 g/mL.

The tapped density of a solid dispersion of the present disclosure may be obtained by measuring the mass and volume of a sample of the solid dispersion after mechanically tapping the sample until little or no further volume change is observed. In some embodiments, the solid dispersion is characterized by a tapped density of at least 0.20 g/mL, such as at least 0.25 g/mL, at least 0.30 g/mL, at least 0.35 g/mL, at least 0.40 g/mL, at least 0.45 g/mL, or at least 0.50 g/mL.

The purity of a solid dispersion of the present disclosure may be assessed by high pressure liquid chromatography (HPLC). For example, an Agilent 1220 instrument equipped with a Kinetex, C18, 4.6×100 mm, 2.6 µm column using the following method parameters: mobile phase A, 0.1% formic acid in water; mobile phase B, 0.1% formic acid in acetonitrile; gradient 95% A (0 min), 60% A (6 min), 5% A (12 min), 95% A (15.1 min), with the balance made up with mobile phase B; flow rate, 0.8 mL/min; column temperature, 40° C.; sample temperature, room temperature; injection volume, 5 µL; detection wavelength, 240 nm; and run time, 18.5 min. In some embodiments, the solid dispersion comprises less than 5% of impurities by weight, such as less than 2% impurities by weight. In some embodiments, the solid dispersion comprises less than 2% of impurities by weight after three months of storage at room temperature. In some embodiments, the enantiomeric excess of the compound of Formula (I) is at least 95%. In some embodiments, the enantiomeric excess of the compound of Formula (I) is at least 99%. In some embodiments, the enantiomeric excess of the compound of Formula (I) is at least 99.5%.

The dissolution performance of the solid dispersion can be tested in a non-sink dissolution test by measuring the solubility of the compound of Formula (I) in biorelevant intestinal media (FaSSIF) after 30 minutes of exposure to a low-pH environment (SGF). The maximum concentration of the compound of Formula (I) in SGF ($C_{max}$ GB) and SIF ($C_{max}$ FaSSIF), as well as the area under the curve post gastric transfer (AUC FaSSIF) can be obtained from the dissolution profile.

In some embodiments, the $C_{max}$ GB of the solid dispersion is at least 100 µgA/mL, such as at least 150, at least 200, at least 250, at least 300, at least 350, at least 400, at least 450, at least 500, or at least 550 µgA/mL. Preferably, the $C_{max}$ GB is at least 300 µgA/mL. In some embodiments, the $C_{max}$ GB is between 100 to 600 µgA/mL, such as between 150 to 600, between 200 to 550, between 250 to 500, between 300 to 450, between 350 to 450, between 400 to 450, or between 375 to 425 µgA/mL. Preferably, the $C_{max}$ GB is between 375 to 425 µgA/mL. In some embodiments, the $C_{max}$ GB is about 409 µgA/mL, such as 410±10 µgA/mL.

In some embodiments, the $C_{max}$ FaSSIF of the solid dispersion is at least 50 µgA/mL, such as at least 100, at least 150, at least 200, at least 250, at least 300, at least 350, at least 400, at least 450, at least 500, at least 550, at least 600, at least 650, at least 700, at least 750, or at least 800 µgA/mL. Preferably, the $C_{max}$ FaSSIF is least 300 µgA/mL. In some embodiments, the $C_{max}$ FaSSIF is between 50 to 900 µgA/mL, such as between 150 to 800, between 250 to 700, between 350 to 600, or between 350 to 575 µgA/mL. Preferably, the $C_{max}$ FaSSIF is between 350 to 575 µgA/mL. In some embodiments, the $C_{max}$ FaSSIF is about 545 µgA/mL, such as 545±50 µgA/mL, or about 435 µgA/mL, such as 435±50 µgA/mL.

In some embodiments, the AUC FaSSIF of the solid dispersion is at least 10000 µgA/mL, such as at least 20000, at least 30000, at least 40000, at least 50000, at least 60000, at least 70000, at least 80000, at least 90000, or at least 100000 µgA/mL. Preferably, the AUC FaSSIF is least 40000 µgA/mL. In some embodiments, the AUC FaSSIF is between 10000 to 200000 µgA/mL, such as between 10000 to 175000, between 15000 to 150000, between 20000 to 125000, or between 25000 to 100000 µgA/mL. In some embodiments the AUC FaSSIF is about 90000 µgA/mL, such as 90000±1000 µgA/mL. In some embodiments the AUC FaSSIF is about 65000 µgA/mL, such as 65000±1000 µgA/mL.

In some embodiments, the AUC enhancement of the solid dispersion is at least 3.0, such as least 5.0, at least 10.0, at least 15.0, at least 20.0, at least 25.0, at least 30.0, at least 35.0, or at least 40.0, wherein the AUC enhancement represents the ratio of AUC FaSSIF of the solid dispersion to the AUC FaSSIF of the compound of Formula (I). Preferably, the AUC enhancement is at least 10. In some embodiments the AUC enhancement is between 3.0 to 50.0, such as between 5.0 to 45.0, between 10.0 to 40.0, between 15.0 to 40.0, between 20.0 to 40.0, or between 25.0 to 45.0. In some embodiments the AUC enhancement is about 35.0, such as 35.0±3.0. In some embodiments the AUC enhancement is about 25.0, such as 25.0±3.0.

In some aspects, the present disclosure provides an amorphous solid dispersion comprising, by weight relative to the total weight of the solid dispersion:

(a) 22.5% to 27.5% of a compound of Formula (I):

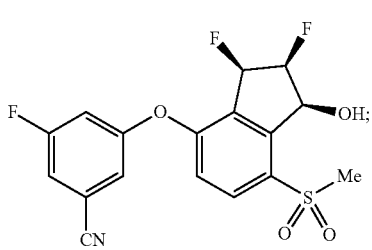

and (b) 72.5% to 77.5% of HPMCAS.

In some aspects, the present disclosure provides an amorphous solid dispersion comprising, by weight relative to the total weight of the solid dispersion:

(a) 20% to 30% of a compound of Formula (I):

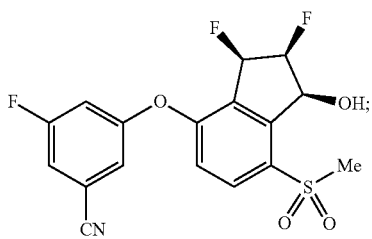

and (b) 70% to 80% of a polymer selected from cellulose esters and cellulose ethers, wherein the solid dispersion exhibits a glass transition temperature ($T_g$) between 80 to 100° C., and wherein the solid dispersion comprises less than 2% of water by weight.

In some aspects, the present disclosure provides an amorphous solid dispersion comprising, by weight relative to the total weight of the solid dispersion:

(a) 1% to 50% of a compound of Formula (I):

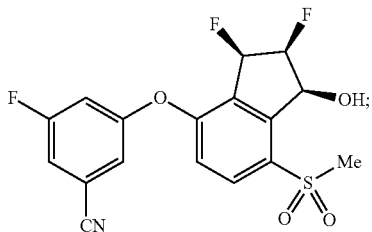

and (b) 50% to 99% of a polymer selected from HPMCAS, CAP and SOLUPLUS.

In some aspects, the present disclosure provides an amorphous solid dispersion comprising, by weight relative to the total weight of the solid dispersion:

(a) 10% to 30% of a compound of Formula (I):

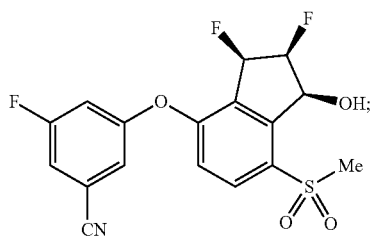

and (b) 70% to 90% of HPMCAS, wherein the solid dispersion comprises less than 2% of water by weight.

In some aspects, the present disclosure provides an amorphous solid dispersion comprising, by weight relative to the total weight of the solid dispersion:

(a) 22.5% to 27.5% of a compound of Formula (I):

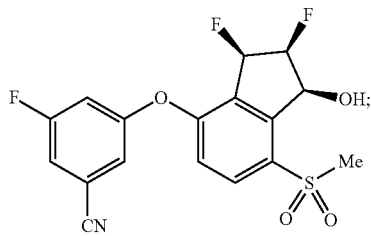

and (b) 72.5% to 77.5% of a polymer selected from HPMCAS-L, HPMCAS-M and HPMCAS-H, wherein the enantiomeric excess of the compound of Formula (I) is at least 95%.

In some embodiments, provided herein is a solid dispersion comprising about 25% by weight of the compound of Formula (I), dispersed in a solid matrix that comprises HPMCAS. In some embodiments, the solid dispersion is provided as a powder. In some embodiments, the solid dispersion is provided as granules. In some embodiments, the solid dispersion is provided as a film. In some embodiments, the solid dispersion remains amorphous after storage at either 25° C. and 60% RH or 40° C. and 75% RH for 4 weeks. In some embodiments, the solid dispersion remains amorphous after storage at either 2-8° C., 25° C. and 60% RH, or 40° C. and 75% RH for 3 months. In some embodiments, the solid dispersion is moderately hygroscopic. In some embodiments, the solid dispersion exhibits an increased solubility of the compound of Formula (I) in an aqueous media as compared to neat compound of Formula (I). In some embodiments, the aqueous media is water, simulated gastric fluid (SGF), simulated intestinal fluid (FaSSIF), or 5% Glycerin solution in water.

Not wishing to be bound by any particular theory, certain solid dispersions provided herein exhibit physical properties, e.g., stability, solubility and/or dissolution rate, appropriate for use in clinical and therapeutic dosage forms. In some embodiments, certain solid dispersions provided herein are appropriate for use in a solid formulation for oral administration.

Crystalline Form

Crystalline forms of the compound of Formula (I) have utility, in the least, in the manufacture of pharmaceutical compositions.

One embodiment provides a crystalline form of the compound of Formula (I):

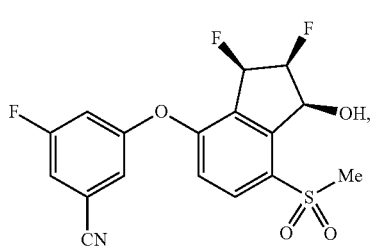

Formula (I)

herein the crystalline form exhibits the XRPD pattern of FIG. 1.

One embodiment provides a crystalline form of the compound of Formula (I):

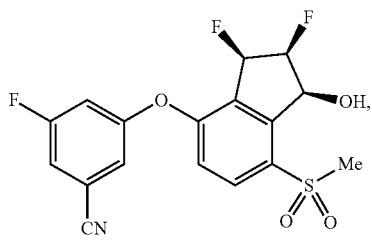

Formula (I)

wherein the crystalline form exhibits a Tm of about 209° C.

One embodiment provides a crystalline form of the compound of Formula (I):

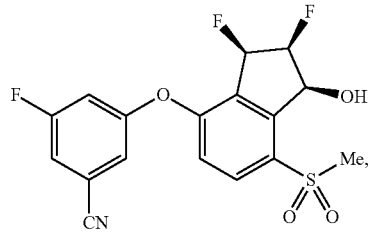

Formula (I)

wherein the crystalline form exhibits a Tg of about 80° C.

One embodiment provides a crystalline form of the compound of Formula (I):

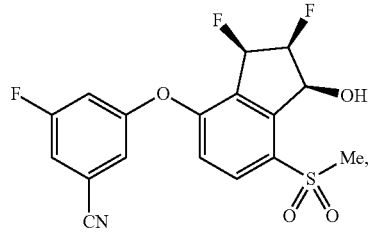

Formula (I)

wherein the crystalline form exhibits a XRPD pattern having at least one 2θ peak selected from 7.6, 15.0, 19.6, 22.9, 25.8, or 30.2.

One embodiment provides a crystalline form of the compound of Formula (I):

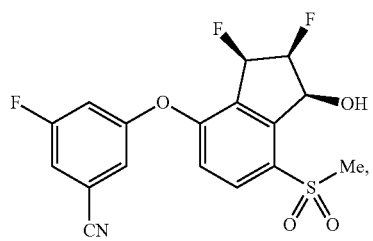

Formula (I)

wherein the crystalline form exhibits a XRPD pattern having at least two 2θ peaks selected from 7.6, 15.0, 19.6, 22.9, 25.8, or 30.2.

One embodiment provides a crystalline form of the compound of Formula (I):

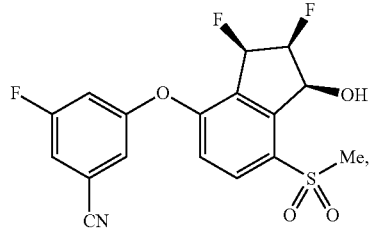

Formula (I)

wherein the crystalline form exhibits a XRPD pattern having at least three 2θ peaks selected from 7.6, 15.0, 19.6, 22.9, 25.8, or 30.2.

One embodiment provides a crystalline form of the compound of Formula (I):

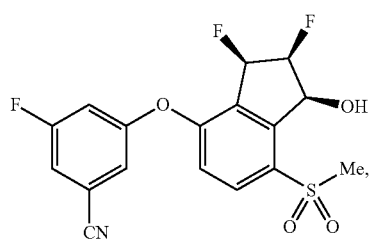

Formula (I)

wherein the crystalline form exhibits a XRPD pattern having at least four 2θ peaks selected from 7.6, 15.0, 19.6, 22.9, 25.8, or 30.2.

One embodiment provides a crystalline form of the compound of Formula (I):

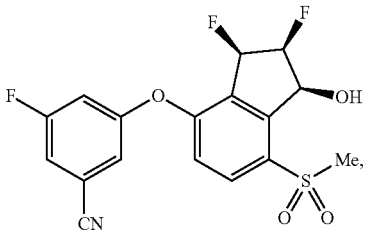

Formula (I)

wherein the crystalline form exhibits a XRPD pattern having at least five 2θ peaks selected from 7.6, 15.0, 19.6, 22.9, 25.8, or 30.2.

Processes for Preparing a Solid Dispersion

In some aspects, the present disclosure provides a process for preparing a solid dispersion disclosed herein, comprising (a) providing a solution of a compound of Formula (I) and a polymer in a solvent; and (b) removing the solvent to provide the solid dispersion. The polymer can be selected from any suitable polymer described herein, such as HPMCAS.

In some embodiments, the solvent comprises acetone, methyl ethyl ketone, tetrahydrofuran, water, or a combination thereof. In some embodiments, the solvent comprises acetone. The solvent may comprise up to 5% water. In some embodiments, the solvent comprises acetone and up to 5% water. In some embodiments, the solvent is 95 to 99% acetone and 1 to 5% water by volume. In some embodiments, the solvent is 90 to 99% acetone and 1 to 10% water by volume.

In some embodiments, the solvent is removed by freeze evaporation or spray drying. In some embodiments, the solid dispersion is obtained by melting, solvent evaporation, spray drying, fusion, kneading, co-grinding, lyophilization, hot melt extrusion, melt agglomeration, or supercritical fluid technology. Preferably, the solvent is removed by spray drying. Solvent removal may further comprise drying the solid dispersion in a tray dryer to remove residual solvent that remains after spray drying.

In some embodiments, the solution comprises 5% to 20% solids by weight, such as 8% to 14% solids by weight. In some embodiments, the solution comprises about 8% solids by weight, such as 8±2% solids.

In some embodiments, the providing of (a) comprises adding a compound of Formula (I) to the solvent (e.g., acetone) and mixing the resultant mixture until the compound of Formula (I) is fully dissolved, or until a clear solution is obtained. The providing of (a) may further comprise adding a suitable polymer (e.g., HPMCAS-H) to the solution of the compound of Formula (I) in acetone, followed by mixing. The removing of (b) comprises spray drying the solution of the compound of Formula (I) and the polymer in the solvent. Spray drying can be completed in any suitable dryer, such as an SPX Anhydro MicraSpray MS-150 spray drying unit equipped with a 2-fluid nozzle. In some embodiments, the spraying is completed in a closed loop configuration. The atomization pressure of the spray drying can be between 2.0 to 3.5 bar, such as 2.5 to 2.8 bar. In some embodiments, the spray rate is 5.0 to 20.0 kg/hr, such as 7.5 to 12.5 kg/hr. In some embodiments, the inlet temperature is elevated, such as between 65 to 85° C. The outlet temperature may also be elevated, such as between 40 to 45° C. In some embodiments, the drying gas flow rate is between 150 to 200 kg/hr. The condenser temperature of the spray drying unit is typically below freezing, such as between −30 to −10° C.

Secondary drying is optionally used to remove residual solvent remaining after spray drying. Secondary drying may comprise tray drying, such as in a Despatch tray dryer. In some embodiments, the solid dispersion is loaded into the trays of the tray dryer to a depth of approximately 1 inch. The temperature of the dryer is typically elevated, such as from 30 to 50° C. In some embodiments, secondary drying has a duration of 1 to 24 hours, such as 6 to 18 hours, 8 to 12 hours, or about 10 hours.

Secondary recovery is optionally used to recover residual solid dispersion from the spray nozzle, main chamber, and outlet after spray drying. In some embodiments, residual solid dispersion from the spray nozzle, main chamber, and/or outlet may be collected and added to the bulk material. Addition of residual solid dispersion collected from one or more of the spray nozzle, the main chamber and the outlet of the spray dryer to the bulk material may increase the overall yield of the solid dispersion by at least 10%, such as at least 15%, at least 20%, at least 25%, at least 30%, at least 35%, or at least 40%.

In some aspects, the present disclosure provides a process for preparing a solid dispersion disclosed herein, comprising (a) providing a solution of a compound of Formula (I) and HPMCAS in a solvent, wherein the solution comprises 6% to 15% total solids by weight; and (b) removing the solvent to provide the solid dispersion. The polymer can be selected from any suitable polymer described herein, such as HPMCAS.

Pharmaceutical Compositions

In some aspects, the present disclosure provides a pharmaceutical solid dosage form for oral delivery of a compound of Formula (I),

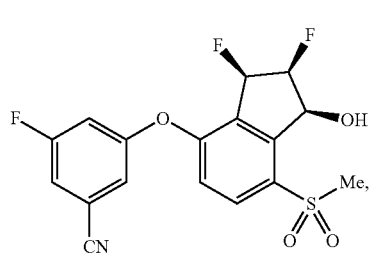

Formula (I)

wherein the solid dosage form comprises: (a) a solid dispersion comprising a compound of Formula (I); and (b) one or more pharmaceutically acceptable excipients.

The solid dosage form may be a capsule or a tablet. In some embodiments, the solid dosage form is a tablet. In some embodiments, the one or more pharmaceutically acceptable excipients comprise a binder, a filler, a disintegrant and a lubricant. In some embodiments, the one or more pharmaceutically acceptable excipients further comprise a glidant and a coating. In some embodiments, the one or more pharmaceutically acceptable excipients comprise a binder, a filler, a disintegrant, a lubricant, a glidant and a coating. In some embodiments, the solid dispersion is present in an amount from 15% to 50% by weight of the solid dosage form.

In some embodiments, the solid dispersion comprises a pharmaceutically acceptable polymer, such as HPMCAS. In some embodiments, the polymer is present in an amount of 15% to 35% by weight of the solid dosage form. In some embodiments, the compound of Formula (I) is present in an amount from 1% to 15% by weight of the solid dosage form. In some embodiments, the solid dosage form comprises 5 mg to 100 mg the compound of Formula (I), such as 10 mg or 40 mg of the compound of Formula (I).

In some embodiments, the solid dosage form comprises a binder in an amount from 20% to 50% by weight of the solid dosage form. The binder may be microcrystalline cellulose. In some embodiments, the solid dosage form comprises a filler in an amount from 20% to 40% by weight of the solid dosage form. The filler may be mannitol. In some embodiments, the solid dosage form comprises an intragranular filler and an extragranular filler, optionally wherein the intragranular filler is present in an amount from 12% to 22% by weight of the solid dosage form and the extragranular filler is present in an amount from 8% to 18% by weight of the solid dosage form.

In some embodiments, the solid dosage form comprises a disintegrant in an amount from 1.0% to 5.0% by weight of the solid dosage form. The solid dosage may comprise an intragranular disintegrant and an extragranular disintegrant, optionally wherein the intragranular disintegrant is present in an amount from 0.9% to 3.0% by weight of the solid dosage form and the extragranular disintegrant is present in an amount from 0.1% to 2.0% by weight of the solid dosage form. In some embodiments, the disintegrant is croscarmellose sodium.

In some embodiments, the solid dosage form comprises a lubricant in an amount from 0.25% to 1.25% by weight of the solid dosage form. The solid dosage form may comprise an intragranular lubricant and an extragranular lubricant, optionally wherein the intragranular lubricant is present in an amount from 0.15% to 0.75% by weight of the solid dosage form and the extragranular lubricant is present in an amount from 0.10% to 0.50% by weight of the solid dosage form. In some embodiments, the lubricant is magnesium stearate.

In some embodiments, the solid dosage form comprises a glidant in an amount from 0.1% to 1.25% by weight of the solid dosage form. The solid dosage form may comprise an intragranular glidant and an extragranular glidant, optionally wherein the intragranular glidant is present in an amount from 0.05% to 0.75% by weight of the solid dosage form and the extragranular glidant is present in an amount from 0.05% to 0.50% by weight of the solid dosage form. In some embodiments, the solid dosage form comprises an extragranular glidant in an amount from 0.2% to 0.5% by weight of the solid dosage form. In some embodiments, the glidant is colloidal silicon dioxide, such as Cab-O-Sil.

In some embodiments, the solid dosage form comprises a coating. In some embodiments, the coating is PVA-based, such as OpaDry II. In some embodiments, the coating is pigmented, optionally wherein the coating is blue. The solid dosage form may comprise a coating in an amount from 1% to 5% by weight of the solid dosage form, such as about 3% by weight.

In some embodiments, the hardness of the solid dosage form is between 5 and 25 KP. The weight of the solid dosage form may be between 50 and 750 mg, such as about 125 mg or about 500 mg. In some embodiments, the solid dosage form comprises less than 2% of impurities by weight.

In some embodiments, the solid dosage form comprises less than 3% of water by weight. In some embodiments, the solid dosage form comprises less than 3% of water by weight after six months of storage at room temperature. In some embodiments, the solid dosage form is characterized by a disintegration time between 1 and 5 minutes.

In some aspects, the present disclosure provides a pharmaceutical solid dosage form for oral delivery of a compound of Formula (I),

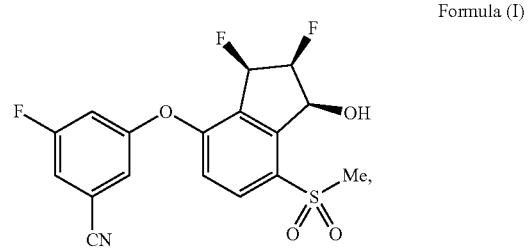 [SMILES: CS(=O)(=O)c1ccc(Oc2cc(F)cc(C#N)c2)c2c1[C@H](O)[C@H](F)[C@@H]2F]

wherein the solid dosage form comprises: (a) a solid dispersion comprising a compound of Formula (I) and a polymer selected from HPMCAS, CAP and SOLUPLUS; and (b) one or more pharmaceutically acceptable excipients.

In some aspects, the present disclosure provides a pharmaceutical solid dosage form for oral delivery of a compound of Formula (I),

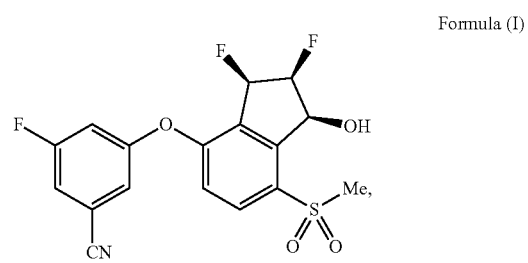 [SMILES: CS(=O)(=O)c1ccc(Oc2cc(F)cc(C#N)c2)c2c1[C@H](O)[C@H](F)[C@@H]2F]

wherein the solid dosage form comprises: (a) a solid dispersion comprising 5 to 100 mg of a compound of Formula (I); and (b) one or more pharmaceutically acceptable excipients.

In some aspects, the present disclosure provides a pharmaceutical solid dosage form for oral delivery of a compound of Formula (I),

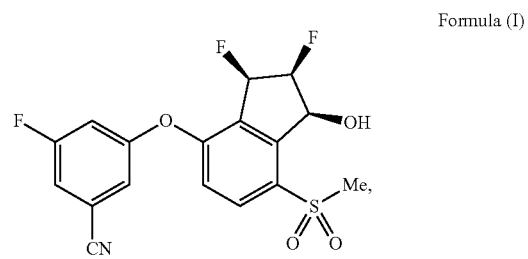 [SMILES: CS(=O)(=O)c1ccc(Oc2cc(F)cc(C#N)c2)c2c1[C@H](O)[C@H](F)[C@@H]2F]

wherein the solid dosage form comprises, by weight relative to the total weight of the pharmaceutical composition:
(a) 15% to 50% of a solid dispersion comprising the compound of Formula (I);
(b) 20% to 50% of a binder;
(c) 20% to 40% of a filler;
(d) 1.0% to 5.0% of a disintegrant; and
(e) 0.25% to 1.25% of a lubricant.

In some aspects, the present disclosure provides a pharmaceutical solid dosage form for oral delivery of a compound of Formula (I),

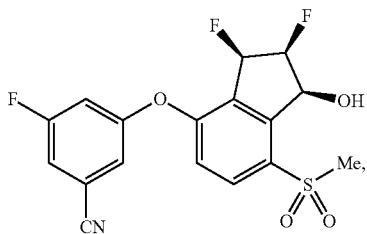

Formula (I)

wherein the solid dosage form comprises, by weight relative to the total weight of the pharmaceutical composition:
(a) 15% to 50% of a solid dispersion comprising the compound of Formula (I) and HMPCAS;
(b) 20% to 50% of a microcrystalline cellulose;
(c) 20% to 40% of a mannitol;
(d) 1.0% to 5.0% of a croscarmellose sodium; and
(e) 0.25% to 1.25% of magnesium stearate.

In some aspects, the present disclosure provides a pharmaceutical solid dosage form for oral delivery of a compound of Formula (I),

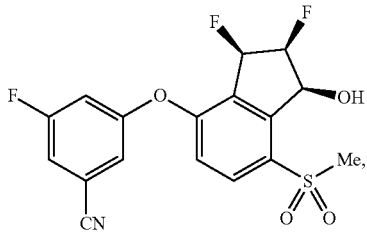

Formula (I)

wherein the solid dosage form comprises, by weight relative to the total weight of the pharmaceutical composition:
(a) 15% to 50% of a solid dispersion comprising the compound of Formula (I);
(b) 20% to 50% of a binder;
(c) 20% to 40% of a filler;
(d) 1.0% to 5.0% of a disintegrant;
(e) 0.25% to 1.25% of a lubricant;
(f) 0.1% to 1.25% of a glidant; and
(g) 1% to 5% of a coating.

In some aspects, the present disclosure provides a pharmaceutical solid dosage form for oral delivery of a compound of Formula (I),

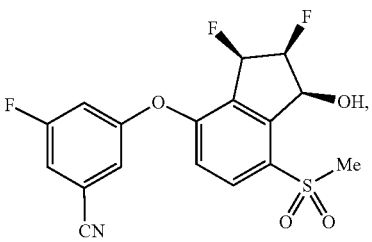

Formula (I)

wherein the solid dosage form comprises, by weight relative to the total weight of the pharmaceutical composition:
(a) 15% to 50% of a solid dispersion comprising the compound of Formula (I) and HMPCAS;
(b) 20% to 50% of a microcrystalline cellulose;
(c) 20% to 40% of a mannitol;
(d) 1.0% to 5.0% of a croscarmellose sodium;
(e) 0.25% to 1.25% of magnesium stearate;
(f) 0.1% to 1.25% of colloidal silicon dioxide; and
(g) optionally, a PVA-based coating.

In some aspects, the present disclosure provides a pharmaceutical solid dosage form for oral delivery of a compound of Formula (I),

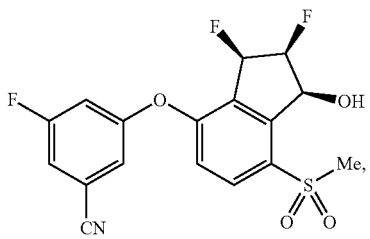

Formula (I)

wherein the solid dosage form comprises: (a) a solid dispersion comprising a compound of Formula (I); and (b) one or more pharmaceutically acceptable excipients, wherein the weight of the solid dosage form is between 50 and 750 mg.

In some aspects, the present disclosure provides a pharmaceutical solid dosage form for oral delivery of a compound of Formula (I),

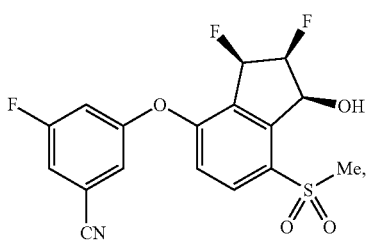

Formula (I)

wherein the solid dosage form comprises: (a) a solid dispersion comprising a compound of Formula (I); (b) one or more pharmaceutically acceptable excipients; and (c) less than 2% of impurities by weight.

In some aspects, the present disclosure provides a pharmaceutical solid dosage form for oral delivery of a compound of Formula (I), Formula (I)

wherein the solid dosage form comprises: (a) a solid dispersion comprising a compound of Formula (I); (b) one or more pharmaceutically acceptable excipients; and (c) less than 3% of water by weight after six months of storage at room temperature.

A compound or solid dispersion of the present disclosure may be formulated in any suitable pharmaceutical formulation. A pharmaceutical composition of the present disclosure typically contains an active ingredient (e.g., a compound of Formula (I)), and one or more pharmaceutically acceptable excipients and/or carriers, including but not limited to, inert solid diluents and fillers, binders, diluents, disintegrants, lubricants, glidants, coatings, sterile aqueous solutions and various organic solvents, permeation enhancers, solubilizers and adjuvants. A compound or solid dispersion of the present disclosure may be formulated in any suitable pharmaceutical formulation. In some embodiments, the pharmaceutically acceptable excipient is selected from microcrystalline cellulose, mannitol, croscarmellose sodium, and magnesium stearate. In some embodiments, the pharmaceutically acceptable excipient is selected from microcrystalline cellulose, mannitol, croscarmellose sodium, magnesium stearate, and Cab-O-Sil. In some embodiments, the present disclosure provides a pharmaceutical composition comprising a compound of Formula (I) and a pharmaceutically acceptable excipient selected from microcrystalline cellulose, mannitol, croscarmellose sodium, and magnesium stearate. In some embodiments, the present disclosure provides a pharmaceutical composition comprising a compound of Formula (I) and a pharmaceutically acceptable excipient selected from microcrystalline cellulose, mannitol, croscarmellose sodium, magnesium stearate, and colloidal silicon dioxide. In some embodiments, the present disclosure provides a pharmaceutical composition comprising a compound of Formula (I), microcrystalline cellulose, mannitol, croscarmellose sodium, and magnesium stearate. In some embodiments, the present disclosure provides a pharmaceutical composition comprising a compound of Formula (I), microcrystalline cellulose, mannitol, croscarmellose sodium, magnesium stearate, Cab-O-Sil, and a PVA-based coating.

Pharmaceutical formulations may be provided in any suitable form, which may depend on the route of administration. In some embodiments, the pharmaceutical composition disclosed herein can be formulated in a dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral administration. For example, the pharmaceutical composition can be formulated in the form of a pill, a tablet, a capsule, an inhaler, a liquid suspension, a liquid emulsion, a gel, or a powder. Preferably, the pharmaceutical composition is formulated in the form of a pill, a tablet, or a capsule. In some embodiments, the pharmaceutical composition can be formulated as a unit dosage in liquid, gel, semi-liquid, semi-solid, foam, or solid form.

The amount of each compound administered will be dependent on the mammal being treated, the severity of the disorder or condition, the rate of administration, the disposition of the compound and the discretion of the prescribing physician. However, an effective dosage may be in the range of about 0.001 to about 100 mg per kg body weight per day, in single or divided doses. In some embodiments, the dosage is in the range of about 0.1 mg/kg to about 1.0 mg/kg body weight per dose. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the disclosure provides a pharmaceutical composition comprising an amount of the compound of Formula (I) formulated for administration to a subject in need thereof. In some embodiments, the pharmaceutical composition comprises between about 0.1-1000 mg of the compound of Formula (I), such as 0.1-500 mg, 1-250 mg, 5-125 mg, 5-100 mg, 5-75 mg, or 5-50 mg of the compound of Formula (I). In some embodiments, the pharmaceutical composition comprises about or more than about 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of the compound of Formula (I). In some embodiments, the pharmaceutical composition comprises between 1-100 mg of the compound of Formula (I) in a single dose, such as 5-50 mg of the compound of Formula (I). In some embodiments, the pharmaceutical composition comprises about 10 mg of the compound of Formula (I). In some embodiments, the pharmaceutical composition comprises about 40 mg of the compound of Formula (I).

In some embodiments, a therapeutically effective amount of the compound of Formula (I), which can be a daily amount administered over the course of a period of treatment, can sufficiently provide any one or more of the therapeutic effects described herein. As an example, the therapeutic effective amount can be in the range of about 0.001-100 mg/kg body weight, 0.001-50 mg/kg body weight, 0.01-50 mg/kg body weight, 0.01-25 mg/kg body weight, 0.01-10 mg/kg body weight, 0.01-5 mg/kg body weight, 0.01-4 mg/kg body weight, 0.01-3 mg/kg body weight, 0.01-2 mg/kg body weight, 0.01-1 mg/kg body weight, 0.01-0.75 mg/kg body weight, 0.1-5 mg/kg body weight, 0.1-4 mg/kg body weight, 0.1-3 mg/kg body weight, 0.1-2 mg/kg body weight, 0.1-1 mg/kg body weight, or 0.1-0.75 mg/kg body weight of the compound of Formula (I). In some embodiments, the therapeutic amount can be about or more than about 0.001 mg/kg body weight, 0.01 mg/kg body weight, 0.1 mg/kg body weight, 0.2 mg/kg body weight, 0.3 mg/kg body weight, 0.4 mg/kg body weight, 0.5 mg/kg body weight, 0.6 mg/kg body weight, 0.7 mg/kg body weight, 0.8 mg/kg body weight, 0.9 mg/kg body weight, 1 mg/kg body weight, 1.5 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, or 10 mg/kg body weight of the compound of Formula (I). In some embodiments, the effective amount is at least about 0.01 mg/kg body weight of the compound of Formula (I). In some embodiments, the effective amount is an amount between about 0.01-10 mg/kg body weight of the compound of Formula (I).

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot every second day to once a month or even longer. Most typically and conveniently for the subject, the compound of Formula (I) inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

Pharmaceutical composition for oral administration: In some embodiments, the disclosure provides a pharmaceutical composition for oral administration containing at least one compound of the present disclosure and a pharmaceutical excipient suitable for oral administration. The composition may be in the form of a solid, liquid, gel, semi-liquid, or semi-solid. In some embodiments, the composition is in the form of a solid. In some embodiments, the composition further comprises a second agent.

In some embodiments, the invention provides a solid pharmaceutical composition for oral administration containing: (i) the compound of Formula (I); and (ii) a pharmaceutical excipient suitable for oral administration. In some embodiments, the composition further contains: (iii) a third agent or even a fourth agent. In some embodiments, each compound or agent is present in a therapeutically effective amount. In other embodiments, one or more compounds or agents is present in a sub-therapeutic amount, and the compounds or agents act synergistically to provide a therapeutically effective pharmaceutical composition.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Preferably, the pharmaceutical composition for oral administration is provided as a tablet. Such dosage forms can be prepared by any of the methods of pharmacy, which typically include the step of bringing the active ingredient(s) into association with the excipient. In general, the composition are prepared by uniformly and intimately admixing the active ingredient(s) with liquid excipients or finely divided solid excipients or both, and then, if necessary, shaping the product into the desired presentation. For example, a tablet can be prepared by compression or molding, optionally with one or more pharmaceutically acceptable excipients. Compressed tablets can be prepared by compressing in a suitable machine the active ingredient(s) in a free-flowing form such as powder or granules, optionally mixed with an excipient such as, but not limited to, a binder, a filler, a disintegrant, a glidant, and/or a lubricant. Molded tablets can be made by molding in a suitable machine a mixture of the powdered compound moistened with an inert liquid diluent.

This disclosure further encompasses anhydrous pharmaceutical compositions and dosage forms comprising an active ingredient, since water can facilitate the degradation of some compounds. For example, water may be added (e.g., 5%) as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, low moisture vapor transmission containers, hermetically sealed foils, plastic or the like, unit dose containers, blister packs, and strip packs.

An active ingredient can be combined in an intimate admixture with a pharmaceutical excipient according to pharmaceutical compounding techniques. The excipient can take a wide variety of forms depending on the form of preparation desired for administration. In preparing the composition for an oral dosage form, any suitable pharmaceutical media can be employed as excipients, such as, for example, water, glycols, oils, alcohols, flavoring agents, preservatives, coloring agents, and the like in the case of oral liquid preparations (such as suspensions, solutions, and elixirs) or aerosols; or excipients such as starches, sugars, micro-crystalline cellulose, diluents, granulating agents, lubricants, glidants, binders, and disintegrating agents can be used in the case of oral solid preparations, in some embodiments without employing the use of lactose. If desired, tablets can be coated by standard aqueous or non-aqueous techniques.

Binders suitable for use in the subject pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof. In some embodiments, the binder is microcrystalline cellulose. In some embodiments, the microcrystalline cellulose is selected from microcrystalline cellulose PH101, microcrystalline cellulose PH105, microcrystalline cellulose PH112, microcrystalline cellulose PH113, microcrystalline cellulose PH200, microcrystalline cellulose PH301, and microcrystalline cellulose PH302. In some embodiments, the binder is microcrystalline cellulose PH101 or microcrystalline cellulose PH105. In some embodiments, the binder is microcrystalline cellulose PH101. In some embodiments the binder is microcrystalline cellulose PH105. In some embodiments the binder is present in an amount of at least 0.5 mg, at least 1 mg, at least 5 mg, at least 10 mg, at least 20 mg, at least 30 mg, at least 50 mg, at least 100 mg, at least 150 mg, at least 200 mg, at least 300 mg, or at least 500 mg.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In some embodiments, the filler is mannitol. In some embodiments, the mannitol is selected from mannitol M100, mannitol M200, and mannitol M300. In some embodiments, the filler is mannitol M100. In some embodiments the filler is present in an amount of at least 0.5 mg, at least 1 mg, at least 5 mg, at least 10 mg, at least 20 mg, at least 30 mg, at least 50 mg, at least 100 mg, at least 150 mg, at least 200 mg, at least 300 mg, or at least 500 mg.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration. About 0.5 to about 15 weight percent of disintegrant, such as about 1.0 to about 5.0 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof. In some embodiments, the disintegrant is croscarmellose sodium.

Lubricants which can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyllaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition. In some embodiments, the lubricant is magnesium stearate. In some embodiments, the lubricant is present in an amount of at least 0.1 mg, at least 0.2 mg, at least 0.3 mg, at least 0.4 mg, at least 0.5 mg, at least 0.6 mg, at least 0.7 mg, at least 0.8 mg, at least 0.9 mg, at least 1 mg, or at least 5 mg.

Glidants which can be used to form pharmaceutical compositions and dosage forms of the disclosure include, but are not limited to, colloidal silicon dioxide, CAB-O-SIL® (Cabot Co. of Boston, MA), asbestos-free talc, magnesium stearate, starch, and talc. In some embodiments, the glidant is present in an amount of at least 0.1 mg, at least 0.2 mg, at least 0.3 mg, at least 0.4 mg, at least 0.5 mg, at least 0.6 mg, at least 0.7 mg, at least 0.8 mg, at least 0.9 mg, at least 1 mg, at least 1.1 mg, at least 1.2 mg, at least 1.3 mg, at least 1.4 mg, at least 1.5 mg, at least 2 mg, at least 3 mg, at least 4 mg, or at least 5 mg.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. A coating may further prevent or slow moisture sorption. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Enteric-coatings include, but are not limited to, CAP, acrylate polymers, HPMCP, HPMC, PVAP, PVA, fatty acids, fats, phenyl salicylate, waxes, shellac, ammoniated shellac, and cellulose acetate phthalates. Non-enteric coatings include, but are not limited to, HPMC, methyl hydroxyethyl celluloses (MHEC), EC, HPC, povidone, sodium carboxymethylcellulose (SCMC), PEG, and acrylate polymers. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. In some embodiments, the coating is PVA-based, such as OpaDry II. In some embodiments, the coating is pigmented. For example, the coating may comprise blue, green, red, purple, orange, silver and/or yellow pigments. In some embodiments, the coating is OpaDry II, such as OpaDry II Blue. In some embodiments the coating is present in an amount of at least 0.5 mg, at least 1 mg, at least 2.5 mg, at least 5 mg, at least 7.5 mg, at least 10 mg, at least 12.5 mg, at least 15 mg, at least 17.5 mg, at least 20 mg, at least 25, or at least 30 mg.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

When the method of the disclosure involves combination therapy, for example, wherein a secondary agent is co-administered with a compound of Formula (I), the agents may be administered separately, at the same, or at different times of the day, or they may be administered in a single composition. In the combination therapies of the disclosure, each agent can be administered in an "immediate release" manner or in a "controlled release manner." When the additional active agent is a corticosteroid, for instance, any dosage form containing both active agents, such as both the compound of Formula (I) and the corticosteroid, can provide for immediate release or controlled release of the corticosteroid, and either immediate release or controlled release of the compound of Formula (I). In other formulations of the present disclosure, two or more additional active agents, which may or may not be in the same class of drug, can be present in combination, along with the compound of Formula (I). In such a case, the effective amount of either or each individual additional active agent present will generally be reduced relative to the amount that would be required if only a single added agent were used.

In some embodiments, a solid dispersion, solid dosage form or pharmaceutical composition provided herein, or a composition comprising a solid dispersion, solid dosage form or pharmaceutical composition provided herein, is administered orally, parenterally, topically, or mucosally. In some embodiments, a solid dispersion, solid dosage form or pharmaceutical composition provided herein, or a composition comprising a solid dispersion, solid dosage form or pharmaceutical composition provided herein, is administered orally.

In some embodiments, a solid dispersion, solid dosage form or pharmaceutical composition provided herein, or a composition comprising a solid dispersion, solid dosage form or pharmaceutical composition provided herein, is administered at a dosing frequency of once, twice, thrice, or four times daily. In some embodiments, a solid dispersion, solid dosage form or pharmaceutical composition provided herein, or a composition comprising a solid dispersion, solid dosage form or pharmaceutical composition provided herein, comprises the compound of Formula (I) in an amount of from about 0.1 to about 100 mg, from about 0.5 to about 75 mg, from about 5 to about 50 mg, from about 5 mg to about 45 mg, from about 5 to about 15 mg, or from about 35 to about 45 mg. In some embodiments, provided herein is a single unit dosage form suitable for oral administration to a human comprising: an amount equal to or greater than about 1, 2, 3, 4, 5, 10, 15, 20, 25, 30, 35, 40, 45, 50, 60, 70, 80, 90 or 100 mg of the compound of Formula (I); and a pharmaceutically acceptable excipient. In some embodiments, the amount of the active ingredient is about 10 mg. In some embodiments, the amount of the active ingredient is about 40 mg.

In some embodiments, a second active agent is administered once or twice daily, once every other day, once every week, once every two weeks, or once every three weeks, in an amount of from about 1 to about 1000 mg, from about 5 to about 500 mg, from about 10 to about 350 mg, or from about 50 to about 200 mg. In some embodiments, the second active agent is administered orally or intravenously. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. A solid dispersion comprising the compound of Formula (I) provided herein and other active ingredients can be administered to a patient prior to, during, or after the occurrence of the adverse effect associated with conventional therapy.

Processes for Preparing a Pharmaceutical Composition

In certain aspects, the present disclosure provides a process of preparing a solid dosage form, comprising: (a) mixing the compound of Formula (I) and one or more pharmaceutically acceptable excipients to form milled granules; and (b) compressing the granules by applying a compression force of 5 kN to 20 kN.

In certain aspects, the present disclosure provides a process for preparing a solid dosage form, comprising: (a) blending a compound of Formula (I), a binder, a filler, a disintegrant and a lubricant, thereby forming a blended mixture; (b) granulating the blended mixture, optionally using a roller compactor, thereby forming a granulated mixture; (c) mixing a second filler, a second disintegrant and a second lubricant with the granulated mixture, thereby forming a tableting mixture; and (d) compressing the tableting mixture into a tablet, wherein the filler and the second filler are the same or different; the disintegrant and the second disintegrant are the same or different; and the lubricant and the second lubricant are the same or different. In some embodiments, the binder is microcrystalline cellulose, the filler is mannitol, the disintegrant is croscarmellose sodium and the lubricant is magnesium stearate. In some embodiments, the second filler is mannitol, the second disintegrant is croscarmellose sodium, and the second lubricant is magnesium stearate. The process may further comprise mixing a glidant with the granulated mixture. In some embodiments, the glidant is colloidal silicon dioxide, such as Cab-O-Sil. In some embodiments, the process further comprises coating the tablet. The coating may be a PVA-based coating, such as OpaDry II.

In some embodiments, the process comprises pre-coating a blender shell with the binder, optionally wherein the binder is microcrystalline cellulose. Pre-coating the blender shell may comprise blending the binder, such as blending the binder for at least 1 minute. The process may further comprise mixing the intra-granular ingredients in the coated blender, optionally wherein the intra-granular ingredients comprise the compound of Formula (I), a binder, a filler, a disintegrant, and optionally a lubricant. The mixing may comprise blending for at least 5 minutes, optionally at a speed of 15 rpm or higher. In some embodiments, the process further comprises milling the blended intra-granular ingredients. The process may further comprise mixing the milled intra-granular ingredients in a blender, such as blending for at least 10 minutes at a speed of at least 15 rpm. In some embodiments, a lubricant, such as magnesium stearate, is added to the blender and mixed with the milled and blended intra-granular ingredients. This mixture may be granulated, optionally using a roller compactor. Optionally, the process further comprises passing the granulated material through a mill. The process may further comprise transferring the milled granules into a blender and mixing with the extra-granular ingredients, optionally wherein the extra-granular ingredients comprise a filler and a disintegrant. In some embodiments, the process further comprises adding a lubricant, such as magnesium stearate, to the mixture and mixing to form a tablet blend. In some embodiments, the process further comprises adding a glidant, such as colloidal silicon dioxide, to the mixture and mixing to form a tablet blend. Optionally, the tablet blend is compacted using a roller compaction. In some embodiments, the process comprises compressing the tablet blend into a tablet. In some embodiments, the tablets are oval in shape. In some embodiments, the compression force of the press is between 5 and 20 kN, such as about 7.5 kN or about 15 kN. In some embodiments, the tablet consists of about 500 mg of the tablet blend, such as 500±25 mg. In some embodiments, the tablet consists of about 125 mg of the tablet blend, such as 125±10 mg.

Packaged Compositions and Kits

In certain aspects, the present disclosure provides a packaged solid dispersion comprising a solid dispersion described herein and a desiccant. Suitable desiccants include silica gel, bentonite clay, or molecular sieves. In some embodiments, the packaging comprises a low moisture vapor transmission container, such as an HDPE bottle, an LDPE bag, a double LDPE bags goosed neck with a cable tie, an HDPE bottle sealed with a screw cap enclosure, an HDPE drum, or a combination thereof.

In certain aspects, the present disclosure provides a packaged solid dosage form comprising a solid dosage form described herein and a desiccant. Suitable desiccants include silica gel, Sorb-it, Clariant, bentonite clay, or molecular sieves. In some embodiments, the packaging comprises a low moisture vapor transmission container, such as an HDPE bottle, an LDPE bag, a double LDPE bags goosed neck with a cable tie, an HDPE bottle sealed with a screw cap enclosure, an HDPE drum, foil-foil blisters, cold-form foil-foil blisters, aluminum-aluminum blisters, cold-form aluminum-aluminum blisters, polyvinyl chloride (PVC) blisters, polyvinylidene chloride (PVDC) blisters, Aclar blisters, poly-chloro-tri-fluoro-ethylene (PCTFE) blisters, a plastic bottle, a multilayer bottle, or a combination thereof. The packaged solid dosage form may further comprise a cotton, rayon or polyester coil. In some embodiments, the packaged solid dosage form comprises a bottle, such as an HDPE bottle, that contains the solid dosage form, a desiccant, and optionally a cotton, rayon or polyester coil. In some embodiments, the packaged solid dosage form comprises a bottle, such as an HDPE bottle, that contains the solid dosage form, a desiccant, and a cotton, rayon or polyester coil.

In certain aspects, the present disclosure provides a kit comprising a solid dosage form described herein and instructions for administering the solid dosage form to a subject in need thereof. In some embodiments, the kit comprises a solid dosage form comprising the compound of Formula (I), packaged in a low moisture vapor transmission container with a desiccant. Optionally, a label is on or associated with the container. For example, a label is on a container when letters, numbers or other characters forming the label are attached, molded or etched on the container itself, and a label is associated with a container when it is present within a receptacle or carrier, such as a box, that also holds the container, e.g., as a package insert. In addition, a label may be used to indicate that the contents are to be used for a specific therapeutic application. In some embodiments, the label includes directions for use of the contents, such as in the methods described herein. In some embodiments, a pharmaceutical composition provided herein is presented in a pack or container that contains one or more unit dosage forms comprising the compound of Formula (I). The pack may contain metal or plastic foil, such as a blister pack. The pack or container may be accompanied by instructions for administration of the unit dosage form. In some embodiments, the pack or container is accompanied with a notice in a form prescribed by a governmental agency regulating the manufacture, use or sale of pharmaceuticals, which notice is reflective of approval by the agency of the form of the drug for human or veterinary administration. Such notice, for example, may be the labeling approved by the U.S. Food and Drug Administration for prescription of drugs, or the approved product insert. In some embodiments, compositions comprising the compound of Formula (I) are prepared, placed in an appropriate container, and labeled for treatment of an indicated condition.

Methods of Treatment

In one aspect, the present disclosure provides a method for treating a proliferative disorder in a subject in need thereof, comprising administering to said subject a solid dispersion, solid dosage form or pharmaceutical composition provided herein. In some embodiments, the proliferative disorder is a cancer condition. In some further embodiments, said cancer condition is a cancer selected from the group consisting of lung cancer, head and neck squamous cell carcinoma, pancreatic cancer, breast cancer, ovarian cancer, renal cell carcinoma, prostate cancer, neuroendocrine cancer, gastric cancer, bladder cancer and colon cancer. In some further embodiments, the cancer condition is renal cell carcinoma. In certain aspects, the present disclosure provides a method of treating renal cell carcinoma, comprising administering to a subject in need thereof an effective amount of a solid dispersion, solid dosage form or pharmaceutical composition provided herein. In some embodiments, the renal cell carcinoma is clear cell renal cell carcinoma.

In some embodiments, the present disclosure provides a method of treating a cancer condition, wherein the compound of Formula (I) is effective in one or more of inhibiting proliferation of cancer cells, inhibiting metastasis of cancer cells, killing cancer cells and reducing severity or incidence of symptoms associated with the presence of cancer cells. In some other embodiments, said method comprises administering to the cancer cells a therapeutically effective amount of a solid dispersion, solid dosage form or pharmaceutical composition provided herein. In some embodiments, the administration takes place in vitro. In other embodiments, the administration takes place in vivo.

In some embodiments, the present invention provides a method of treating von Hippel-Lindau (VHL) disease, comprising administering to a subject in need thereof a solid dispersion, solid dosage form or pharmaceutical composition provided herein. In some embodiments, the subject also suffers from a hemangioblastoma, a pheochromocytoma, a pancreatic neuroendocrine tumor or renal cell carcinoma. In some embodiments, the subject suffers from renal cell carcinoma. VHL disease is an autosomal dominant syndrome that not only predisposes patients to kidney cancer (~70% lifetime risk), but also to hemangioblastomas, pheochromocytoma and pancreatic neuroendocrine tumors. VHL disease results in tumors with constitutively active HIF-α proteins with the majority of these dependent on HIF-2α activity (Maher, et al. *Eur. J. Hum. Genet.* 19:617-623, 2011). HIF-2α has been linked to cancers of the retina, adrenal gland and pancreas through both VHL disease and activating mutations. Recently, gain-of-function HIF-2α mutations have been identified in erythrocytosis and paraganglioma with polycythemia (Zhuang, et al. *NEJM* 367: 922-930, 2012; Percy, et al. *NEJM* 358:162-168, 2008; and Percy, et al. *Am. J. Hematol.* 87:439-442, 2012). Notably, a number of known HIF-2α target gene products (e.g., VEGF, PDGF, and cyclin D1) have been shown to play pivotal roles in cancers derived from kidney, liver, colon, lung, and brain. In fact, therapies targeted against one of the key HIF-2α regulated gene products, VEGF, have been approved for the treatment of these cancers.

As used herein, a therapeutically effective amount of a solid dispersion, solid dosage form or pharmaceutical composition refers to an amount of the compound of Formula (I) sufficient to effect the intended application, including but not limited to, disease treatment, as defined herein. Also contemplated in the subject methods is the use of a subtherapeutic amount of the compound of Formula (I) for treating an intended disease condition.

The amount of the solid dispersion, solid dosage form or pharmaceutical composition administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of HIF-2α can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with a solid dispersion, solid dosage form or pharmaceutical composition of the present disclosure may be monitored to determine the effectiveness of treatment, and the treatment regimen may be adjusted based on the subject's physiological response to treatment. For example, if inhibition of a biological effect of HIF-2α inhibition is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with the compound of Formula (I) is discontinued if inhibition of the biological effect is above or below a threshold, such as in a lack of response or an adverse reaction. The biological effect may be a change in any of a variety of physiological indicators.

In general, a HIF-2α inhibitor, such as the compound of Formula (I), is a compound that inhibits one or more biological effects of HIF-2α. Examples of biological effects of HIF-2α include, but are not limited to, heterodimerization of HIF-2α to HIF-1β, HIF-2α target gene expression, VEGF gene expression, and VEGF protein secretion. In some embodiments, the HIF-2α inhibitor is selective for HIF-2α, such that the inhibitor inhibits heterodimerization of HIF-2α to HIF-1β but not heterodimerization of HIF-1α to HIF-1β.

Such biological effects may be inhibited by about or more than about 10%, 20%, 30%, 40%, 50%, 60%, 70%, 80%, 90%, 95%, or more.

Hypoxia-inducible factors (HIFs), like HIF-2α, are transcription factors that respond to changes in available oxygen in the cellular environment (e.g. a decrease in oxygen, or hypoxia). The HIF signaling cascade mediates the effects of hypoxia, the state of low oxygen concentration, on the cell. Hypoxia often keeps cells from differentiating. However, hypoxia promotes the formation of blood vessels, and is important for the formation of a vascular system in embryos, and cancer tumors. The hypoxia in wounds also promotes the migration of keratinocytes and the restoration of the epithelium. The compound of Formula (I) may be administered in an amount effective in reducing any one or more of such effects of HIF-2α activity.

HIF-2α activity can be inhibited by inhibiting heterodimerization of HIF-2α to HIF-1β (ARNT), such as with the compound of Formula (I). A variety of methods for measuring HIF-2α dimerization are available. In some embodiments, the HIF-2α inhibitor binds the PAS-B domain cavity of HIF-2α.

Inhibition of heterodimerization of HIF-2α to HIF-1β (ARNT) may also be determined by a reduction in HIF-2α target gene mRNA expression. mRNA quantitation can be performed using real-time PCR technology. (Wong, et al, "Real-time PCR for mRNA quantitation", 2005. BioTechniques 39, 1:1-1.). Yet another method for determining inhibition of heterodimerization of HIF-2α to HIF-1β (ARNT) is by co-immunoprecipitation.

As described herein, HIF-2α is a transcription factor that plays important roles in regulating expression of target genes. Non-limiting examples of HIF-2α target genes include HMOX1, SFTPA1, CXCR4, PAI1, BDNF, hTERT, ATP7A, and VEGF. For instance, HIF-2α is an activator of VEGF. Further non-limiting examples of HIF-2α target genes include HMOX1, EPO, CXCR4, PAI1, CCND1, CLUT1, IL6, and VEGF. The compound of Formula (I) may be administered in an amount effective in reducing expression of any one or more of genes induced by HIF-2α activity. A variety of methods is available for the detection of gene expression levels, and includes the detection of gene transcription products (polynucleotides) and translation products (polypeptides). For example, gene expression can be detected and quantified at the DNA, RNA or mRNA level. Various methods that have been used to quantify mRNA include in situ hybridization techniques, fluorescent in situ hybridization techniques, reporter genes, RNase protection assays, Northern blotting, reverse transcription (RT)-PCR, SAGE, DNA microarray, tiling array, and RNA-seq. Examples of methods for the detection of polynucleotides include, but are not limited to selective colorimetric detection of polynucleotides based on the distance-dependent optical properties of gold nanoparticles, and solution phase detection of polynucleotides using interacting fluorescent labels and competitive hybridization. Examples for the detection of proteins include, but are not limited to microscopy and protein immunostaining, protein immunoprecipitation, immunoelectrophoresis, western blot, BCA assay, spectrophotometry, mass spectrophotometry and enzyme assay.

In some embodiments, inhibition of HIF-2α is characterized by a decrease in VEGF gene expression. The decrease may be measured by any of a variety of methods, such as those described herein. As a further example, the mRNA expression level of VEGF can be measured by quantitative PCR (QT-PCR), microarray, RNA-seq and nanostring. As another example, an ELISA assay can be used to measure the level VEGF protein secretion.

In certain aspects, the present disclosure provides a method of treating a HIF-2α-mediated disease or condition, comprising administering to a subject in need thereof a therapeutically effective amount of a solid dispersion, solid dosage form or pharmaceutical composition described herein. In some embodiments, the disease or condition is cancer. In some embodiments, the disease or condition is selected from renal cell carcinoma, von Hippel-Lindau disease, pulmonary arterial hypertension, glioblastoma, and colitis.

In some embodiments, provided herein is a method of inhibiting HIF-2α, comprising contacting HIF-2α with an effective amount of a solid dispersion, solid dosage form or pharmaceutical composition described herein. In some other embodiments, the subject methods are useful for treating a disease condition associated with HIF-2α. Any disease condition that results directly or indirectly from an abnormal activity or expression level of HIF-2α can be an intended disease condition. In some embodiments, the disease condition is a proliferative disorder, such as described herein, including but not limited to cancer. A role of HIF-2α in tumorigenesis and tumor progression has been implicated in many human cancers. Constitutively active HIF-2α may be the result of defective VHL or a low concentration of oxygen in a cancer cell. Rapidly growing tumors are normally hypoxic due to poor vascularization, a condition that activates HIF-2α in support of tumor cell survival and proliferation. Constitutive activation of HIF-2α is emerging as a common theme in diverse human cancers, consequently agents that target HIF-2a have therapeutic value.

The data presented in the Examples herein below demonstrate the anti-cancer effects of the compound of Formula (I). As such, the subject method is particularly useful for treating a proliferative disorder, such as a neoplastic condition. Non-limiting examples of such conditions include but are not limited to acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basal-like carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathy-associated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, *glomus* tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, non-melanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof.

In some embodiments, the methods of administering a solid dispersion, solid dosage form or pharmaceutical composition described herein are applied to the treatment of cancers of the adrenal glands, blood, bone marrow, brain, breast, cervix, colon, head and neck, kidney, liver, lung, ovary, pancreas, plasma cells, rectum, retina, skin, spine, throat or any combination thereof.

Some embodiments of the present disclosure contemplate a human subject, such as a subject that has been diagnosed as having or being at risk for developing or acquiring a proliferative disorder condition. Certain other embodiments contemplate a non-human subject, for example a non-human primate such as a macaque, chimpanzee, gorilla, vervet, orangutan, baboon or other non-human primate, including such non-human subjects that can be known to the art as preclinical models. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present invention, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the methods of the present disclosure in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the methods of the present disclosure can be determined by a number of secondary parameters. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932, 412).

In some embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In one aspect, the disclosure provides a method of treating pulmonary arterial hypertension (PAH). In one embodiment, the method comprises administering an effective amount of a solid dispersion, solid dosage form or pharmaceutical composition described herein to said subject. PAH is a life-threatening and progressive disease of various origins characterized by pulmonary vascular remodeling that leads to increased pulmonary vascular resistance and pulmonary arterial pressure, most often resulting in right-sided heart failure. The most common symptom at presentation is breathlessness, with impaired exercise capacity as a hallmark of the disease. PAH includes idopathic PAH, heritable PAH (e.g. BMPR2, ALK1, endoglin), drug-induced PAH, toxin-induced PAH, and PAH associated with another condition (e.g. connective tissue diseases, HIV infection, portal hypertension, congenital heart diseases, schistosomiasis, or chronic hemolytic anemia). Idiopathic PAH occurs in the absence of known risk factors and is the most common form of the disease. The PAH condition treated in accordance with the present disclosure can include any of these PAH conditions.

In general, the median period of survival of PAH after diagnosis, based on an early U.S. National Institutes of Health Registry with prospective follow-up, is less than 3 years for 194 untreated patients with idiopathic or heritable PAH (formerly called primary pulmonary hypertension) with a mean age of 36 years. At present, average survival after diagnosis in adults is estimated at 5 to 7 years, with a similarly poor overall prognosis in children. In some embodiments, the solid dispersion, solid dosage form or pharmaceutical composition is administered in an amount effective to increase average survival among a treated population of subjects, such as by about or more than about 0.5, 1, 2, 3, 4, 5, 6, 7, 8, 9, 10, 15, or more years.

The pathology of PAH can include pathologic changes in the intima, media, and adventitial layers of the vascular wall. Both vascular endothelial and smooth muscle cells have characteristics of abnormal growth, with excess cellular proliferation and apoptosis resistance. These abnormalities in resident vascular cells, in combination with inflammation, excess vasoconstriction, and in situ thrombosis, can contribute to physical narrowing of the distal pulmonary arterioles. Without being bound by any theory, this narrowing can cause increase in pulmonary vascular resistance, which leads to the chronic and progressive elevation of pulmonary arterial pressure. In some cases, PAH can be induced by hypoxia. In some embodiments, the solid dispersion, solid dosage form or pharmaceutical composition is administered in an amount effective to delay, reduce the incidence of, or reduce the severity of one or more such symptoms associated with PAH.

Treating PAH includes treating a subject diagnosed with existing PAH, as well as preventing PAH. In some embodiments, the amount of the solid dispersion, solid dosage form or pharmaceutical composition administered to the subject (either in a single dose or over multiple doses) is effective in delaying the onset of or reducing the incidence of one or more symptoms of PAH. The delay or reduction in incidence may be with respect to a reference population, such as an untreated population of subjects having PAH or subjects having PAH but treated with another agent. Delay or reduction in incidence of one or more symptoms of PAH may be a reduction of about or more than about 10%, 20%, 30%, 40%, 50%, 60%, 70%, 80%, 90%, 95%, or more. In some embodiments, delay or reduction in incidence is measured by an increased time in disease progression, such as between the appearance of one or more first symptoms, and the appearance of one or more second symptoms. Delay may be about or more than about days, weeks, months, or years (e.g. 1, 2, 3, 4, 5, 6, 7, or more days; 1, 2, 3, 4, 5, 6, 7, 8, or more weeks; 1, 2, 3, 4, 5, 6, or more months; or 1, 2, 3, 4, 5, or more years). In the case of prevention, the subject may be an individual at risk of developing PAH.

In one embodiment, the amount of the solid dispersion, solid dosage form or pharmaceutical composition administered to the subject (either in a single dose or over multiple doses) is effective in (a) stabilizing pulmonary arterial pressure (PAP) as compared to a PAP trend in the subject prior to treatment, or (b) reducing PAP relative to a starting level of PAP in the subject; wherein the PAP is systolic pulmonary arterial pressure (SPAP) or diastolic pulmonary arterial pressure (DPAP). A variety of methods for measuring PAP are available. For example, the PAP can be measured by inserting a catheter into the pulmonary artery. Typically, the mean pressure is 9-18 mmHg, and the wedge pressure measured in the left atrium can be 6-12 mmHg. The wedge pressure may be elevated in left heart failure, mitral valve stenosis, and other conditions, such as sickle cell disease.

PAP in a subject may be stabilized at a level existing at the start of treatment, such as for days, weeks, months or years. In some embodiments, a starting level of PAP in the subject may be reduced by about or more than about 5%, 10%, 15%, 20%, 25%, 30%, 35%, 40%, 45%, 50%, or more. In some embodiments, a rate of PAP increase may be reduced by about or more than about 10%, 20%, 30%, 40%, 50%, 60%, 70%, 80%, 90%, 95%, or more.

The amount of the solid dispersion, solid dosage form or pharmaceutical composition administered to the subject (either in a single dose or over multiple doses) can be effective in reducing right ventricular hypertrophy as measured by Fulton's Index relative to an untreated population of subjects having PAH. Fulton's Index is a measure of the ratio between the mass of the right ventricle to the combined mass of the left ventricle and septum (RV/(LV+S)). Mass can be measured directly (e.g. in the context of an animal study) or extrapolated from volume measurements of a live subject (e.g. as determined by echocardiogram). Reduction may be with respect to an untreated population of subjects with PAH. For example, the average reduction in the Fulton Index among a population of PAH subjects treated with a the compound of Formula (I) as compared to an untreated population of PAH subjects can be about or more than about 5%, 10%, 15%, 20%, 25%, 30%, 35%, 40%, 45%, 50%, or more. In some embodiments, the reduction in Fulton's Index is at least about 20%.

In some embodiments, the amount of the solid dispersion, solid dosage form or pharmaceutical composition administered to the subject (either in a single dose or over multiple doses) is effective in reducing a physiological indicator of PAH. The reduction may be measured over a specified period, such as a level of reduction days (e.g. about or more than about 1, 2, 3, 4, 5, 6, 7 or more days), weeks (e.g. 1, 2, 3, 4, 5, 6, or more weeks), months (e.g. 1, 2, 3, 4, 5, 6, 8, 10, or more months), or longer (e.g. 1, 2, 3, 4, 5, or more years) after treatment is initiated (which treatment may be ongoing through the period). Any of a variety of physiological indicators can be measured, such as pulmonary vascular resistance, pulmonary arterial pressure, systemic arterial pressure, mixed venous oxygen saturation, arterial oxygen saturation, cardiac index, pulmonary capillary wedge pressure, right atrial pressure, six-minute walk distance, brain natriuretic peptide level, and lung diffusion capacity. For example, the solid dispersion, solid dosage form or pharmaceutical composition may be present in an amount effective in (a) reducing one or more of: pulmonary vascular resistance, pulmonary arterial pressure, systemic arterial pressure, pulmonary capillary wedge pressure, right atrial pressure, and brain natriuretic peptide level; and/or (b) increasing one or more of: mixed venous oxygen saturation, arterial oxygen saturation, cardiac index, six-minute walk distance, and lung diffusion capacity. The amount of the solid dispersion, solid dosage form or pharmaceutical composition may be effective in increasing time to death, increasing time to clinical worsening, reducing incidence of right heart failure, or promoting a favorable change in WHO functional class.

One physiological indicator of PAH is pulmonary vascular resistance (PVR). The baseline or reference PVR level can be 200 dyn·sec/cm$^5$ or greater, 240 dyn·sec/cm$^5$ or greater, 300 dyn·sec/cm$^5$ or greater, 400 dyn·sec/cm$^5$ or greater, 500 dyn·sec/cm$^5$ or greater, 600 dyn·sec/cm$^5$ or greater, 700 dyn·sec/cm$^5$ or greater, or 800 dyn·sec/cm$^5$ or greater. In some embodiments, a treatment provided herein is efficacious if after treatment has started, the endpoint PVR level of the subject decreases from the baseline or reference PVR level by 70 dyn·sec/cm$^5$ or more, 100 dyn·sec/cm$^5$ or more, 130 dyn·sec/cm$^5$ or more, or 160 dyn·sec/cm$^5$ or more.

Another physiological indicator of PAH is pulmonary arterial pressure (PAP). The baseline or reference PAP level can be 20 mmHg or greater, 25 mmHg or greater, 30 mmHg or greater, 35 mmHg or greater, 40 mmHg or greater, 45 mmHg or greater, 50 mmHg or greater, 60 mmHg or greater, or 70 mmHg or greater. In some embodiments, a treatment provided herein is efficacious if, after treatment has started, the endpoint PAP level of the subject decreases from the baseline or reference PAP level by 0.5 mmHg or more, 1 mmHg or more, 1.5 mmHg or more, 5 mmHg or more, 10 mmHg or more, 20 mmHg or more, 30 mmHg or more, 40 mmHg or more, or 50 mmHg.

Another physiological indicator of PAH is cardiac index (CI). A baseline or reference CI level can be 5 L/min/m$^2$ or lower, 2.5 L/min/m$^2$ or lower, 2 L/min/m$^2$ or lower, 1.5 L/min/m$^2$ or lower, or 1 L/min/m$^2$ or lower. In some embodiments, a treatment provided herein is efficacious if, after treatment has started, the endpoint CI level increases from the baseline or reference CI level by 0.1 or more, 0.2 or more, 0.3 or more, 0.4 or more, 0.5 or more, 1 or more, or 2 or more.

Another physiological indicator of PAH is pulmonary capillary wedge pressure (PCWP). A baseline or reference PCWP level can be 36 mmHg or less, 24 mmHg or less, 18 mmHg or less, 10 mmHg, or 5 mmHg or less. In some embodiments, a treatment provided herein is efficacious if, after treatment has started, the endpoint PCWP level increases from the baseline or reference PCWP level by 0.2 mmHg or more, 0.3 mmHg or more, 0.4 mmHg or more, 0.5 mmHg or more, 0.6 mmHg or more, 1 mmHg or more, or 5 mmHg or more.

Another physiological indicator of PAH is right atrial pressure (RAP). A baseline or reference RAP level can be 4 mmHg or more, 6 mmHg or more, 8 mmHg or more, 10 mmHg or more, 12 mmHg or more, 16 mmHg or more, 20 mmHg or more, or 25 mmHg or more. In some embodiments, a treatment provided herein is efficacious if after treatment has started, the endpoint RAP level of the subject decreases from the baseline or reference RAP level by 5 mmHg or more, 2.5 mmHg or more, 1 mmHg or more, 0.5 mmHg or more, or 0.2 mmHg or more.

Another physiological indicator of PAH is six-minute walk distance (6 MWD). A baseline or reference 6 MWD can be 50 m or less, 100 m or less, 200 m or less, 300 m or less, 400 m or less, or 500 m or less. In some embodiments, a treatment provided herein is efficacious if, after treatment has started, the endpoint 6 MWD of the subject increases from the baseline or reference 6 MWD by 10 m or more, 15 m or more, 20 m or more, 25 m or more, 30 m or more, or 50 m or more; or if the endpoint 6 MWD of the subject increases by 3% or more, 4% or more, 5% or more, 10% or more, or 20% or more of the baseline level.

Another physiological indicator of PAH is brain natriuretic peptide (BNP) level. A baseline or reference BNP level can be 60 μg/mL or higher, 80 μg/mL or higher, 100 μg/mL or higher, 120 μg/mL or higher, 140 μg/mL or higher, 200 μg/mL or higher, 500 μg/mL or higher, or 1000 μg/mL or higher. In some embodiments, a treatment provided herein is efficacious if, after treatment has started, the endpoint BNP level of the subject decreases from the baseline or reference BNP level. For example, the endpoint BNP level of the subject can decrease by 1 μg/mL or more, 2 μg/mL or more, 5 μg/mL or more, 10 μg/mL or more, 20 μg/mL or more, 100 μg/mL or more, 500 μg/mL or more, or 1000 μg/mL or more.

Diffusion of lung capacity (DLCO), or diffusion capacity of CO, can also be used as a physiological indicator of PAH. A baseline or reference DLCO can be 90% or less, 80% or less, 70% or less, 50% or less, 45% or less, or 40% or less. In some embodiments, a treatment provided herein is efficacious if, after treatment has started, the endpoint DLCO is increased from the baseline level. For example, the endpoint DLCO can be increased from the baseline or reference DLCO by 1% or more, 5% or more, 10% or more, 15% or more, 20% or more, or 50% or more.

Average survival rate can be used as a parameter to determine efficacy in a population of one or more subjects. A reference average survival rate can be 95% or lower, 93% or lower, 90% or lower, 86% or lower, 82% or lower, or 78% or lower. The average survival rate can be an average 1-year survival rate. In some embodiments, a treatment provided herein is efficacious in a population of one or more subjects if, after treatment has started, the average survival rate increases. For example, the average survival rate can increase from the reference average survival rate by 1% or more, 2% or more, 5% or more, 10% or more, or 20% or more.

In one aspect, the disclosure provides a method of treating glioblastoma (including glioblastoma multiforme, or GBM) in a subject in need thereof. In one embodiment, the method comprises administering an effective amount of a solid dispersion, solid dosage form or pharmaceutical composition described herein to said subject. Gliomas are a heterogeneous tumor, typically composed of tumor cells and glioma cancer stem cells (GSC), which promote self-renewal, proliferation and survival. These stem cell populations may preferentially express HIF-2α regulated genes, such as VEGF, Oct4, Glut-1, NOTCH, and prostatic acid phosphatase (PAP). The GSC populations tend to reside within a perivascular niche to support vessel function and tumor growth along with displaying resistance to radiation. The effects of aggressive glioma growth and stem cell like phenotypes may be mediated by signal transduction pathways upstream of HIF, such as PI3K/AKT/mTOR, and a general increase in HIF-2α activity. Histopathological features of GBM include infiltrative invasion into brain parenchyma, significant foci of palisading necrosis and extensive patterns of microvascular proliferation. In some embodiments, the solid dispersion, solid dosage form or pharmaceutical composition is administered in an amount effective to delay progression of, reduce the incidence of, or reduce the degree of one or more of these characteristics associated with glioblastoma, or other characteristics as described herein. In some embodiments, the solid dispersion, solid dosage form or pharmaceutical composition is administered (either in a single dose or over multiple doses) in an amount effective to increase average survival among a treated population of subjects, such as by about or more than about 0.5, 1, 2, 3, 4, 5, 6, 7, 8, 9, 10, 15, or more years.

Treating glioblastoma includes treating a subject diagnosed with existing glioblastoma, as well as preventing glioblastoma, such as in a subject at risk for developing glioblastoma. In some embodiments, the amount of the solid dispersion, solid dosage form or pharmaceutical composition administered to a subject (either in a single dose or over multiple doses) is effective in one or more of inhibiting growth of glioblastoma cells, inhibiting metastasis of glioblastoma cells, killing glioblastoma cells, reducing tumor size, and reducing severity or incidence of symptoms associated with the presence of glioblastoma cells. The degree of one or more of these therapeutic effects may be about or more than about 10%, 20%, 30%, 40%, 50%, 60%, 70%, 80%, 90%, 95%, or more. In some embodiments, therapeutic efficacy is measured by an increased time in disease progression, such as between the appearance of one or more first symptoms, and the appearance of one or more second symptoms, or delay between two or more occurrences of the same symptoms. Delay may be about or more than about days, weeks, months, or years (e.g. 1, 2, 3, 4, 5, 6, 7, or more days; 1, 2, 3, 4, 5, 6, 7, 8, or more weeks; 1, 2, 3, 4, 5, 6, or more months; or 1, 2, 3, 4, 5, or more years). In the case of prevention, the subject may be an individual at risk of developing glioblastoma, such as a subject in remission, having a family history, and/or having some other predisposition. The degree of therapeutic efficacy may be with respect to a starting condition of the subject (e.g. the size of a tumor, rate of growth, rate of metastasis, severity or incidence of one or more symptoms), or with respect to a reference population (e.g. an untreated population, or a population treated with a different agent).

Efficacy in treating glioblastoma can be ascertained using any suitable method, such as those methods currently used in the clinic to track tumor size and cancer progress. Measuring tumor size is one way for determining whether growth has slowed, stopped, or been reversed (such as in the case of killing glioblastoma cells). Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

Desirably, the growth of a tumor is stabilized (i.e., one or more tumors do not increase more than 1%, 5%, 10%, 15%, or 20% in size, and/or do not metastasize) as a result of treatment. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment. When a tumor is subject to surgical resection following completion of the therapeutic period, the efficacy of the inventive method in reducing tumor size can be determined by measuring the percentage of resected tissue that is necrotic. In some embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable. In some embodiments, the growth rate of glioblastoma is reduced by about or more than about 10%, 20%, 30%, 40%, 50%, 60%, 70%, 80%, 90%, 95%, or more, including a complete halt in the growth of glioblastoma (e.g. in rate of change in the size of a tumor). In some embodiments, about or more than about 10%, 20%, 30%, 40%, 50%, 60%, 70%, 80%, 90%, 95%, or more of identified glioblastoma cells (e.g. as in a tumor mass) are killed.

A number of secondary parameters can be employed to determine therapeutic efficacy. Examples of secondary parameters include, but are not limited to, detection of new tumors, detection of tumor antigens or markers, biopsy, surgical downstaging (e.g. conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of glioblastoma markers that can be evaluated as indicators of therapeutic efficacy include, but are not limited to, ABCC3, GPNMB, NNMT, and SEC61γ (see e.g. U.S. Pat. No. 7,115,265).

A further example of a method for assessing treatment efficacy, the expression of biomarkers of a disease, e.g. glioblastoma, can be compared between a subject having or at risk of having the disease with the expression of the same biomarkers in the subject over time. In some cases, expression of the same set of biomarkers can be compared between a subject having or at risk of having a disease, and one or more normal subjects. In assessing disease outcome or the effect of treatment, a population of patients, all of which have a disease, may be followed for a period of time. Levels of biomarker expression may be established by assessing the expression of a biomarker in a sample from one patient, assessing the expression of additional samples from the same patient obtained later in time, and comparing the expression of the biomarker from the later samples with the initial sample or samples. This method may be used in the case of biomarkers that indicate, for example, progression or worsening of disease, lack of efficacy of a treatment regimen, remission of a disease, or efficacy of a treatment regimen. In addition, treatment efficacy in a subject can be evaluated by a variety of methods including, but not limited to, physical examination, biopsy, or any of a number of imaging technologies such as ultrasonography, computed tomography, magnetic resonance imaging, magnetic resonance spectroscopy, or positron emission tomography.

Glioblastoma is associated with a variety of symptoms. Common symptoms of the disease include seizure, nausea and vomiting, headache, memory loss, and hemiparesis, and progressive memory, personality, or neurological deficit due to temporal and frontal lobe involvement. In some cases, the tumor can start producing symptoms quickly, but occasionally is an asymptomatic condition until it reaches an enormous size. Therapeutic efficacy may be measured in terms of a reduction any one or more of these, such as in terms of frequency or severity. In some embodiments, reduction in symptoms is about or more than about 10%, 20%, 30%, 40%, 50%, 60%, 70%, 80%, 90%, 95%, or more, as measured using an appropriate scale.

With respect to quality of life assessments, such as the Clinical Benefit Response Criteria, the therapeutic benefit of treatment can be evidenced in terms of pain intensity, analgesic consumption, and/or the Karnofsky Performance Scale score. The Karnofsky Performance Scale allows patients to be classified according to their functional impairment. The Karnofsky Performance Scale is scored from 0-100. In general, a lower Karnofsky score is predictive of a poor prognosis for survival. In some embodiments, the treatment of glioblastoma in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

In one aspect, the present disclosure provides a method of treating an inflammatory disease of the digestive system in a subject in need thereof. In some embodiments, the method comprises administering to the subject an effective amount of a solid dispersion, solid dosage form or pharmaceutical composition provided herein. In one aspect, the present disclosure provides a method of reducing inflammation of the digestive system in a subject in need thereof, comprising administering to the subject an effective amount of a solid dispersion, solid dosage form or pharmaceutical composition provided herein. In some embodiments, the solid dispersion, solid dosage form or pharmaceutical composition is administered in an amount effective to delay progression of, reduce the incidence of, or reduce the degree of one or more characteristics associated with the inflammation or the inflammatory disease. In some embodiments, the solid dispersion, solid dosage form or pharmaceutical composition is administered, either in a single dose or over multiple doses, in an amount effective to induce remission of the inflammation or the inflammatory disease.

The digestive system consists of the gastrointestinal tract plus accessory organs of digestion, including the tongue, salivary glands, esophagus, stomach, pancreas, liver, gallbladder, small intestine, large intestine, colon, anus and rectum. Some embodiments of the present disclosure refer specifically to the lower gastrointestinal tract, including the small intestine and large intestine. The term "small intestine" encompasses the duodenum, jejunum and ileum, and the term "large intestine" includes the cecum, appendix, colon, ascending colon, right colic flexure, transverse colon, left colic flexure, descending colon, sigmoid colon, rectum, anal canal and anus.

The present disclosure provides both methods of reducing inflammation of the digestive system and methods of treating an inflammatory disease of the digestive system. As used herein, the term "inflammation" refers to the general term for local accumulation of fluids, plasma proteins, and/or white blood cells initiated by an autoimmune response, physical injury, infection, vascular disease, chemical exposure, radiation or a local immune response. Generally, inflammation is characterized by one or more signs, including, for example, redness, pain, heat, swelling and/or loss of function. Inflammation may be associated with chronic (long term) inflammatory diseases or disorders or acute (short term) inflammatory diseases or disorders.

In practicing any of the subject methods, the solid dispersion, solid dosage form or pharmaceutical composition may reduce inflammation of the digestive system, such as inflammation of one or more of the tongue, salivary glands, esophagus, stomach, pancreas, liver, gallbladder, small intestine, large intestine, colon, anus and rectum. In some embodiments, the solid dispersion, solid dosage form or pharmaceutical composition reduces inflammation of the lower gastrointestinal tract, such as inflammation of the small intestine, large intestine or colon. In some exemplary embodiments, the solid dispersion, solid dosage form or pharmaceutical composition reduces inflammation of the colon. The inflammation may be characterized as enteritis, gastritis, gastroenteritis, colitis, enterocolitis, duodenitis, jejunitis, ileitis, proctitis, or appendicitis. The inflammation may be acute or chronic. In some preferred embodiments, the inflammation is classified as colitis.

Under physiological conditions, the gastrointestinal tract can be characterized by a steep oxygen gradient. Chronic inflammatory bowel disease is typically characterized by an active consumption of $O_2$ by the recruited inflammatory cells including macrophages, dendritic cells and neutrophils. The resulting imbalance between oxygen consumption and supply renders the inflamed intestinal mucosa severely hypoxic. This "inflammatory hypoxia" typically leads to elevated levels of hypoxia inducible factors $1\alpha$ and $2\alpha$ (HIF-$1\alpha$ and HIF-$2\alpha$) in the intestinal epithelium of subjects suffering from inflammation of the digestive system, including subjects suffering from inflammatory bowel disease and in a murine model of colitis. In inflammatory bowel disease, HIF-$1\alpha$ and HIF-$2\alpha$ have been shown to play opposing roles in disease progression. Elevation of HIF-$1\alpha$ expression has been shown to be protective during inflammatory bowel disease, including for epithelial cell survival, induction of several barrier protective and tight junction proteins, increase in antimicrobial β-defensin and prevention of excessive immune response by upregulation of CD39/CD73 and T regulatory cells. HIF-$2\alpha$ chronic expression can lead to robust spontaneous intestinal inflammation and injury in inflammatory bowel disease including epithelial cell apoptosis, dysregulation of barrier protective and tight junction protein, increased pro-inflammatory cytokines and excessive immune response. HIF-2x has been shown to regulate recruitment and function of myeloid cells, including neutrophils and macrophages, facilitating the progression of inflammation and inflammation mediated colon cancer. Recently, HIF-$1\alpha$ was reported to be a driver of inflammation in a colitis model when knocked down in myeloid cell lineage cells.

Not wishing to be bound by any particular theory, the present inventors hypothesized that HIF-$2\alpha$ expression in colon epithelial and myeloid cells is a major driver of initiation, progression and maintenance of chronic inflammation. Blockade of HIF-$2\alpha$ is expected to reduce or inhibit recruitment of inflammatory cell types and also their pro-inflammatory products, leading to regression or prevention of inflammation of the digestive system, especially in subjects suffering from Crohn's disease and ulcerative colitis.

A subject exhibiting inflammation of the digestive system may suffer from inflammatory bowel disease, Crohn's disease, colitis, celiac disease, eosinophilic enteropathy or appendicitis. As used herein the term "inflammatory bowel disease" refers to a pathology characterized by an inflammatory condition of the colon and/or the small intestine. Crohn's disease and colitis are two types of inflammatory bowel disease.

In some embodiments, the inflammatory bowel disease comprises colitis, such as ulcerative colitis. "Colitis" is an inflammation of the colon. The colitis may be acute or chronic. As used herein, colitis includes ulcerative colitis, microscopic colitis, lymphocytic colitis, collagenous colitis, diversion colitis, chemical colitis, ischemic colitis, infections colitis, pancolitis, left-sided colitis, extensive colitis, segmental colitis, microscopic colitis, radiation-induced colitis, medication-induced colitis and proctitis. "Ulcerative colitis" is a chronic inflammatory disease affecting the colon. It is characterized by mucosal inflammation of the colon. Symptoms can range from mild to severe and may include blood in the stool, diarrhea, bloody diarrhea, rectal urgency, tenesmus, incontinence, fatigue, increased frequency of bowel movements, mucosal discharge, nocturnal defecations, abdominal discomfort, fever, weight loss, paradoxical constipation, anemia, and abdominal tenderness. Ulcerative colitis is an intermittent disease, with most patients having a relapsing and remitting disease course with periodic flares. The terms "flare" or "relapse" refer to an increase in symptoms of ulcerative colitis, for example increased stool frequency, increased rectal bleeding and/or appearance of abnormal mucosa evidenced by endoscopy. Although the symptoms of ulcerative colitis may diminish without intervention, the disease usually requires treatment to go into remission.

The term "active" ulcerative colitis as used herein refers to ulcerative colitis that is biologically active. Patients with active disease may be symptomatic and exhibit one or more sign or symptom of ulcerative colitis, for example, rectal bleeding, increased stool frequency, mucosal inflammation or abnormal laboratory tests (e.g., elevated ESR or CRP values or decreased hemoglobin). "Refractory" ulcerative colitis with respect to a particular therapy refers ulcerative colitis that is active or that relapses or flares in spite of being treated with that therapy.

As used herein, the term "Crohn's disease" refers to a type of inflammatory bowel disease characterized by inflammation of the lining of the gastrointestinal tract. Symptoms may include diarrhea, abdominal pain, fever, fatigue, bloody stool and weight loss.

When ulcerative colitis is suspected in a patient, the initial diagnosis generally is based on a combination of symptoms, endoscopic findings and histology. Diagnoses typically include stool samples, urinalysis, and tests for anemia, iron deficiency, leukocytosis and/or thrombocytosis. Markers of inflammation, such as erythrocyte sedimentation rate (ESR) and C-reactive protein, may be elevated, depending on the severity of the disease. However, endoscopy with biopsies is generally considered to be the only definitive method for establishing an ulcerative colitis diagnosis. Endoscopic findings that support a diagnosis of ulcerative colitis may include erythema, loss of normal vascular pattern, erosions, bleeding, granularity, friability, ulcerations, and pseudopolyps. Biopsies may also be taken at the time of endoscopy to differentiate ulcerative colitis from Crohn's disease. The biopsy samples are examined for distortion of crypt architecture, inflammation of the crypts, crypt shortening, increased lymphocytes and plasma cells in the lamina propria, crypt abscesses, mucin depletion, and hemorrhage or inflammation in the lamina propia.

The ulcerative colitis may affect part of the colon, or substantially the entire colon. The ulcerative colitis may be proctitis, where the ulcerative colitis is limited to the anus and lining of the rectum. The ulcerative colitis may be left-sided colitis, where the colitis is limited to the proportion of the colon distal to the splenic flexure, more particularly ulcerative colitis that extends from the rectum and as far proximally as the splenic flexure. The ulcerative colitis may be extensive colitis, wherein substantially the entire colon is affected. Accordingly, in some embodiments, the present disclosure provides a method of reducing inflammation in a subject suffering from ulcerative colitis, including proctitis, left-sided colitis, and extensive colitis.

Ulcerative colitis is generally further characterized by the severity of the disease, such as remission, mild, moderate or severe ulcerative colitis. The methods of the present disclosure may be applied to the treatment of mild, moderate or severe ulcerative colitis, or ulcerative colitis that is in remission. For example, an effective amount of a solid dispersion, solid dosage form or pharmaceutical composition provided herein may be administered to a subject suffering from mild ulcerative colitis. The solid dispersion, solid dosage form or pharmaceutical composition may be administered to a subject suffering from moderate ulcerative colitis. The solid dispersion, solid dosage form or pharmaceutical composition may be administered to a subject suffering from severe ulcerative colitis. The solid dispersion, solid dosage form or pharmaceutical composition may be administered to a subject suffering from mild or moderate ulcerative colitis. The solid dispersion, solid dosage form or pharmaceutical composition may be administered to a subject suffering from moderate or severe ulcerative colitis. The solid dispersion, solid dosage form or pharmaceutical composition may be administered to a subject suffering from ulcerative colitis that is in remission.

Numerous indices exist for assessing the severity of ulcerative colitis, including the Mayo score, Lichtiger score and Simple Clinical Colitis Activity Index. These indices typically factor in an endoscopy subscore, such as the subscore of the Mayo score or the Ulcerative Colitis Endoscopic Index of severity. Typical histological classifications include the Robarts Histopathology index and the Nancy index. A composite criteria may be used to assess the disease severity, incorporating one or more of these indices, the effect of the disease on the subject's quality of life, measurable markers of the disease activity and extent and the overall disease course, such as extraintestinal manifestations, intestinal damage and frequency of flares.

In some embodiments, a method described herein further comprises administering a second therapeutic agent. The second agent may be administered intravenously or subcutaneously. In some embodiments, the second agent is administered once or twice daily, once every other day, once every week, once every two weeks, or once every three weeks. The second agent may be administered in an amount of from about 1 to about 1000 mg, from about 5 to about 500 mg, from about 10 to about 350 mg, or from about 50 to about 200 mg. In one embodiment, the second active agent is administered orally and once or twice daily, once every other day, once every week, once every two weeks, or once every three weeks, in an amount of from about 1 to about 1000 mg, from about 5 to about 500 mg, from about 10 to about 350 mg, from about 10 to about 200 mg, from about 10 to about 100 mg, or from about 20 to about 50 mg. The specific amount of the second active agent will depend on the specific agent used, the type of disease being treated or managed, the severity and stage of disease, and the amount of the compound of Formula (I), and any optional additional active agents concurrently administered to the patient.

EXAMPLES

The following examples are given for the purpose of illustrating various embodiments of the invention and are not meant to limit the present disclosure in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Characterization Methods

X-Ray Powder Diffraction

XRPD was performed using a Bruker D2 Phaser X-ray diffractometer, with a scan type coupled θ/2θ, wherein the voltage is set to 30 kV and current is set to 10 mA at a rotation of 15 rpm held by a Zero-Background Cup, with slit width at 1.0 mm and knife-edge width set at 1.0 mm.

Modulated Differential Scanning Calorimetry

MDSC was performed using a TA Instruments Q2000 differential scanning calorimeter equipped with a TA instruments Refrigerated Cooling System 90. MDSC was used to measure glass transition temperature ($T_g$) and melting temperature ($T_m$), if present. The temperature range was adjusted from 0-250° C. with a heating rate of 1.5° C./min. The scanning mode was modulated where the modulation frequency was 60 seconds and modulation amplitude 1° C.

Gas Chromatography Head-Space

Residual solvent levels were determined using gas chromatography head space (GCHS) analysis. For example, an Agilent 6890A/7694 GC/HS instrument equipped with a 30 m×0.32 mm, 1.8 µm, JW Scientific DB-624 column was used to analyze a sample using the following method parameters: sample temperature, 105° C.; loop temperature, 110° C.; transfer line temperature, 115° C.; GC cycle time, 45 min; vial equilibrium time, 30 min; injection loop size, 1 mL; vial pressure time, 20 sec; carrier gas pressure, 7 psi; and vial pressure, 15 psi.

High Pressure Liquid Chromatography

HPLC was performed on an Agilent 1220 instrument equipped with a Kinetex, C18, 4.6×100 mm, 2.6 µm column using the following method parameters: mobile phase A, 0.1% formic acid in water; mobile phase B, 0.1% formic acid in acetonitrile; gradient 95% A (0 min), 60% A (6 min), 5% A (12 min), 95% A (15.1 min), with the balance made up with mobile phase B; flow rate, 0.8 mL/min; column temperature, 40° C.; sample temperature, room temperature; injection volume, 5 µL; detection wavelength, 240 nm; and run time, 18.5 min.

Scanning Electron Microscopy

SEM imaging was performed using a FEI Quanta 200 SEM with a Polaron Autocoater E5200 Au/Pd target sputter coater, with a voltage of 15 kV, spot size of 3.0 mA, filament current of 2.52 A, and an emission current of 96 µA.

Example 1: Characterization of 3-(((1S,2S,3R)-2,3-difluoro-1-hydroxy-7-(methylsulfonyl)-2,3-dihydro-1H-inden-4-yl)oxy)-5-fluorobenzonitrile The melting temperature ($T_m$) and glass transition temperature ($T_g$) of 3-(((1S,2S,3R)-2,3-difluoro-1-hydroxy-7-(methylsulfonyl)-2,3-dihydro-1H-inden-4-yl)oxy)-5-fluorobenzonitrile, the compound of Formula (I), were measured by mDSC and found to be 209.2° C. and 79.9° C., respectively. A diffraction pattern of the compound of Formula (I) was captured using XRPD (FIG. 1), indicating a crystalline material.

The solubility of the compound of Formula (I) was measured twice in acetone and acetone/H$_2$O mixtures. The first measurement was conducted at room temperature over 30 minutes with mixing completed by spinning in centrifuge tubes. The observed solubility is presented in Table 1.

TABLE 1

| Solvent | Solubility (wt. %) |
|---|---|
| 100% Acetone | 6.2 |
| 97.5/2.5% Acetone/H$_2$O | 7.3 |
| 95/5% Acetone/H$_2$O | 7.5 |
| 92.5/7.5% Acetone/H$_2$O | 6.7 |
| 90/10% Acetone/H$_2$O | 7.1 |
| 87.5/12.5% Acetone/H$_2$O | 5.8 |

The second measurement was completed to further evaluate acetone/H$_2$O combinations in 1% H$_2$O increments. The solubility presented in Table 2 was observed after allowing the samples to equilibrate for 48 hours at room temperature.

TABLE 2

| Solvent | Solubility (wt. %) |
|---|---|
| 100% Acetone | 6.0 |
| 99/1% Acetone/H2O | 6.0 |
| 98/2% Acetone/H2O | 6.6 |
| 97/3% Acetone/H2O | 6.7 |
| 96/4% Acetone/H2O | 6.3 |
| 95/5% Acetone/H2O | 6.6 |

Example 2: Solid Dispersion Screening

Seven polymer dispersion formulations comprising the compound of Formula (I) were prepared and spray dried from 95:5 Acetone: H$_2$O at a 25:75 ratio of the compound of Formula (I) to polymer according to the parameters provided in Table 3.

TABLE 3

| Parameter | Value |
|---|---|
| Spray Dryer | Buchi B290 |
| Cyclone | High Efficiency |
| Solvent | 95:5 Acetone:H$_2$O |
| Batch Size, Total Solids | 8.0 g |
| Solution Composition | 8% solids |
| Atomization Pressure | 26 psi |
| Solution Feed Rate | 13 ± 0.5 g/min |
| Inlet Temperature | 95° C. |
| Outlet Temperature | 40 ± 2° C. |
| Secondary Drying | ca. 26 h at 40° C. |

A secondary tray drying process was used to remove residual solvent after the initial spray drying. In this operation, the "wet" solid dispersion was heated to 40° C. and stored in a convection tray oven for 26 hours. The secondary stage treatment with elevated temperature removed residual acetone from the solid dispersion. Gas chromatograph (GC) headspace analysis was used to measure the residual solvent remaining in the solid dispersion after secondary drying. The residual acetone in several formulations was determined to be well below the 5000 ppm limit for acetone set forth by the International Conference on Harmonization (ICH). The overall yield, measured T$_g$, and residual acetone content of each of the solid dispersions are presented in Table 4.

TABLE 4

| Formulations | Dry Yield (%) | Measured Tg (° C.) | Residual acetone (ppm) |
|---|---|---|---|
| 25:75 compound of Formula (I):HPMCAS-M | 83 | 83.3 | <LOQ |
| 25:75 compound of Formula (I):HPMCAS-H | 84 | 85.4 | <LOQ |
| 25:75 compound of Formula (I):PVP-VA | 91 | 99.5 | 234 |
| 25:75 compound of Formula (I):HPMCP HP-55 | 91 | 102 | <LOQ |
| 25:75 compound of Formula (I):SOLUPLUS | 92 | 72.2 | <LOQ |
| 25:75 compound of Formula (I):CAP | 88 | 121.9 | 673 |
| 25:75 compound of Formula (I):Eudragit S100 | 86 | 134.2 | 7746 |
| 100% compound of Formula (I) | 73 | NA | Not tested |

LOQ: Limit of Quantification

Figure 2:
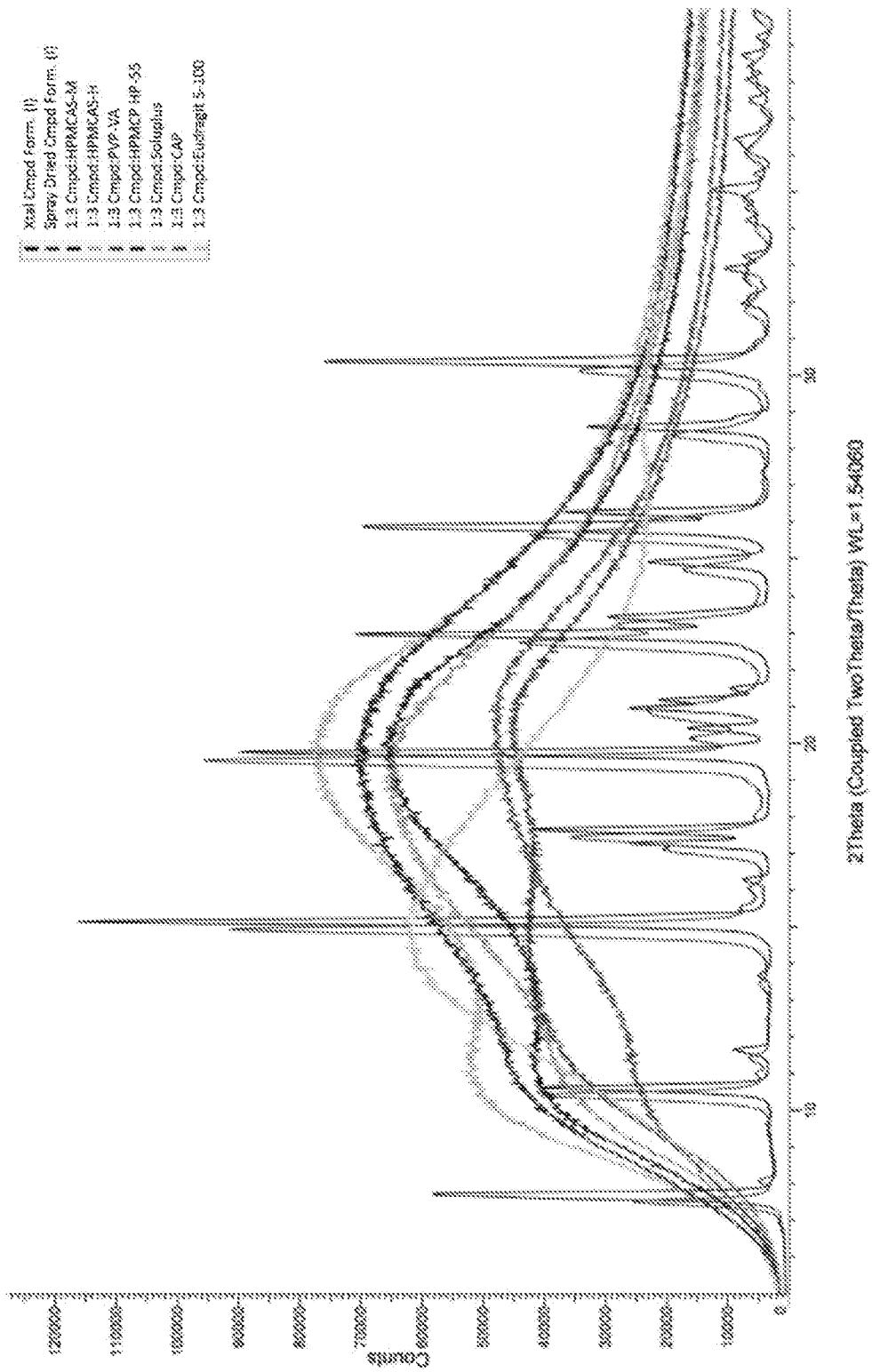
FIG. 2 depicts an overlay of diffractograms of seven solid dispersions of a compound of Formula (I), crystalline compound of Formula (I), and spray dried compound of Formula (I). The latter two diffractograms are characterized by sharp, distinct peaks.

Thermal analysis of the solid dispersions by mDSC showed that all of the dispersions had a single T$_g$, indicating an intimately mixed amorphous solid dispersion with good homogeneity. The T$_g$ values of the solid dispersions were between 70° C. and 140° C. (Table 4). These relatively high T$_g$ values are indicative of good physical stability, e.g. the propensity of the compound of Formula (I) to recrystallize during long-term storage is low. The solid dispersions were stored at temperatures below the T$_g$ to ensure long-term physical stability, so that the mobility of the compound of Formula (I) in the glass dispersion was low. The solution comprising 100% of the compound of Formula (I) in acetone was spray dried and recovered in crystalline form as evidenced by the lack of a T$_g$ and by the XRPD pattern. Characterization by XRPD indicated that the solid dispersions were consistent with amorphous structures due to the absence of observed crystalline peaks in the solid dispersion diffractograms (FIG. 2).

The surface morphology of the solid dispersions was assessed using SEM. The solid dispersions were observed to comprise whole and collapsed spheres with smooth surfaces. No crystalline material was observed in the solid dispersion samples.

The dissolution performance of the solid dispersions was tested in a non-sink dissolution test. The dissolution test was used to measure the supersaturation of drug above the bulk crystalline compound of Formula (I) solubility in biorelavent intestinal media (FaSSIF) after 30 minutes of exposure to a low-pH environment (SGF). During the test, samples were transferred from SGF [theoretical Cmax=2000 µgA/mL] to FaSSIF [theoretical Cmax=1000 µgA/mL].

The observed Cmax GB, Cmax FaSSIF, AUC FaSSIF, and AUC enhancement are provided in Table 5. The HPMCAS-H, CAP, and SOLUPLUS based solid dispersions provided approximately 30-fold enhancement of solubilized drug compared to bulk crystalline drug (AUC$_{solid\ dispersion}$/AUC$_{compound\ of\ Formula\ (I)}$) as shown in Table 5. All three solid dispersions provided a substantial increase in C$_{max}$, while concurrently maintaining supersaturation limits through at least 180 minutes of FaSSIF exposure. These three solid dispersions demonstrate good performance in the gastric transfer dissolution test and were expected to significantly enhance the bioavailability of the formula of Compound (I) relative to the bulk crystalline drug.

TABLE 5

| Formulations | Cmax GB (μgA/mL) | Cmax FaSSIF (μgA/mL) | AUC FaSSIF (μgA/mL*min) | AUC Enhancement |
|---|---|---|---|---|
| Crystalline compound of Formula (I) | 12 | 16 | 2600 | 1 |
| 25:75 compound of Formula (I):PVP-VA | 314 | 75 | 12700 | 4.9 |
| 25:75 compound of Formula (I):Eudragit S100 | 170 | 275 | 31000 | 11.9 |
| 25:75 compound of Formula (I):HPMCAS-M | 466 | 728 | 42500 | 16.3 |
| 25:75 compound of Formula (I):HPMCP HP-55 | 443 | 728 | 46200 | 17.8 |
| 25:75 compound of Formula (I):SOLUPLUS | 571 | 455 | 76700 | 29.5 |
| 25:75 compound of Formula (I):CAP | 249 | 841 | 77700 | 29.9 |
| 25:75 compound of Formula (I):HPMCAS-H | 409 | 545 | 90400 | 34.8 |

Example 3: Further Solid Dispersion Screening

Three solid dispersion formulations were manufactured for in vivo testing, comprising the compound of Formula (I) in a ratio to HPMCAS-H, CAP or SOLUPLUS of 25:75. All formulations were spray dried with similar parameters as used in Example 2. A secondary tray drying process was used to remove residual solvent after the initial spray drying. In this operation, the "wet" solid dispersion was heated to 40° C. and stored in a convection tray oven for 24 hours. The secondary stage treatment with elevated temperature removed residual acetone spray solvent from the solid dispersion material. Gas chromatograph headspace (GCHS) analysis was used to measure the residual solvent remaining in the solid dispersion material after secondary drying. The residual acetone in all three formulations was well below the 5000 ppm limit for acetone provided by the International Conference on Harmonization (ICH), with the HPMCAS-H and SOLUPLUS formulations being less than the LOQ of the test (<200 ppm). The CAP formulation was dried for an additional 24 h and determined to be <LOQ after retesting. Table 6 shows the residual solvent results for the two formulations. HPLC assay and purity analysis was performed post-secondary drying and confirmed that the manufacturing processes did not introduce any impurities or degrade the compound of Formula (I).

TABLE 6

| Formulations | Acetone (ppm) (24 h) | Acetone (ppm) (48 h) |
|---|---|---|
| 25:75 compound of Formula (I):HPMCAS-H | <LOQ | NA |
| 25:75 compound of Formula (I):CAP | 3489 | <LOQ |
| 25:75 compound of Formula (I):SOLUPLUS | <LOQ | NA |

LOQ: limit of Quantification

Cmax GB, Cmax FaSSIF, and AUC FaSSIF values were obtained and are reported in Table 7. The HPMCAS-H, CAP, and SOLUPLUS solid dispersions provided a 10 to 30-fold enhancement of solubilized drug compared to bulk crystalline drug ($AUC_{solid\ dispersion}/AUC_{compound\ of\ Formula\ (I)}$). All three solid dispersions provided a substantial increase in Cmax, while concurrently maintaining supersaturation limits through at least 180 minutes of FaSSIF exposure. These three solid dispersions demonstrated good performance in the gastric transfer dissolution test and were expected to significantly enhance the bioavailability of the compound of Formula (I) relative to the bulk crystalline drug.

TABLE 7

| Formulations | Cmax GB (μgA/mL) | Cmax FaSSIF (μgA/mL) | AUC FaSSIF (μgA/mL*min) | AUC Enhancement |
|---|---|---|---|---|
| 25:75 compound of Formula (I):HPMCAS-H | 292 | 403 | 65500 | 25.2 |
| 25:75 compound of Formula (I):CAP | 31 | 309 | 25300 | 9.7 |
| 25:75 compound of Formula (I):SOLUPLUS | 544 | 435 | 74300 | 28.6 |

Thermal analysis performed via mDSC revealed that all of the dispersions contained a single $T_g$, indicating an intimately mixed amorphous solid dispersion with good homogeneity. The relatively high $T_g$ values are indicative of good physical stability, e.g. the propensity of the compound of Formula (I) to recrystallize during long-term storage is low. The solid dispersions were stored at temperatures below the $T_g$ to ensure long-term physical stability, so that the mobility of the compound of Formula (I) in the glass dispersion was low.

Figure 3:
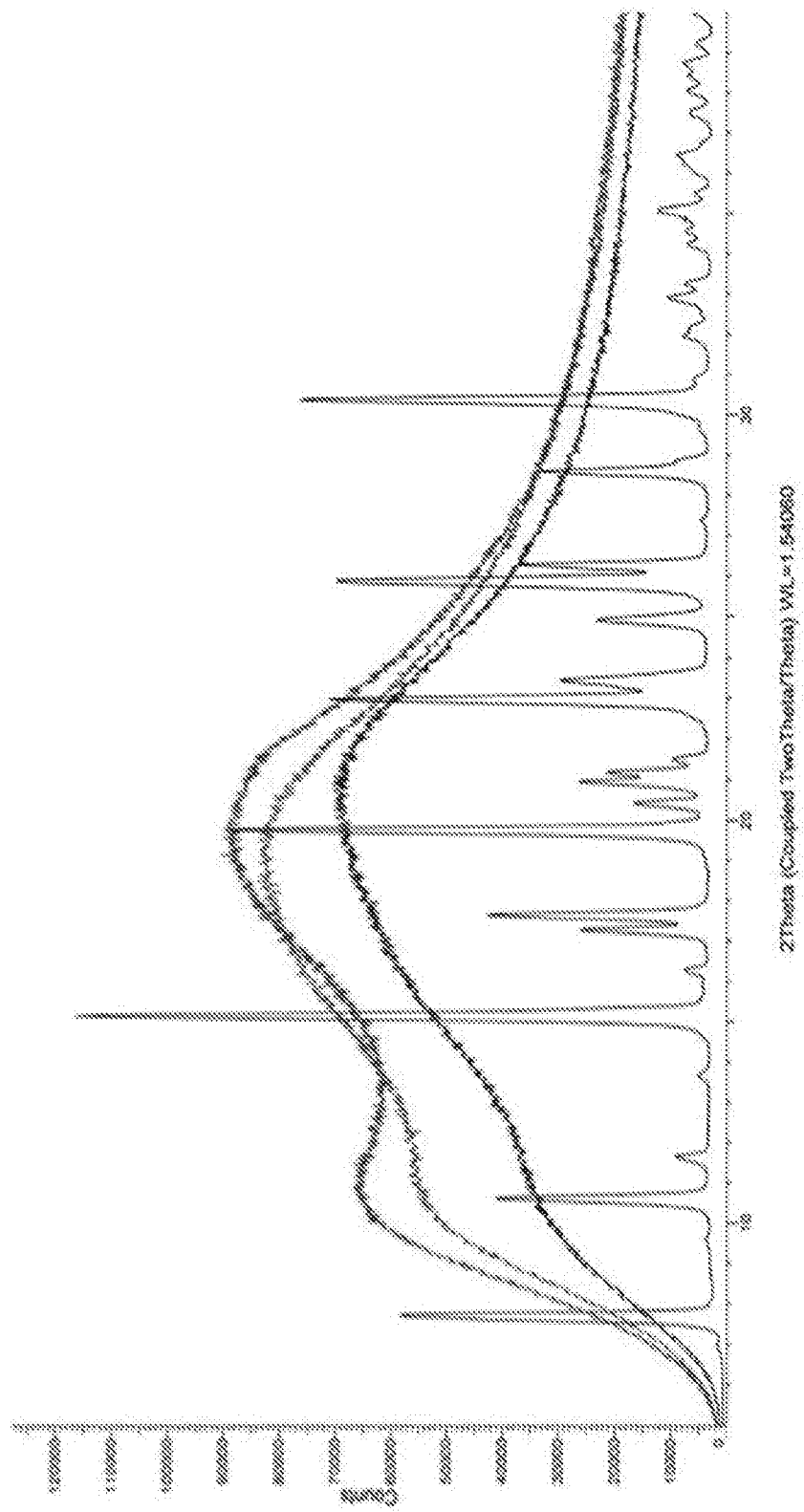
FIG. 3 depicts an overlay of diffractograms of three solid dispersions of a compound of Formula (I) and crystalline compound of Formula (I).

Solid state characterization by XRPD indicated that the solid dispersions were amorphous dispersions, as no crystalline peaks were observed in the solid dispersion diffractograms (FIG. 3).

Figure 4:
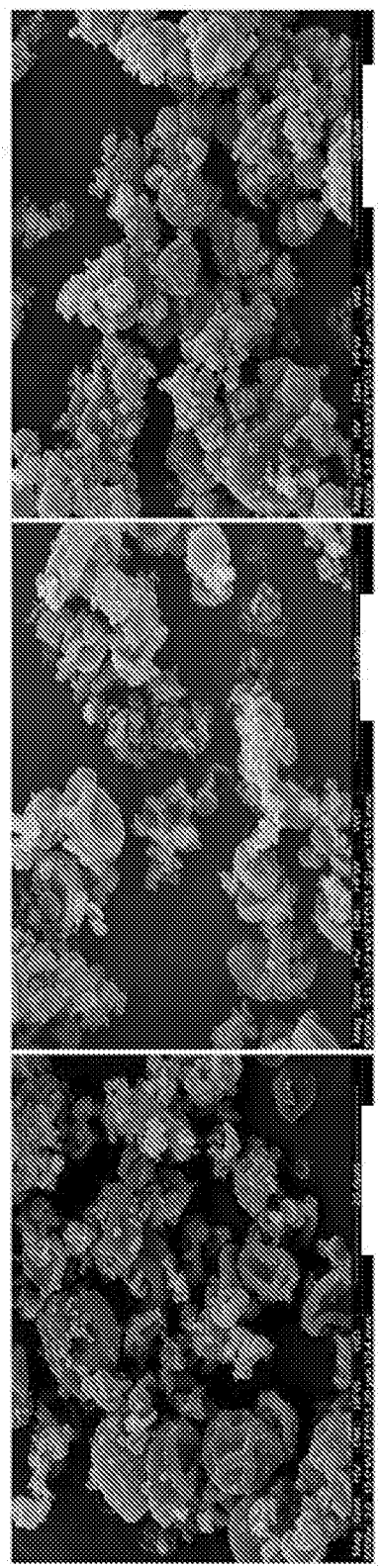
FIG. 4 provides SEM images of solid dispersions of the compound of Formula (I) and HPMCAS-H (left), CAP (middle) or SOLUPLUS (right) at 5,000× magnification.

Surface morphology of the solid dispersion particles was characterized using scanning electron microscopy. The SEM images (FIG. 4) depict solid dispersions of the compound of Formula (I) and, from left to right, HPMCAS-H, CAP or SOLUPLUS, at 5,000× magnification. The solid dispersions were observed to comprise whole and collapsed spheres with smooth surfaces. No crystalline material was observed in the solid dispersion samples.

Example 4: Suspension Dosing

Suspension stability of the solid dispersions was evaluated with suspension concentrations of 10 mg of the compound of Formula (I) per 1 mL in 1 wt. % of 1:1 methylcellulose: Tween 80 solution. The performance of each solid dispersion suspension was monitored at 4 and 24 hours after preparation using the SGF/FaSSIF dissolution test as the comparative metric.

Stable dissolution performance within 4 hours (when stored at room temperature ~21° C. with 750 rpm stirring) was observed for suspensions of the solid dispersion formulations prepared at 10 mgA/mL in a standard dosing vehicle, which would allow sufficient time for in vivo dosing following constitution of the suspensions. The suspension stability dissolution profiles for the solid dispersion formulations held for 4 hours or 24 hours can be found in Tables 8 and 9, respectively. The dissolution tests were dosed at 2.0 mgA/mL in SGF and upon transfer into FaSSIF were reduced to 1.0 mgA/mL. It is expected that the solid dispersion suspensions can be held for up to 4 hours prior to dosing.

40° C./75% RH, both open and in closed packaging with desiccant. The solid dispersions were evaluated for changes in amorphous physical state by XRPD, chemical purity by HPLC, and particle morphology by SEM.

Figure 5:
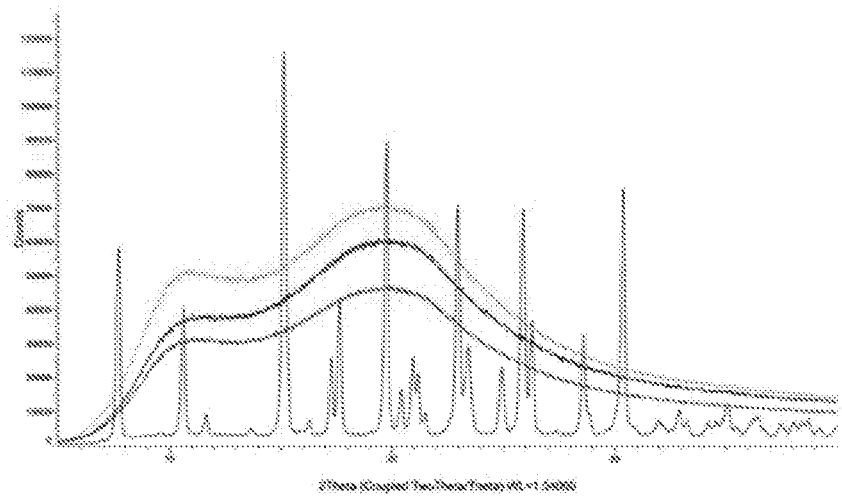
FIG. 5 depicts three sets of overlays of XRPD patterns of solid dispersions of the compound of Formula (I) and crystalline compound of Formula (I). In each set, the top broad curve represents a solid dispersion stored open for 4 weeks at 40° C. and 75% RH, the middle broad curve represents a solid dispersion stored closed for 4 weeks at the same conditions, and the bottom broad curve represents a solid dispersion prior to storage (t=0). The curve containing sharp, distinct peaks represents crystalline compound of Formula (I).
Figure 5:
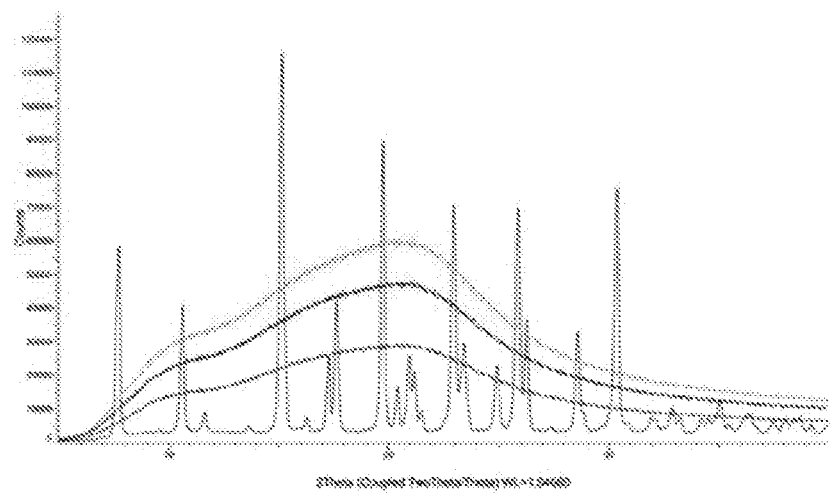
Figure 5:
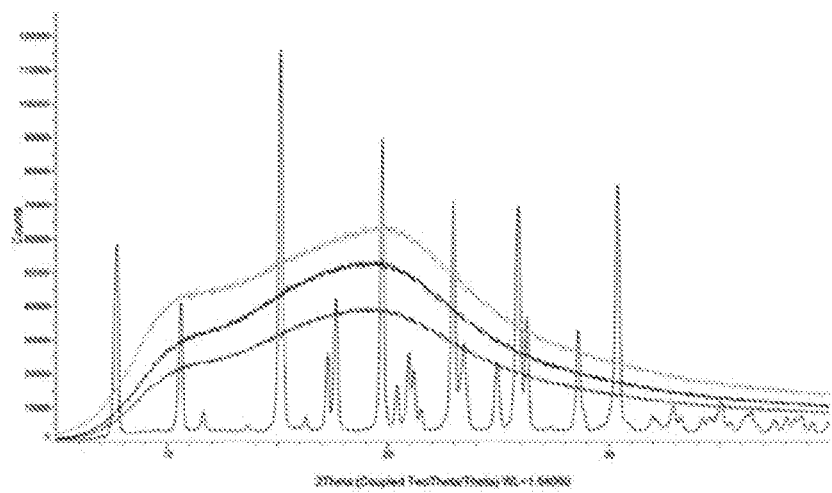

XRPD analysis of the aged solid dispersion samples showed that all solid dispersion formulations remained amorphous with no detectable crystalline material after 4 weeks, as shown in FIG. 5. The surface morphology of the aged solid dispersion particles was characterized using scanning electron microscopy. The SEM images revealed that the solid dispersions consisted of whole and collapsed spheres with smooth surfaces, except for the SOLUPLUS formulation at 40/75 open condition, which appeared as glassy agglomerated spheres but still amorphous as evidenced by XRPD. Purity analysis of the aged solid dispersions was performed on the HPMCAS-H and CAP formulations at two and four weeks at both 40/75 open and closed conditions. No substantial impurities were detected.

Example 6: Lipidic Vehicle Formulations

Five formulations of the compound of Formula (I) and lipid vehicles were prepared. Size 0 gelatin capsules were filled with the formulations at 60° C. Each capsule had a total weight of 500±50 mg and contained 5.0±0.3 wt. % of the compound of Formula (I) and approximately 95 wt. % of a lipid vehicle selected from: (1) 1:4 TPGS-1000: Gelucire 44/14; (2) 2:3 TPGS-1000: Gelucire 44/14; (3) 1:4 TPGS-1000: Gelucire 50/13; (4) 2:3 TPGS-1000: Gelucire 50/13; and (5) 1:1:1 TPGS-1000: Gelucire 44/14: Gelucire 50/13.

TABLE 8

| Formulations | Cmax GB (μgA/mL) | Cmax FaSSIF (μgA/mL) | AUC FaSSIF (μgA/mL*min) | AUC Enhancement |
|---|---|---|---|---|
| Xtal compound of Formula (I) | 18.3 | 15.5 | 2600 | 1.0 |
| 25:75 compound of Formula (I):HPMCAS-H | 83.2 | 176.6 | 29700 | 11.4 |
| 25:75 compound of Formula (I):CAP | 106.0 | 258.5 | 25700 | 9.9 |
| 25:75 compound of Formula (I):SOLUPLUS | 429.9 | 147.8 | 23400 | 9.0 |

TABLE 9

| Formulations | Cmax GB (μgA/mL) | Cmax FaSSIF (μgA/mL) | AUC FaSSIF (μgA/mL*min) | AUC Enhancement |
|---|---|---|---|---|
| Xtal compound of Formula (I) | 35.8 | 33.0 | 5600 | 1.0 |
| 25:75 compound of Formula (I):HPMCAS-H | 66.6 | 101.3 | 17100 | 3.1 |
| 25:75 compound of Formula (I):CAP | 56.3 | 142.7 | 20800 | 3.7 |
| 25:75 compound of Formula (I):SOLUPLUS | 107.5 | 64.7 | 11100 | 2.0 |

Example 5: Stability of Solid Dispersions

To rapidly assess the physical and chemical stability of solid dispersion formulations of the compound of Formula (I), dispersions were aged for 4 weeks at 25° C./60% RH and Cmax GB, Cmax FaSSIF, and AUC FaSSIF values were calculated for each formulation and are reported in Table 10. The 2:3 TPGS-1000: Gelucire 44/14 based formulation provided a 4 fold enhancement of solubilized drug compared to bulk crystalline drug.

TABLE 10

| Formulations | Cmax GB (μgA/mL) | Cmax FaSSIF (μgA/mL) | AUC FaSSIF (μgA/mL*min) | AUC Enhancement |
|---|---|---|---|---|
| Xtal compound of Formula (I) | 14 | 19 | 3021 | 1.0 |
| 1:4 TPGS-1000:Gelucire 44/14 | 39 | 35 | 5713 | 1.9 |
| 2:3 TPGS-1000:Gelucire 44/14 | 125 | 83 | 12004 | 4.0 |
| 1:4 TPGS-1000:Gelucire 50/13 | 14 | 27 | 4016 | 1.3 |
| 2:3 TPGS-1000:Gelucire 50/13 | 10 | 31 | 4049 | 1.3 |
| 1:1:1 TPGS-1000:Gelucire 44/14:Gelucire 50/13 | 21 | 39 | 5721 | 1.9 |

Approximately 35 capsules containing 25 mgA (25 mg of the compound of Formula (I)) in 2:3 TPGS-1000: Gelucire 44/14 were manufactured for in vivo and accelerated stability testing. HPLC assay and purity analysis were performed. No degradation of the compound of Formula (I) was observed with or without capsule excipients.

The lipid capsules were aged for 4 weeks at 25° C./60% RH (closed) and at 40° C./75% RH (open or in closed packaging). The lipid capsules were evaluated for changes in chemical purity by HPLC. Purity analysis of the aged lipid capsules was performed at two and four weeks at both 40/75 open and closed conditions, with and without capsule excipients. No compound of Formula (I)-related degradation was observed after four weeks at either condition. The peak due to gelatin grew from 0.30% total peak area to 0.9-1.3% total peak area after four weeks for all configurations, although the peak related to TPGS-1000 at remained static throughout the study.

Example 7: Solid Dispersions with HPMCAS-H

A 75 L tank with a pneumatic agitator was charged with acetone (23.0 kg) followed by the compound of Formula (I) (0.5 kg). The resulting suspension was mixed for 6 minutes at room temperature, at which point a clear solution was obtained, indicating that all of the compound of Formula (I) had dissolved. HPMCAS-H polymer (1.5 kg) was then added, and the resulting solution was mixed for 14 hours at room temperature. Acetone was removed by spray drying the solution using an SPX Anhydro MicraSpray MS-150 spray drying unit equipped with a 2-fluid nozzle. The spraying was completed in a closed loop configuration using the following parameters: nozzle, Spray Systems 2-fluid; solvent, acetone; total solids, 2.0 kg; solution composition, 8% solids; total solution weight, 25.0 kg; atomization pressure, 2.5-2.8 bar; spray rate, 10.0 kg/hr; inlet temperature, 74.9-77.0° C.; outlet temperature, 42.0-42.9° C.; drying gas flow rate, 174 kg/hr; condenser temperature, −17.6 to −17.1° C.

Secondary drying was completed in a Despatch 4 ft$^3$ tray dryer to remove residual acetone remaining after spray drying. The bed depth of the solid dispersion was approximately 1" on the trays and the dryer temperature set point was 40° C. The solid dispersion was found to show rapid removal of acetone at 40° C. and drying was complete close to 5 hours after being loaded in the drier. The dried solid dispersion met the 5000 ppm ICH Option 1 limit for acetone.

After completion of the spray drying, it was observed that the solid dispersion contained static. As a result, there was some accumulation of solid dispersion in the MS-150 drying chamber, although the material was still loose and did not agglomerate together. The overall yield was only 64%, likely due to hold-up in the chamber. Minimal (~100 g) solid dispersion was observed within the bag house, build up (~400 g) on the main chamber walls was seen, and moderate build up (~25 g) on the outlet processing pipe was observed.

Hold times for both the spray solution and the wet solid dispersion prior to secondary drying were assessed. The total impurities observed by HPLC for the held spray solution and the held wet solid dispersion are reported in Table 11. Both the spray solution and wet solid dispersion were held at room temperature for the time indicated in the table. The spray solution stability data showed an approximate growth of impurities at 0.05% per day. The wet solid dispersion stability data showed an approximate growth of impurities at 0.02% per day.

TABLE 11

| Hold Time | Total Impurities (%) in Spray Solution | Total Impurities (%) in Wet Solid Dispersion |
|---|---|---|
| T0 | 1.24 | 1.24 |
| 1 Day | 1.30 | 1.31 |
| 3 Days | 1.48 | 1.31 |
| 7 Days | 1.60 | 1.41 |

Figure 6:
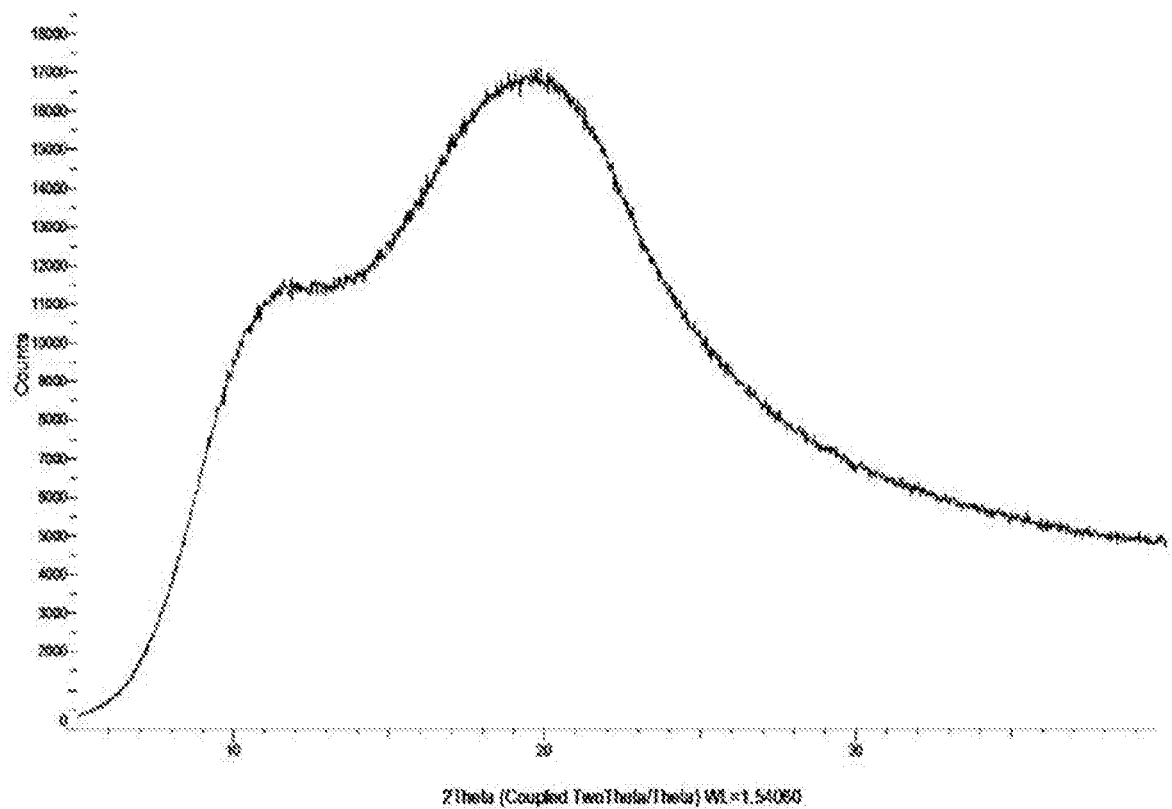
FIG. 6 depicts an XRPD pattern of a 1:3 compound of Formula (I): HPMCAS-H solid dispersion.

The dried solid dispersion was characterized by XRPD, mDSC, SEM, KF, residual solvent, particle size, bulk/tapped density, and HPLC (chiral and achiral). FIG. 6 shows the XRPD pattern of the solid dispersion. The diffraction pattern is absent of crystalline peaks and shows that the solid dispersion is amorphous in nature. Measurement of the weight percent water and residual solvent showed that the solid dispersion contained 0.75 weight percent H$_2$O by KF and that the residual acetone was less than the LOQ (<200 ppm).

Figure 7:
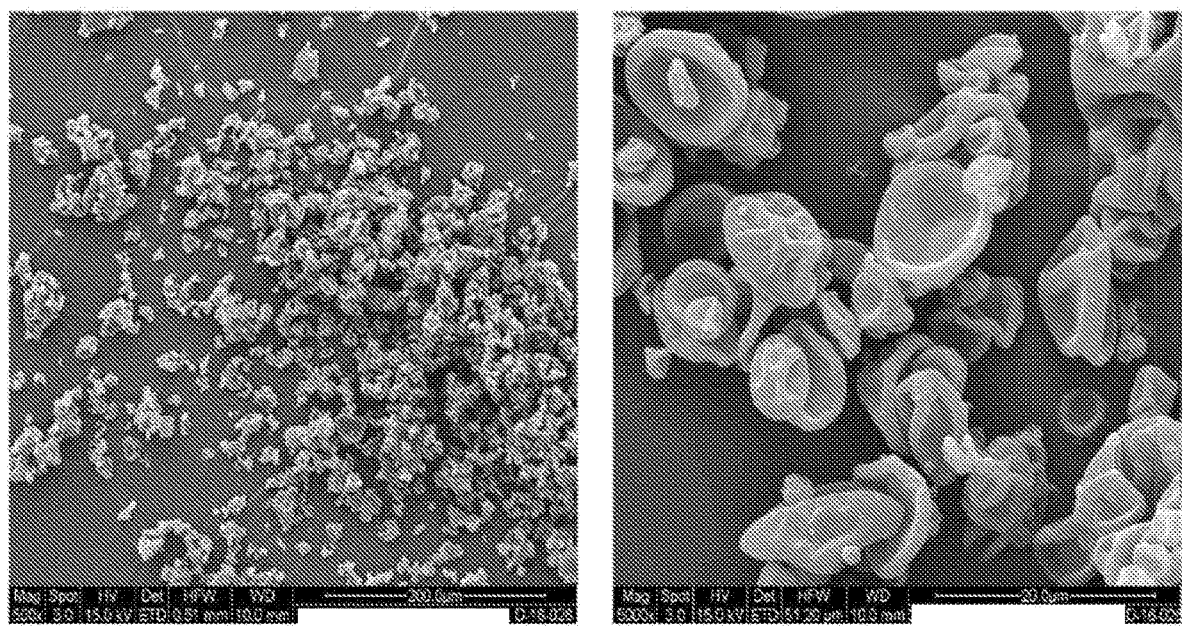
FIG. 7 provides SEM images of a 1:3 compound of Formula (I): HPMCAS-H solid dispersion at 500× (left) and 5,000× (right) magnification.

The glass transition temperature of the solid dispersion was measured by mDSC. The data show that the T$_g$ is approximately 86° C. Only a single thermal event (T$_g$) was observed, suggesting a homogenous glassy solution was obtained from the spray drying process. SEM analysis (FIG. 7) showed that the solid dispersion morphology consisted of whole and collapsed spheres with smooth surfaces at 500× (left) and 5,000× (right) magnification. No crystalline material was observed in the sample.

Figure 8:
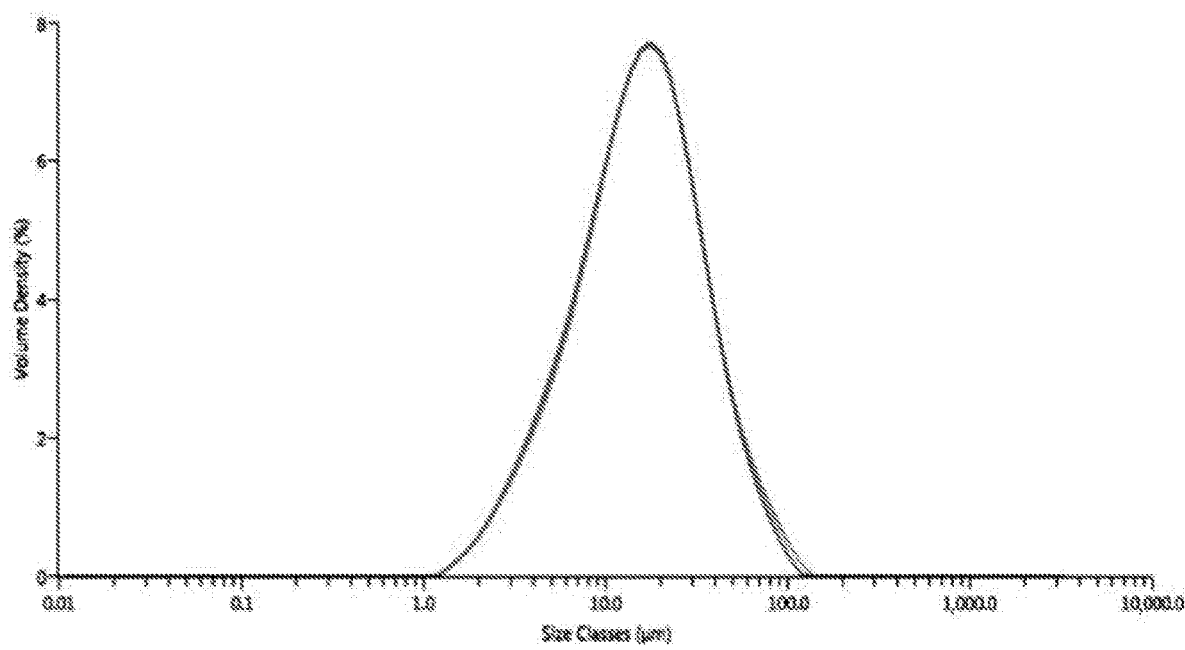
FIG. 8 shows the particle size distribution of a solid dispersion.

As shown in FIG. 8, laser light scattering was performed on the solid dispersion powder to determine the particle size distribution. A Malvern Aero S dry particle size analyzer was used with a 3 mm hopper height at 0.7 bar pressure with a feed rate of 40%. Samples were analyzed over the course of 10 seconds in triplicate. A refractive index of 1.681 and a density of 0.5 g/mL were used for analysis with a non-spherical algorithm. The sample obscuration was between 0.1 and 15%. The particle size measurement showed that the solid dispersion exhibited a monomodal distribution and determined that the average $d_{10}$ was 4.9 µm, the average $d_{50}$ was 15.6 µm, and the average $d_{90}$ was 41.5 µm.

The bulk and tapped densities were also measured. The bulk density was found to be 0.25 g/mL and the tapped density to be 0.41 g/mL. The flowability was calculated as Carrs Index 44.35 and Hausner Ratio of 1.80.

Figure 9:
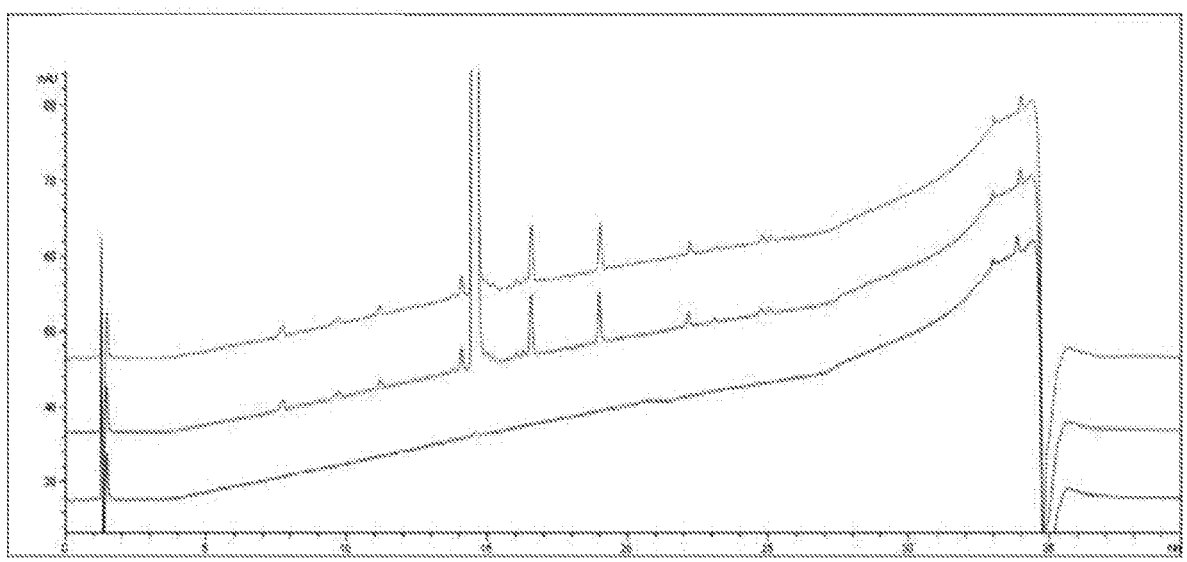
FIG. 9 depicts HPLC traces of a blank (bottom trace), compound of Formula (I) (middle trace), and a solid dispersion of a compound of Formula (I) and HPMCAS-H (top trace).

The solid dispersion was analyzed by HPLC and found to contain 24.6% of the compound of Formula (I). Chromatographs of the solid dispersion (top line), the compound of Formula (I) (middle line), and a blank (bottom line) are shown in FIG. 9. The compound of Formula (I) and the solid dispersion showed minimal differences in impurities by HPLC. Chiral purity analysis was also completed on the solid dispersion, which showed 99.8% enantiomer excess of the compound of Formula (I).

Figure 10:
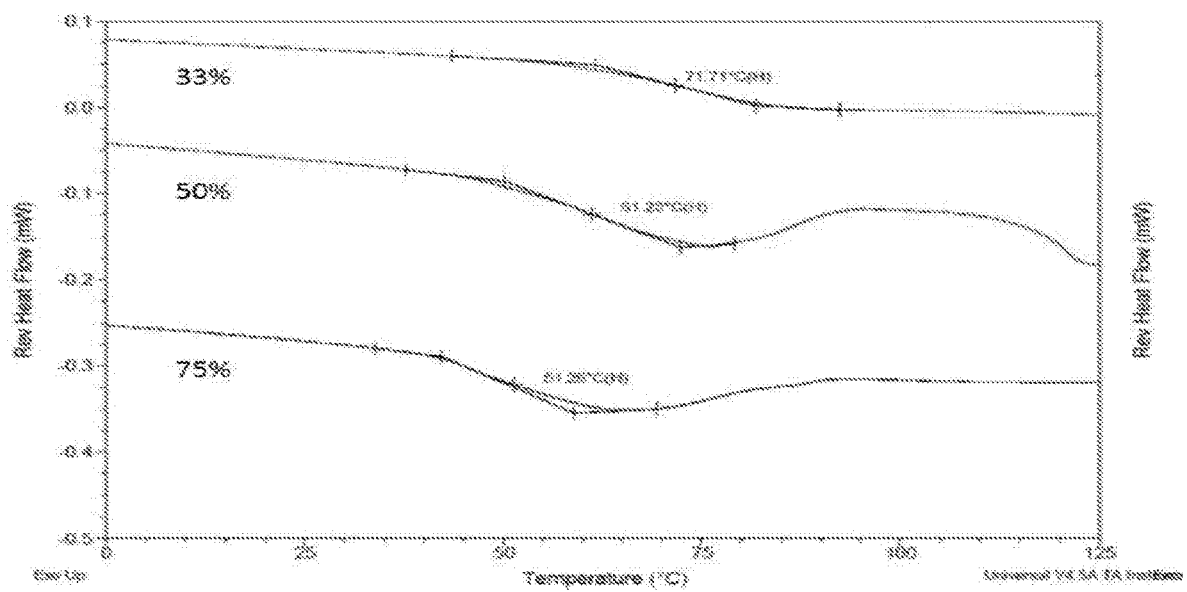
FIG. 10 depicts mDSC profiles of a 1:3 compound of Formula (I): HPMCAS-H solid dispersion after 24 hours of exposure to 33% humidity (top curve), 50% humidity (middle curve) or 75% humidity (bottom curve).

The effect of relative humidity on the $T_g$ was examined for the solid dispersion. The solid dispersion was exposed to humidity levels of 33%, 50% or 75% for 24 hours. Following exposure, the samples were capped in hermetically sealed DSC pans for analysis. The thermograms of each sample are shown in FIG. 10. The dispersions showed a drop in $T_g$ as RH is increased, likely due to the hygroscopic nature of the material. As shown, the $T_g$ dropped to 71° C. and 51° C. when exposed to 33% and 75% RH, respectively. The impact of humidity (water content) on the glass transition temperature of the solid dispersion suggests that molecular mobility is theoretically possible at room temperature (25° C.) when the humidity is >33%, which could allow the compound of Formula (I) to nucleate and crystallize accordingly. The solid dispersion was packaged in packaging that maintains RH values <33% for long-term storage.

Water adsorption of the solid dispersion was determined using dynamic vapor sorption (DVS). The dispersions were subjected to ramping humidity from 5-95% RH and subsequently exposed to decreasing humidity from 95-5% RH to determine the adsorption/desorption of water. DVS results indicate that the solid dispersion is moderately non-hygroscopic and adsorbs up to 5.5 wt. % $H_2O$ at 90% RH.

A sample of the hold-up material collected from the spray dryer chamber was analyzed by SEM for particle morphology, XRPD for amorphous character, and HPLC for impurities. All testing showed equivalency between the hold-up chamber material and the collected solid dispersion, demonstrating that the hold-up chamber material and collected solid dispersion could be combined.

The solid dispersion was packaged in double LDPE bags and placed in a HDPE drum. 2 gram lots of the solid dispersion were packaged in double LDPE bags, each goose necked and sealed with a cable tie. The bagged samples were stored in 75 cc HDPE bottles sealed with a screw cap enclosure. The stability of the packaged solid dispersions was then tested under ICH conditions. No meaningful change in appearance, assay, related substances, amorphous character or thermal analysis was observed after three months of storage at 2-8° C., 25° C./60% RH, or 40° C./75% RH. At 40° C./75% RH, the moisture increased from 0.75% at T0 to 2.42% at 3 months. The addition of desiccant to the packaging is expected to prevent this increase in moisture. The stability data collected for the solid dispersions are summarized in Table 12.

TABLE 12

| Test | T = 0 | T = 3 months 2-8° C. | T = 3 months 25° C., 60% RH | T = 3 months 40° C., 75% RH |
|---|---|---|---|---|
| Appearance | White powder | Off-white powder | White powder | White powder |
| Compound of Formula (I) (HPLC) | 24.6 wt % | 24.3 wt % | 24.6 wt % | 24.6 wt % |
| Total Impurities (HPLC) | 1.24% | 1.42% | 1.52% | 1.42% |
| Chiral Purity (HPLC) | 99.8% | >99.8% | >99.8% | >99.8% |
| Crystallinity (XRPD) | Consistent with amorphous form | Consistent with amorphous form | Consistent with amorphous form | Consistent with amorphous form |
| $T_g$ (DSC) | 86.2 ± 0.9° C. | 85.40° C. | 85.06° C. | 86.00° C. |
| Water Content (KF) | 0.75% | 1.16% | 1.26% | 2.42% |

Example 8: Preparation of Solid Dispersions

The compound of Formula (I) (2.25 kg) was mixed with acetone (103.5 kg) for 15 minutes at room temperature until a clear solution was obtained. HPMCAS-H polymer (6.75 kg) was added and the resulting mixture was mixed for 8 hours and held at ambient conditions overnight. The resultant solution was spray dried using an Anhydro MS-150 spray dryer equipped with a Spray Systems 2-fluid nozzle. The following spray parameters were used and monitored throughout the course of spray drying: inlet temperature, 76.0±20.0° C.; outlet temperature, 42.0±5.0° C.; chiller set point, −30.0° C.; condenser temperature, −17.0±10.0° C.; solution feed rate, 10.0±2.0 kg/hr; drying gas flow rate, 170.0±20.0 kg/hr; atomization pressure, 2.5±0.5 bar; chamber pressure, 34 cmWC; cyclone ΔP, 150 mmWC; and bag house ΔP, 70 mmWC. After spray drying, the solid dispersion was loaded onto trays and dried at 40° C. for approximately 14 hours. A total of 8.2 kg of dry solid dispersion was recovered, 1.3 kg of which was from chamber collection, for an overall yield of 92%. The solid dispersion was packaged in double 4-mil LDPE bags with twenty 5 gram silica gel desiccant packets placed between bags, then placed in a 15 gal HDPE drum and stored at 2-8° C.

The solid dispersion was packaged in 2 gram batches in double LDPE bags, each goose necked and sealed with a cable tie with 0.5 grams of desiccant added between the LDPE bags. Each sample was stored in 75 cc HDPE bottles, sealed with a screw cap enclosure. Samples were stored for three months at either 2-8° C., 25° C. and 25% relative humidity, or 40° C. and 75% relative humidity, then characterized to assess the stability of the solid dispersion. No significant change, other than a slight increase in KF, was observed under any condition from time zero. No crystallization was observed by XRPD analysis.

This batch of the solid dispersion was characterized against approved specifications. The analysis included appearance, HPLC purity, chiral HPLC purity, KF, residual solvent, XRPD, and mDSC are tabulated in Table 13.

TABLE 13

| Test | T = 0 | T = 3 months 2-8° C. | T = 3 months 25° C., 60% RH | T = 3 months 40° C., 75% RH |
|---|---|---|---|---|
| Appearance (Visual) | White powder | White powder | White powder | White powder |
| Compound of Formula (I) (HPLC) | 25.1 wt % | 24.8 wt % | 24.6 wt % | 24.7 wt % |
| Total Impurities (HPLC) | 1.02% area | 1.08% area | 1.03% area | 1.06% area |
| Crystallinity (XRPD) | Consistent with amorphous form | Consistent with amorphous form | Consistent with amorphous form | Consistent with amorphous form |
| Average $T_g$ (mDSC) | 87.58° C. | 87.91° C. | 89.37° C. | 87.49° C. |
| Water Content (KF) | 1.11 wt % | 0.71 wt % | 0.86 wt % | 1.26 wt % |
| Chiral Purity (HPLC) | >99.8% | | | |
| Residual Acetone (GC) | <200 ppm | | | |

Example 9: Evaluation of Solids Loading in Spray Drying

The solution viscosity and precipitation behavior of formulations of the compound of Formula (I) and HPMCAS-H in various solvent compositions were assessed. As shown in Table 14, the viscosity in acetone was found to increase with increasing solids load. The 97:3 acetone/H$_2$O solution showed similar viscosity as neat acetone at 14 wt. % solids loading. These values indicate that each of these formulations could be as spray solutions with standard solution pumps.

TABLE 14

| Formulation | Solvent | Solids Loading (Wt. %) | Viscosity (cP) |
|---|---|---|---|
| 13 compound of Formula (I)/HPMCAS-H | 100% Acetone | 12 | 20 |
| | 100% Acetone | 14 | 33 |
| | 97:3 Acetone/H$_2$O | 12 | 27 |

Precipitation behavior of the three solutions was evaluated visually. No precipitation of the compound of Formula (I) or polymer was observed after three days at room temperature. The spray solution looked slightly hazy after three days due to HPMCAS-H and the viscosity increase as the polymer dissolved.

The compound of Formula (I) was formulated in a 1:3 ratio (i.e., 25% drug load) with hypromellose acetate succinate HG grade (HPMCAS-H). Spray drying was completed at a 100 g scale using 12 wt. % solids loading in 97/3 acetone/H$_2$O and secondary drying was completed using a tray convection dryer. Characterization of the solid dispersion was done using XRPD, SEM, mSDC, GC-HS, achiral HPLC and particle size measurement. In addition, the spray solution stability and wet solid dispersion stability were also evaluated.

A flask with a magnetic stirrer was charged with 97/3 acetone/H$_2$O (733.3 g) followed by the compound of Formula (I) (25 g). A clear solution was obtained after mixing at room temperature, indicating that the compound of Formula (I) had dissolved. HPMCAS-H polymer (75 g) was then added to the solution and mixed at room temperature until a clear solution was obtained.

Spray drying to remove the acetone/H$_2$O solvent and provide the amorphous solid dispersion was completed on a Buchi B-290 spray drying unit equipped with a 2-fluid nozzle. The spraying was completed in a recycle configuration with a high efficiency cyclone.

The wet solid dispersion yield was found to be 93% (not accounting for solution samples taken for stability analysis). Secondary drying was completed in a tray dryer to remove residual acetone and water remaining after spray drying. The dryer temperature set point was 40° C. and the solid dispersion was dried for 24 hours. A dry solid dispersion yield of 79% was obtained after drying, which does not account for samples taken for residual solvent analysis.

The solid dispersion showed rapid removal of acetone at 40° C. Drying was complete close to 5 hours after being loaded in the drier. The solid dispersion met the 5000 ppm ICH Option 1 limit for acetone. The water content was found to be 0.74 wt % after the 24-hour drying period.

Additional information about the solid dispersion was collected during the spray drying to establish hold times for both the spray solution and the wet solid dispersion prior to secondary drying. Table 15 shows the HPLC total impurities in the spray solution and the wet solid dispersion after being held at room temperature for 7 days. The wet solid dispersion contained ~21,000 ppm acetone.

TABLE 15

| Hold Time | Total Impurities (%) in Spray Solution | Total Impurities (%) in Wet Solid Dispersion | Average $T_g$ (° C.) of Wet Solid Dispersion |
|---|---|---|---|
| T0 | 0.93 | 0.93 | n.d. |
| 1 Day | 0.91 | 0.92 | 59.3 |
| 3 Days | 0.92 | 0.91 | 59.2 |
| 5 Days | n.d. | 0.85 | 58.4 |
| 7 Days | 0.92 | 0.91 | 61.7 |

The spray solution stability data showed no change in impurities. From this data, it was determined that the acetone/H$_2$O spray solution could be used (i.e. spray dried) seven (7) days after preparation when held at room temperature. The wet solid dispersion stability data showed no growth of impurities over seven (7) days. From this data, it was determined that the wet solid dispersion could be held for several days at room temperature if needed.

Figure 11:
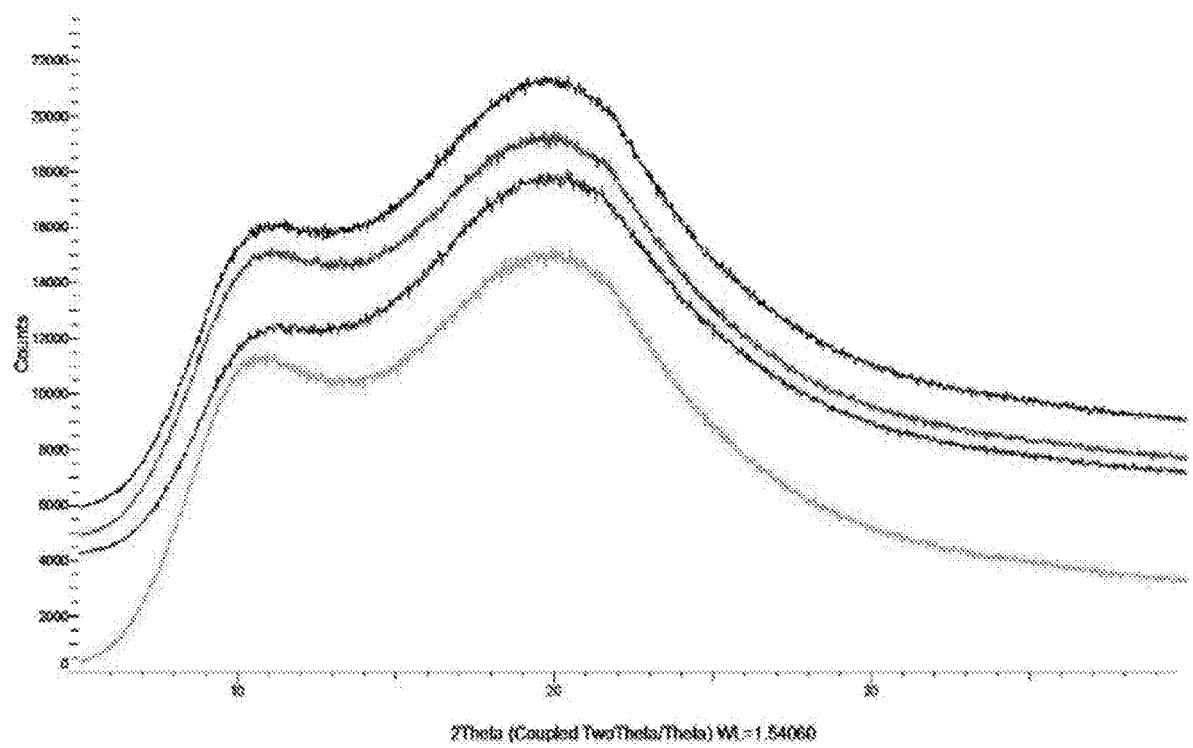
FIG. 11 provides XRPD patterns of wet solid dispersions held at room temperature for 1 day, 3 days, 5 days, or 7 days (top to bottom curves, respectively).

The wet solid dispersion was also evaluated for crystallization by XRPD and mDSC analysis. FIG. 11 shows the XRPD pattern of the solid dispersion over the course of seven days at room temperature. As evidenced by the XRPD pattern, the wet solid dispersion remained amorphous after 7 days of storage with no evidence of crystallization. As reported in Table 15, the T$_g$ was found to range from 58-62° C. over the hold period and no crystallization events were observed.

Figure 12:
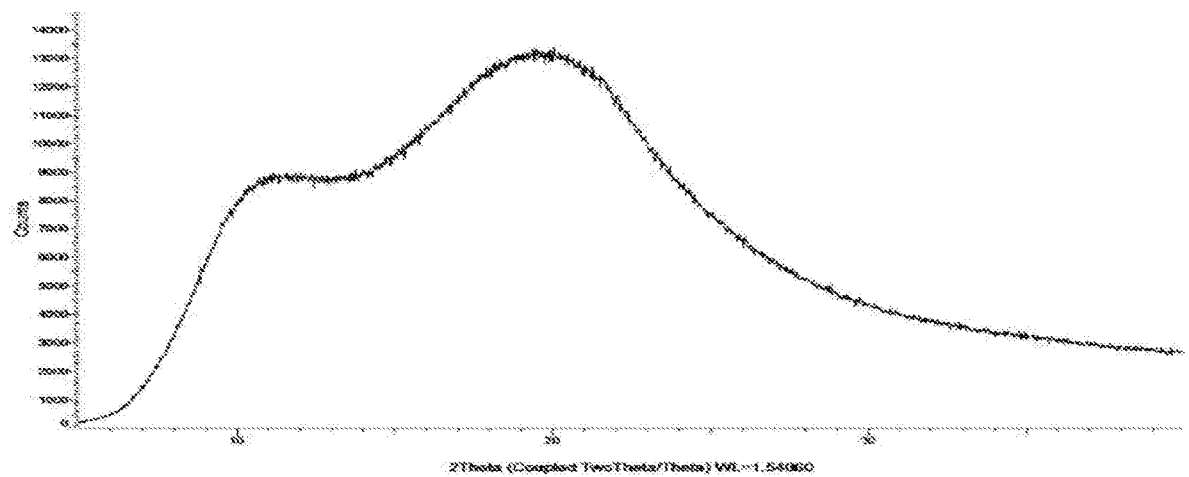
FIG. 12 provides an XRPD pattern of a 1:3 compound of Formula (I): HPMCAS-H solid dispersion.

The dried solid dispersion was characterized by XRPD, mDSC, SEM, KF, residual solvent, particle size, and achiral HPLC. FIG. 12 shows the XRPD pattern for the solid dispersion. The diffraction pattern is absent of crystalline peaks and therefore shows the solid dispersion is amorphous in nature.

Measurement of the weight percent water and residual solvent showed that the solid dispersion contained 0.75 weight percent H$_2$O by KF and that the residual acetone was less than the LOQ (<200 ppm).

The T$_g$ of the solid dispersion was found to be approximately 84° C. by mDSC. Only a single thermal event was observed, suggesting that a homogenous glassy solution was obtained from the spray drying process. SEM analysis showed that the solid dispersion morphology consisted of whole and collapsed spheres with smooth surfaces. No crystalline material was observed in the sample.

Figure 13:
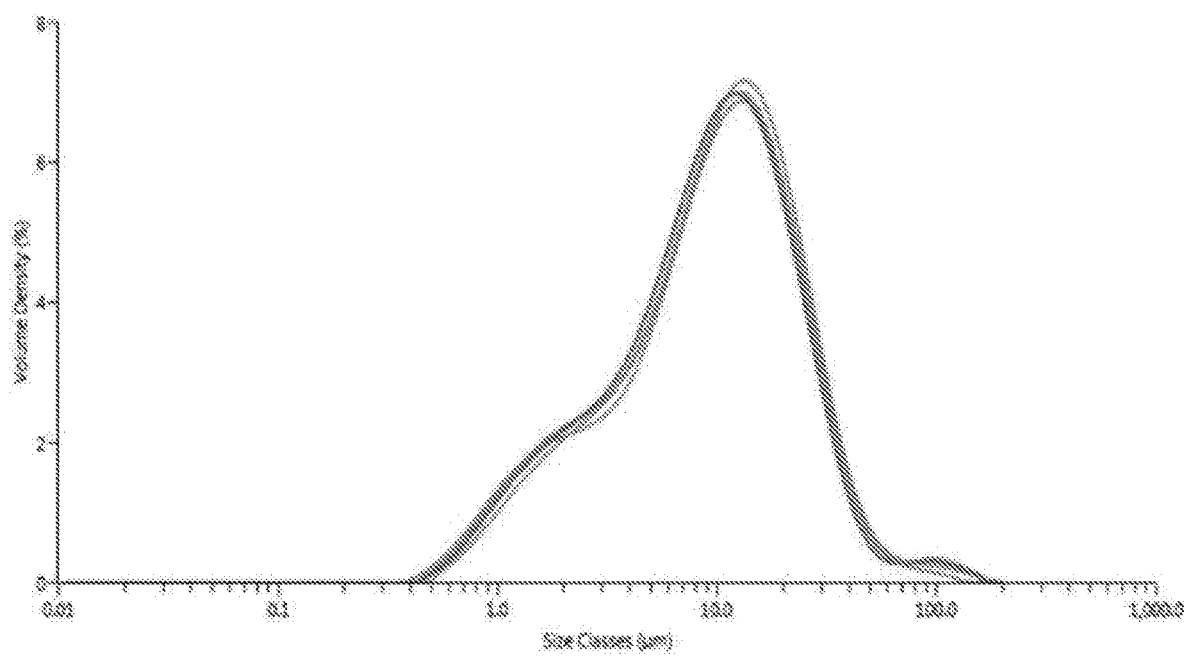
FIG. 13 shows the particle size distribution of a solid dispersion.

As shown in FIG. 13, laser light scattering was performed on the solid dispersion to determine the particle size distribution. A Malvern Aero S dry particle size analyzer was used with a 3 mm hopper height at 0.7 bar pressure with a feed rate of 40%. Samples were analyzed over the course of 10 seconds in triplicate. A refractive index of 1.681 and a density of 0.5 g/mL were used for analysis with a non-spherical algorithm. The sample obscuration was between 0.1 and 15%. The particle size measurement showed that the solid dispersion exhibited a monomodal distribution and determined that the average d$_{10}$ was 1.9 µm, the average d$_{50}$ was 9.8 µm, and the average d$_{90}$ was 26.6 µm. The distribution was truncated at 200 µm due to large, ~1 mm, agglomerates that were not dispersed in the particle size analyzer.

An HPLC assay found to concentration of the compound of Formula (I) to be 25.6% in the solid dispersion. The compound of Formula (I) and solid dispersion showed minimal difference in impurities by HPLC (0.90% and 0.92%, respectively).

Example 10: Tablet Formulations

An 80 gram batch of a solid dispersion containing 1:3 compound of Formula (I): HPMCAS-H was prepared following the general procedures outlined in Examples 3 and 8. Three tablet formulations using this solid dispersion were prepared on a single station press using slug, mill, blend, and compress methodology. The tablets were made at 32.00% solid dispersion load (8% active) to provide 40 mg active tablets pressed with modified capsule tooling (~16.499 mm×8.498 mm) at 500 mg total weight. Tables 16, 17 and 18 summarize the compositions of the three tablet formulations.

TABLE 16

| Component | Mass (mg) | Weight % |
|---|---|---|
| Intragranular | | |
| 25:75 compound of Formula (I):HPMCAS-H | 160 | 32.00 |
| Avicel PH101 (MCC) | 175 | 35.00 |
| Partek M100 (Mannitol) | 75 | 15.00 |
| Ac-di-sol (CCS) | 20 | 4.00 |
| Mg Stearate 2257 | 2.5 | 0.50 |
| Extragranular | | |
| Ac-di-sol (CCS) | 16.25 | 3.25 |
| Partek M100 (Mannitol) | 50 | 10.00 |
| Mg Stearate 2257 | 1.25 | 0.25 |
| Totals | 500 | 100.00 |

TABLE 17

| Component | Mass (mg) | Weight % |
|---|---|---|
| Intragranular | | |
| 25:75 compound of Formula (I):HPMCAS-H | 160 | 32.00 |
| Starch 1500 | 115 | 23.00 |
| Avicel PH101 (MCC) | 50 | 10.00 |
| Partek M100 (Mannitol) | 75 | 15.00 |
| Ac-di-sol (CCS) | 20 | 4.00 |
| Sodium Lauryl Sulfate | 10 | 2.00 |
| PRUV (SSF) | 2.5 | 0.50 |
| Extragranular | | |
| Ac-di-sol (CCS) | 16.25 | 3.25 |
| Partek M100 (Mannitol) | 50 | 10.00 |
| PRUV (SSF) | 1.25 | 0.25 |
| Totals | 500 | 100.00 |

TABLE 18

| Component | Mass (mg) | Weight % |
|---|---|---|
| Intragranular | | |
| 25:75 compound of Formula (I):HPMCAS-H | 160 | 32.00 |
| Avicel PH101 (MCC) | 125 | 25.00 |
| Flo-Lac 90 (Lactose) | 125 | 25.00 |
| Kollidon CL-F | 55 | 11.00 |
| Syloid 244FP | 2.5 | 0.50 |
| Mg Stearate 2257 | 2.5 | 0.50 |
| Extragranular | | |
| Kollidon CL-F | 28.75 | 5.57 |
| Mg Stearate 2257 | 1.25 | 0.25 |
| Totals | 500 | 100.00 |

Each formulation was first compressed to a target solid fraction (~0.7) of half-inch flat slugs. The slugs were milled through a 30-mesh screen. The extragranular excipients were added and the resulting mixture was compressed into tablets. Approximately 90 MPa of pressure was used to achieve a target hardness of 15 kilopond (KP) for the formulations of Tables 16 and 18. A similar hardness was achieved for the formulation of Table 17 using approximately 150 MPa of compression force. Disintegration of tablets prepared from the formulations of Tables 16 and 18 proceeded in less than 1 minute, while the disintegration time of tablets prepared from the formulation of Table 17 was approximately 1.5 minutes.

Additional tablets were prepared at approximately 10 KP hardness and tested for dissolution using USP apparatus II (paddles) in 0.1 N HCl (900 mL) at 37° C. The paddle speed was held at 75 rpm for the first 60 minutes, then increased to 250 rpm for the last 15 minutes of the test. 10 mL samples were drawn at each time point and filtered through a 10 μm polyethylene filter prior to dilution and analysis by HPLC. The dissolution tests showed no differences in the release profiles between the three formulations.

The expected potency of the tablets was confirmed by HPLC. No noticeable difference between formulations was observed in overall total impurities.

The solubility of crystalline compound of Formula (I) as well as 1:3 compound of Formula (I): HPMCAS-H solid dispersion in typical dissolution media at pH 2 and 6.8 was tested. The sink factor was calculated using 900 mL media volume along with the solubility and tablet dose strength and is shown in Table 20.

TABLE 20

| | Compound of Formula (I) | | | Solid Dispersion | | |
|---|---|---|---|---|---|---|
| Media | Solubility (mg/mL) | Sink Factor (10 mg) | Sink Factor (40 mg) | Solubility (mg/mL) | Sink Factor (10 mg) | Sink Factor (40 mg) |
| pH 2.0 (0.01N HCl) | 0.01 | 0.9 | 0.2 | 0.35* | 31.8* | 8.0* |
| pH 2.0 (0.01N HCl) w/0.5% SLS | 0.04 | 3.6 | 0.9 | 0.26 | 23.5 | 5.9 |
| pH 2.0 (0.01N HCl) w/1% SLS | 0.07 | 6.3 | 1.6 | 0.43 | 39.1 | 9.8 |
| pH 2.0 (0.01N HCl) w/0.5% CTAB | 0.06 | 5.4 | 1.4 | 0.27 | 24.2 | 6.1 |
| pH 2.0 (0.01N HCl) w/1% CTAB | 0.1 | 9 | 2.3 | 0.56 | 50.3 | 12.6 |
| pH 2.0 (0.01N HCl) w/0.5% Tween 80 | 0.02 | 1.8 | 0.5 | 0.25 | 22.3 | 5.6 |
| pH 2.0 (0.01N HCl) w/1% Tween 80 | 0.02 | 1.8 | 0.5 | 0.3 | 26.9 | 6.7 |
| pH 6.8 (50 mM $NaH_2PO_4$) | 0.01 | 0.9 | 0.2 | 0.55 | 49.4 | 12.3 |
| pH 6.8 (50 mM $NaH_2PO_4$) w/0.5% SLS | 0.04 | 3.6 | 0.9 | 0.58 | 52 | 13 |
| pH 6.8 (50 mM $NaH_2PO_4$) w/1% SLS | 0.07 | 6.3 | 1.6 | 0.93 | 83.4 | 20.9 |
| pH 6.8 (50 mM $NaH_2PO_4$) w/0.5% CTAB | 0.07 | 6.3 | 1.6 | 0.46 | 41 | 10.3 |
| pH 6.8 (50 mM $NaH_2PO_4$) w/1% CTAB | 0.11 | 9.9 | 2.5 | 0.68 | 60.8 | 15.2 |
| pH 6.8 (50 mM $NaH_2PO_4$) w/0.5% Tween 80 | 0.02 | 1.8 | 0.5 | 0.79 | 71 | 17.8 |
| pH 6.8 (50 mM $NaH_2PO_4$) w/1% Tween 80 | 0.02 | 1.8 | 0.5 | 0.85 | 76.7 | 19.2 |

*potential outliers

Example 11: Tablet Preparation and Characterization

Additional tablets were prepared using the formulations described in Tables 16 and 18 to evaluate their stability, pharmacokinetics (PK), and dissolution in optimized media. The general preparation method described in Example 10 was followed. The compressed tablets exhibited a white appearance. A granule solid fraction of 0.7 and target tablet hardness of 14 KP (1.61 MPa tensile strength) were used. The potency and total impurities of the tablets were assessed by HPLC after compression (Table 19).

TABLE 19

| RRT | Potency | Total Impurities |
|---|---|---|
| Compound of Formula (I) | — | 1.73% |
| Tablet 1 (Table 16 Formulation) | 99.2% | 1.46% |
| Tablet 3 (Table 18 Formulation) | 100.0 | 1.42% |

The pharmacokinetics of the compound of Formula (I) in the two different tablet formulations, Tablet Formulation 1 (Table 16) and Tablet Formulation 3 (Table 18), were evaluated (Table 21). Each formulation was administered to a group of fasted male dogs (n=4/group) (i.e., each dog received a single oral dose containing 40 mg of the compound of Formula (I)). Blood samples were collected at specified time intervals after administration for analysis of plasma concentrations of the compound of Formula (I) over time. For comparison purposes, the pharmacokinetics of Tablet Formulations 1 and 3 were compared with the pharmacokinetics of the solid dispersion (1:3 compound of Formula (I): HPMCAS-H) dosed as a suspension.

TABLE 21

| | Tablet Formulation 1 | Tablet Formulation 3 | Suspension of Solid Dispersion |
|---|---|---|---|
| Dose (mg/kg) | 3.80 | 3.91 | 5 |
| n | 4 | 4 | 4 |
| $AUC_{0-t}$ (μg*hr/mL) | 41.0 | 34.5 | 47.8 |
| $AUC_{0-t}$/Dose | 10.8 | 8.9 | 9.56 |
| $AUC_{0-inf}$ (μg*hr/mL) | 51.0 | 47.7 | 54.3 |
| AUC % Extrap obs | 19.7 | 27.5 | 11.8 |
| $t_{1/2}$ (hr) | 22.6 | 28.3 | 16.5 |
| $t_{max}$ (hr) | 0.7 | 1.1 | 1.8 |

TABLE 21-continued

| | Tablet Formulation 1 | Tablet Formulation 3 | Suspension of Solid Dispersion |
|---|---|---|---|
| $C_{max}$ (µg/mL) | 3.51 | 2.48 | 3.8 |
| $C_{max}$/Dose | 0.92 | 0.93 | 0.76 |

Mean PK parameter estimates are shown in Table 21. The $AUC_{0-t}$ (area under the plasma concentration curve from time equals zero to the last time point collected) of the compound of Formula (I) was used for comparison across groups. Dose normalized mean $AUC_{0-t}$ values were similar to the 1:3 compound of Formula (I): HPMCAS-H suspension formulation (within 20%), at 10.8±3.2 and 8.9±1.4 (µg*hr/mL)/(mg/kg) for Tablet Formulation 1 and 3, respectively. The dose normalized mean $C_{max}$ in plasma values were found to be similar between the two tablet formulations and slightly higher than the suspension formulation. The observed $t_{max}$ values suggested that Tablet Formulation 1 was more quickly absorbed than Tablet Formulation 3.

Tablet Formulations 1 and 3 were placed in accelerated stability conditions (40° C./75% RH), open, and tested for chemical purity and potency at 2 and 4 weeks. Under the accelerated conditions, a decrease in tablet potency from 99.3% to 96.7% was observed while the total impurities increased from 1.24% at time zero to 2.02% after 4 weeks for Tablet Formulation 1. For Tablet Formulation 3, a decrease in tablet potency from 100.1% to 96.2% was observed while the total impurities increased from 1.25% at time zero to 1.77% after 4 weeks.

Example 12: Tablet Formulation, Preparation and Characterization

Tablet Formulation 1, 40 mg active strength, was previously prepared at 0.70 solid fraction with a tablet hardness of 14.1 KP, 1.61 MPa tensile strength (see Examples 10 and 11). This tablet showed a 33 second disintegration time. Additional tablets were prepared with a reduced solid fraction (granules) of 0.6 to allow for additional tablet compressibility. The granules were then compressed at a range of 11.6 to 39.7 KP tablet hardness (1.2-4.7 MPa tensile strength) and the disintegration measured. The disintegration time for these tablets was approximately 30 seconds. The formulation was then modified by removing all extragranular ac-di-sol and mannitol, which were replaced with MCC. The tablets were then compressed to 20.7 KP hardness (2.1 MPa tensile strength) and the disintegration was found to be 27 seconds. The intragranular blend alone was also compressed to 17.9 KP (2.1 MPa tensile strength). The disintegration time for the intragranular blend alone was found to be 26 seconds.

Since the small changes to the formulation did not work and the compression of the intragranular blend alone showed very fast disintegration, attention turned to investigate the impact of changing the grade of MCC from PH101 to PH105 on the disintegration time. This change would more closely match the particle size of the solid dispersion to the main compression aid, MCC, and thus provide more intimate contact with particles allowing for increased binding during roller compaction.

Next, 40 mg active tablets in which PH101 grade MCC of Tablet Formulation 1 was replaced with PH105 grade MCC were compressed (from granules with a solid fraction of 0.59) to 27 KP hardness. The resulting tablets were found to show 1:40 minute disintegration time and 0.03% friability.

With the increased disintegration time, 10 mg active tablets were also compressed and were found to show 10 KP hardness and 2:21 minute disintegration time.

A common blend of Tablet Formulation 4, having the composition provided in Table 22, was prepared, then 10 mg active and 40 mg active tablets were compressed. The tooling selected for compression was standard concave round 0.25" for the 10 mg and 0.2750"×0.5500" modified oval for the 40 mg tablets. The common blend was prepared on approximately 1.25 kg scale using 480 g of solid dispersion. From the common blend, portions were divided for compression of both 10 and 40 mg tablets. The composition of the 10 and 40 mg active tablet formulations is shown in Table 22. The composition of a coated 40 mg active tablet formulation is shown in Table 23.

TABLE 22

| Component | Weight % | 10 mg Active Tablet (mg) | 40 mg Active Tablet (mg) |
|---|---|---|---|
| Intragranular | | | |
| 25:75 compound of Formula(1):HPMCAS-H | 32.00 | 40 | 160 |
| Avicel PH105 (MCC) | 35.00 | 43.75 | 175 |
| Partek M100 (Mannitol) | 17.00 | 21.25 | 85 |
| Ac-di-sol (CCS) | 2.00 | 2.5 | 10 |
| Mg Stearate 2257 | 0.50 | 0.625 | 2.5 |
| Extragranular | | | |
| Ac-di-sol (CCS) | 1.00 | 1.25 | 5 |
| Partek M100 (Mannitol) | 12.25 | 15.3125 | 61.25 |
| Mg Stearate 2257 | 0.25 | 0.3125 | 1.25 |
| Totals | 100.00 | 125 | 500 |

TABLE 23

| Component | Weight % | 40 mg Active Tablet (mg) |
|---|---|---|
| Intragranular | | |
| Compound of Formula (I) | 8.00 | 40.00 |
| HPMCAS-H | 24.00 | 120.00 |
| Avicel PH105 (MCC) | 35.00 | 175.00 |
| Partek M100 (Mannitol) | 17.00 | 85.00 |
| Ac-di-sol (CCS) | 2.00 | 10.00 |
| Mg Stearate 2257 | 0.50 | 2.50 |
| Extragranular | | |
| Ac-di-sol (CCS) | 1.00 | 5.00 |
| Partek M100 (Mannitol) | 12.00 | 60.00 |
| Mg Stearate 2257 | 0.25 | 1.25 |
| CabOSil M5P ($SiO_2$) | 0.25 | 1.25 |
| Totals | 100.00 | 500.00 |
| Coating | | |
| OpaDry II Blue | 3.00 | 15.00 |
| Coated Tablet Totals | 103.00 | 515.00 |

Figure 14:
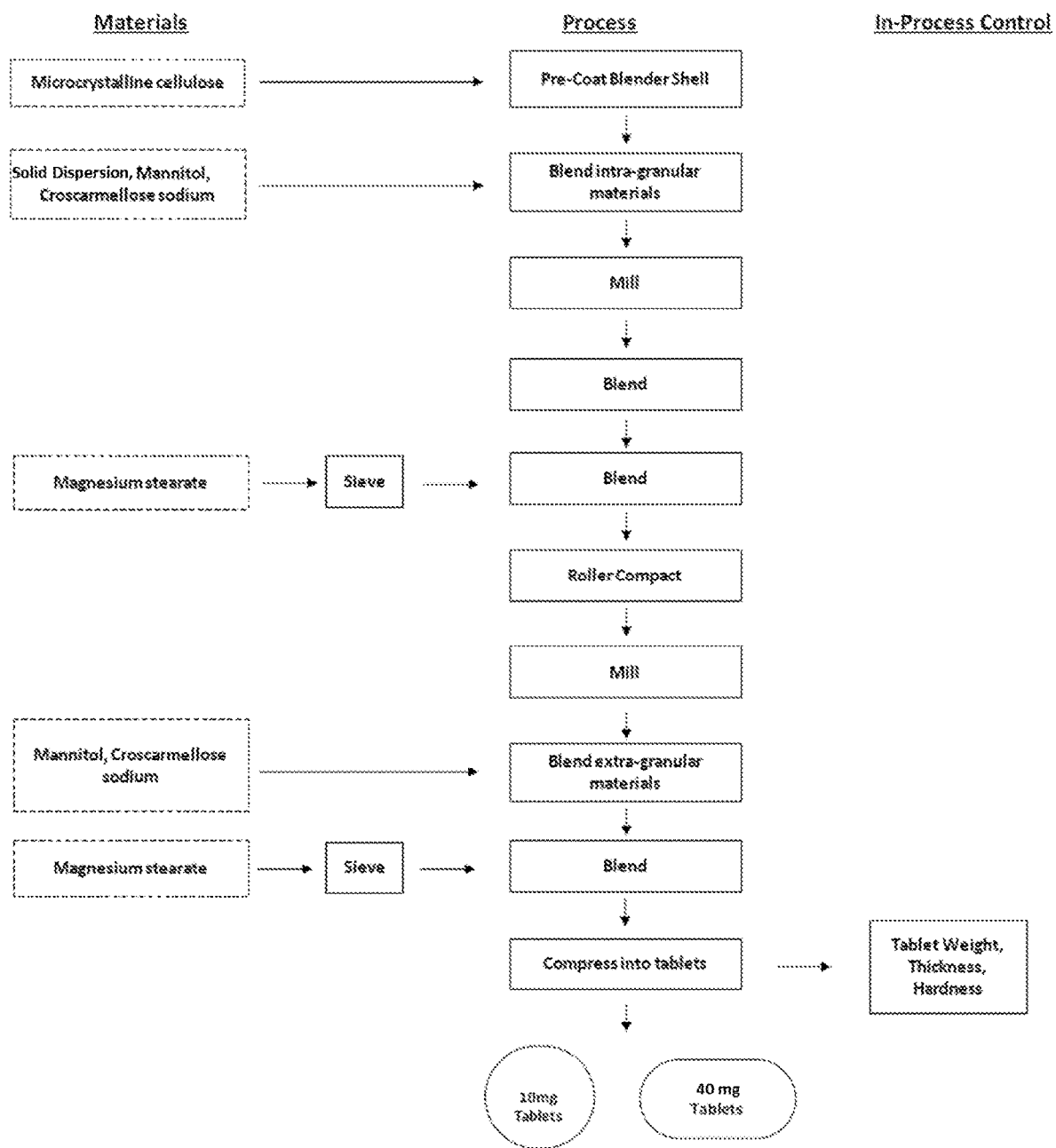
FIG. 14 depicts a process flow chart for preparing a solid dosage form.

The main pieces of equipment used for granulation and tablet preparation were a bin blender with 5 L shell, 40 mesh sieve, Quadro Comil U5 mill, Vector TFC Lab-Micro roller compactor, and a Piccola-B rotary tablet press. Briefly, the granulation and tablet preparation process comprises blending, de-lumping, and roller compacting the intragranular components, blending and de-lumping the extragranular components, and compressing both 10 and 40 mg active tablets. A process flow chart is shown in FIG. 14.

In greater detail, the manufacturing process comprises the following steps: (1) the blender shell was pre-coated with microcrystalline cellulose (1 min at 20 rpm); (2) the intra-granular ingredients were mixed in the coated blender (5 min at 20 rpm); (3) the intra-granular ingredients were milled (Screen 032R, 4000 rpm); (4) the intra-granular ingredients were mixed in a blender (15 min at 20 rpm); (5) 40 mesh sieved magnesium stearate was added to the blender and mixed (4 min at 20 rpm); (6) the mixture was granulated using a roller compactor (Screw Speed 40 rpm, Roll Speed 3 rpm, Pressure 10 mPA); (7) the dry granulated material was passed through a mill (Screen 050G, 2000 rpm); (8) the milled granules were transferred into a blender, and the extra-granular ingredients, except for magnesium stearate, were added and mixed (10 min at 20 rpm); (9) the mixture was lubricated by adding 40 mesh sieved magnesium stearate, then mixed (4 min at 20 rpm); (10) tablets (10 mg and 40 mg strength) were compressed using a tablet press with appropriate tooling (the weight, thickness and hardness were tested during the compression process).

The common blend was prepared on 1.25 kg scale using roller compaction to target a ribbon bulk density of approximately 0.8 g/mL (~0.6 solid fraction). Processing was completed at room temperature (approximately 25.2° C.) at a relative humidity of 26%. Bulk and tapped density (Table 24) were measured in addition to the particle size of the granules, post milling.

TABLE 24

| Parameter | Value |
|---|---|
| Intragranular Blend Bulk Density (g/mL) | 0.309 |
| Intragranular Blend Tap Density (g/mL) | 0.571 |
| Intragranular Blend Hausner Ratio | 1.848 |
| Granule Bulk Density (g/mL) | 0.544 |
| Granule Tap Density (g/mL) | 0.795 |
| Granule Hausner Ratio | 1.461 |
| Final Blend Bulk Density (g/mL) | 0.577 |
| Final Blend Tap Density (g/mL) | 0.826 |
| Final Blend Hausner Ratio | 1.432 |

The intra-granular blend showed the lowest bulk density and highest Hausner ratio. After granulation, the bulk density improved to 0.5 g/mL and the Hausner ratio decreased, suggesting improved flow. Addition of the extragranular excipients did not change the bulk properties of the granules, but did slightly improve the flowability as indicated by a lower Hausner ratio.

The particle size distribution showed that most granules (48.7%) were retained between 250-595 μm sieves, with the bulk of the remaining material collected in the pan. 31% fines (particles less than 74 μm) were observed. The overall yield was 96.1% with a total of 1.2 kg final blend collected.

The granules were split between the 10 and 40 mg tablet compression. The 40 mg active tablets were made using 949.95 g of the granules. The tooling description, as well as the number of stations, target fill weight and tablet hardness, are shown in Table 25.

TABLE 25

| Tablet Parameters | Value (40 mg tablet) | Value (10 mg tablet) |
|---|---|---|
| Tooling Size (in) Modified Oval | 0.2750 × 0.550 | 0.2500 |
| Cup Depth (mm) | 1.016 | 0.8282 |
| Cup Area (mm²) | 91.85 | 33.877 |
| No. of Stations | 2 | 5 |

TABLE 25-continued

| Tablet Parameters | Value (40 mg tablet) | Value (10 mg tablet) |
|---|---|---|
| Target Fill Wt. (mg) | 500 ± 25 | 125 ± 6 |
| Target Hardness (KP) | 20 ± 2 | 10 ± 2 |

A Piccola press was run at 20 rpm with a paddle speed of 5 rpm. The compression force was dialed into 15 kN with a precompression force of 480-600 N. The ejection force during the run was found to be 181 N. A total of 1736 tablets at 91.4% yield were recovered during the compression operation. In-process characterization of the tablets showed a hardness range from 16.9-22.8 KP, with most of the tablets being approximately 20 KP. Tablet thickness was approximately 5.7-5.8 mm and the weight was centered on 500 mg. Disintegration testing showed an average of 1:37 and friability was 0.14%.

The remaining granules, approximately 257.05 g, were used for the 10 mg tablet compression. A Piccola press was run at 20 rpm with a paddle speed of 4 rpm. The compression force was dialed in to 7.5 kN with a precompression force of 280 N. The ejection force during the run was found to be 80-89 N. A total of 1561 tablets at 75.9% yield were recovered during the compression operation. In-process characterization of the tablets showed a hardness range from 8.8-10.5 KP, with most of the tablets being approximately 10 KP. Tablet thickness was approximately 3.9 mm and the weight was centered on 126 mg. Disintegration testing showed an average of 2:04 and friability was 0.01%.

The tablets were characterized for appearance, identification by HPLC, assay and impurities, content uniformity, water content, and dissolution. A summary of the test results is provided in Table 26.

TABLE 26

| Test | 10 mg Tablet Result | 40 mg Tablet Result |
|---|---|---|
| Appearance | White, round, biconvex tablets | White, oval, biconvex tablets |
| ID (HPLC) | 100% | 100% |
| Potency (HPLC) | 100.3% | 99.0% |
| Total Impurities (HPLC) | 1.29% | 1.23% |
| Content Uniformity (HPLC) | Meets USP <905> Criteria, AV = 5.57 | Meets USP <905> Criteria, AV = 6.90 |
| Water Content (KF) | 2.06% | 1.96% |

Figure 15:
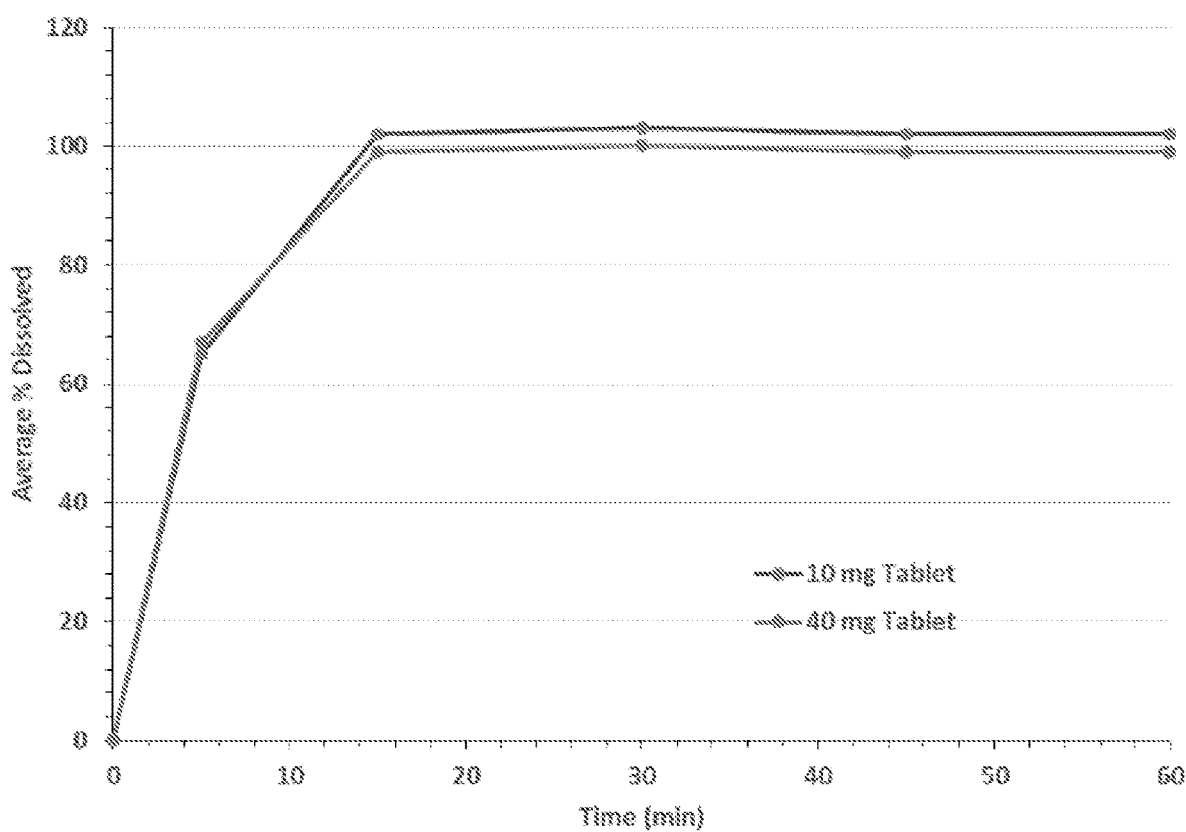
FIG. 15 shows the dissolution profile of 10 and 40 mg tablets.

The appearance of the tablets was white with no observed speckles or mottling, and the potency by HPLC was nearly 100%. Total impurities were similar to that in the solid dispersion and content uniformity passed USP criteria. Water content was similar between the two tablets. Dissolution analysis was performed in 0.01N HCl (pH 2) with 0.5% SLS media (900 mL) at 37° C. with a paddle speed of 75 rpm. Data collection was completed at 5, 15, 30, 45 and 60 minutes. A 10 mL sample was drawn at each time point and filtered through a 10 μm polyethylene filter prior to dilution and analysis by HPLC. FIG. 15 shows the combined dissolution plot for the 10 and 40 mg tablets.

Complete dissolution was observed in 15 minutes for both tablet strengths. The standard deviation for all time points was between 1-3% and the RSD also ranged from 1-3%, indicating the dissolution was very similar between units. The dissolution profile meets USP/FDA criteria for immediate release dosage forms for poorly water soluble drugs where 85% dissolution is achieved after 30 and/or 45 minutes.

The bulk tablets were packaged in double LDPE bags with $SiO_2$ desiccant between the bags, then placed in an HDPE drum.

Example 13: Pharmacokinetics of Tablets

The pharmacokinetics of the 40 mg tablets described in Example 12 were evaluated in both fasted and fed dogs. The formulation was administered to a group of fasted male dogs (n=4/group) and fed male dogs (n=4/group), wherein each dog received a single oral dose of 40 mg. Blood samples were collected at specified time intervals after dose administration for analysis of plasma concentrations of the compound of Formula (I) over time. Mean PK parameter estimates are shown in Table 27.

TABLE 27

|  | Fed | Fasted |
| --- | --- | --- |
| Dose (mg/kg) | 3.5 | 3.7 |
| n | 4 | 4 |
| $AUC_{0-t}$ (µg*hr/mL) | 29.9 | 35.0 |
| $AUC_{0-t}$/Dose | 8.6 | 9.4 |
| AUC % Extrap obs | 38.0 | 40.3 |
| $t_{1/2}$ (hr) | 21.0 | 17.5 |
| $t_{max}$ (hr) | 3.0 | 1.0 |
| $C_{max}$ (µg/mL) | 1.7 | 2.9 |
| $C_{max}$/Dose | 0.5 | 0.8 |

Dose normalized mean $AUC_{0-t}$ values were similar between the groups (within 20%) at 8.6 and 9.4 (µg*hr/mL)/(mg/kg) for fed and fasted tablet evaluation, respectively. The inter-animal exposure variability with the fed state was less than when the tablet was administered on a fasted stomach. The dose normalized mean $C_{max}$ in plasma was found to be slightly higher for the fasted stomach. The observed $t_{max}$ values suggested that the tablet formulation was more quickly absorbed in the fasted state, with the fasted state showing a quick $t_{max}$ and slightly higher $C_{max}$. The $AUC_{0-t}$ values were similar, indicating that no substantial food effect is likely for the tablet formulation.

Example 14: Stability of Tablets

The stability of both the 10 and 40 mg active tablets described in Example 12 was evaluated. The 10 mg tablets were stored in 30 cc HDPE bottles (30 tablets per bottle) with 0.5 g $SiO_2$ desiccant and 9 gram pure coil polyester. The 40 mg tablets were stored in 60 cc HDPE bottles (30 tablets per bottle) with 0.5 g $SiO_2$ desiccant and 9 gram pure coil polyester. All bottles were sealed with a foil heat-induction seal. Bottles were placed in stability chambers at 2-8° C., 25° C./60% RH, and 40° C./75% RH for six months. A brief summary of the results for the 10 and 40 mg tablets at the 6-month time point is provided in Table 28 and Table 29, respectively.

TABLE 28

| | 10 mg Tablet | | | |
| --- | --- | --- | --- | --- |
| Test | t = 0 (Release) | t = 6-months 2-8° C. | t = 6-months 25° C./ 60% RH | t = 6-months 40° C./ 75% RH |
| Appearance | White, round biconvex tablets | White, round biconvex tablets | White, round biconvex tablets | White, round biconvex tablets |
| Assay (HPLC) | 100.3% | 100.1% | 101.8% | 99.6% |
| Total Impurities (HPLC) | 1.29% | 1.50% | 1.49% | 1.54% |
| Water Content (KF) | 2.06% | 1.53% | 1.65% | 2.08% |
| Dissolution (HPLC) (% Dissolved at 30 min) | 103% | 97% | 97% | 97% |

TABLE 29

| | 40 mg Tablet | | | |
| --- | --- | --- | --- | --- |
| Test | t = 0 (Release) | t = 6-months 2-8° C. | t = 6-months 25° C./ 60% RH | t = 6-months 40° C./ 75% RH |
| Appearance | White, oval, biconvex tablets | White, oval, biconvex tablets | White, oval, biconvex tablets | White, oval, biconvex tablets |
| Assay (HPLC) | 99.0% | 101.0% | 100.7% | 100.7% |
| Total Impurities (HPLC) | 1.23% | 1.53% | 1.51% | 1.52% |
| Water Content (KF) | 1.96% | 1.69% | 1.72% | 2.10% |
| Dissolution (HPLC) (% Dissolved at 30 min) | 100% | 96% | 94% | 92% |

No significant differences in the physical or chemical attributes of the tablets were observed over the course of six months, even under accelerated storage conditions.

Example 15: HIF-2α Scintillation Proximity Assay (SPA)

The total assay volume was about 100 µL in the following configuration: 2 µL compound in 100% DMSO, 88 µL buffer with protein and probe and 10 µL of SPA beads. The compound was diluted in a master plate consisting of a 10-point dose response with a 3-fold compound dilution from 100 µM to 5 nM. Assays were run on a 96-well plate in which one column, designated as the high signal control, contained DMSO with no compound and another column, designated as the low signal control, contained no protein. Prior to plating out of compound, a buffer solution, consisting of 25 mM TRIS pH 7.5 (Sigma), 150 mM NaCl (Sigma), 15% Glycerol (Sigma), 0.15% BSA (Sigma), 0.001% Tween-20 (Sigma), 150 nM N-(3-Chlorophenyl-4,6-$t_2$)-4-nitrobenzo[c][1,2,5]oxadiazol-5-amine and 100 nM HIF-2a HIS TAG-PASB Domain, was made and allowed to equilibrate for 30 minutes. Compounds that were to be tested were then plated in to a 96-well white clear bottom Isoplate-96 SPA plate (Perkin Elmer). To the compounds was added 88 µL of the buffer solution, then the plate covered with a plastic cover and aluminum foil, placed onto a shaker and equilibrated for 1 hour. After equilibration, 10 µL of a 2 mg/mL solution of YSi Cu His tagged SPA beads (Perkin Elmer) were then added to each well of the plate, covered and equilibrated for another 2 hours. The plates were then removed from the shaker, placed into a 1450 LSC and luminescence counter MicroBeta Trilux (Perkin Elmer) to measure the extent of probe displacement. The percent inhibition was determined and $IC_{50}$ values were calculated using the Dotmatics system based on the following equation: % inhibition=[(high control−sample)/(high control−low control)]×100. The compound of Formula (I) was found to have an $IC_{50}$ of less than 50 nM in the SPA assay.

Example 16: VEGF ELISA Assay

About 7500 786-O cells in 180 μL of growth medium were seeded into each well of a 96-well, white, clear bottom plate (07-200-566, Fisher Scientific) on day one. Four hours later, serial dilutions of 10× compound stocks were made in growth medium from 500× DMSO stocks, and 20 μL of those 10× stocks were added to each well to make final concentrations as follows (μM): 20, 6.67, 2.22, 0.74, 0.25, 0.082, 0.027, 0.009, 0.003, 0.001, and 0. Each concentration was plated in duplicate. About 20 hours later, medium was removed by suction and each well was supplied with 180 μL of growth medium. About 20 μl freshly-made 10× compound stocks were added to each well. About 24 hours later, cell culture medium was removed and the VEGF concentration determined using an ELISA kit purchased from R&D systems, following the manufacturer's suggested method. The $EC_{50}$ was calculated by GraphPad Prism using the dose-response-inhibition (four parameter) equation. The cell-seeded plate was then subjected to CellTiter-Glo luminescence cell viability assay (Promega) by adding 50 μL of Celltiter Glo reagent into each well and shaking the plate for 8 minutes at 550 rpm (Thermomixer R, Eppendorf) then the luminescence signal immediately read in a plate reader (3 second delay, 0.5 second/well integration time, Synergy 2 multi Detection Microplate reader). The compound of Formula (I) was found to have an $EC_{50}$ of less than 50 nM in the VEGF ELISA assay.

Example 17: Luciferase Assay

786-O-Hif-Luc single clone cells were obtained by infecting 786-0 cells (ATCC® CRL-1932™) with commercial lentivirus that delivers a luciferase gene driven by multiple HIF responsive elements (Cignal Lenti HIF Reporter (luc): CLS-007L, Qiagen) at Multiplicity of Infection (MOI) of 25 for 24 hours. The cells were replenished with fresh medium (Dulbecco's Modified Eagle's Medium (DMEM, D5796, Sigma) supplemented with 10% FBS (F6178, Sigma), 100 units penicillin and 100 μg streptomycin/mL (P4333, Sigma)) for another 24 hours. A pool of infected cells were then selected against 2 μg/mL of puromycin (P8833, Sigma) for 10 days followed by limited dilution to select single clones. The clones were tested for their response to HIF-2 inhibitors and the ones that showed the biggest dynamic range (786-O-Hif-Luc) were expanded and used for the luciferase assay. For the luciferase assay, about 7500 786-O-Hif-Luc cells in 90 μL growth medium were seeded into each well of a 96-well white opaque plate (08-771-26, Fisher scientific) a day before treatment.

On treatment day, serial dilutions of 10× compound stocks were made in growth medium from 500× DMSO stocks, and 10 μL of the 10× stocks were added to each well to make final concentrations as follows (μM): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. $EC_{50}$ were calculated using Dotmatics software. The compound of Formula (I) was found to have an $EC_{50}$ of less than 50 nM in the luciferase assay.

Example 18: Spray Dried Dispersion (SDD) Scale Up Process Parameter Screening

A solution of the compound of Formula (I): HPMCAS-H in acetone was prepared in a 50 L tank with top-mounted agitation and by mixing all ingredients until visibly clear of solids. The solution compositions and mixing time are as follows:

| Ingredients | Quantity (g) | Percent in Solution (wt %) | Percent in SDD (wt %) | Mix Time (min) |
|---|---|---|---|---|
| Acetone | 29400 | 88.0 | 0 | NA |
| Compound of Formula (I) | 1000.7 | 3.0 | 25.0 | 24 |
| HPMCAS-HG | 2996 | 9.0 | 75.0 | 38 |
| Total | 33400 | 100.0 | 100 | 62 |

Preparation of Spray Dried Dispersion (SDD) of the compound of Formula (I) was examined by investigating various processing parameters and the resulting bulk properties from the above-prepared solution. The following processing ranges were explored on an open-loop spray dryer with 200 kg/hr drying gas capacity:

Outlet temperature: 35-46° C.

Solution feed rate: 340-455 g/min

Calculated outlet relative saturation: 7-11%

As a function of the various thermodynamic conditions and nozzle sizes used, the resulting bulk property ranges were observed:

Particle D (v 0.5): 33-67 μm

Bulk Density: 0.16-0.20 g/mL

Demonstration Batch

The lead condition prior to the demonstration batch was manufactured with a L:G ratio of 0.121 and outlet temperature of 42° C. These conditions resulted in SDD with acceptable stability, performance, and yield. The following spray drying conditions were elected for the manufacture of 25% compound of Formula (I): HPMCAS-H SDD.

| Process Stage | | System Gas Flow (g/min) | Dryer Inlet Temp (° C.) | Dryer Outlet Temp (° C.) | Solution Pressure | Solution Feed Rate (g/min) |
|---|---|---|---|---|---|---|
| SYSTEMS TEST | Target | 3300 | 105 | 40 | 850 | 330 |
| | Range | 3100-3465 | 75-135 | 35-45 | 800-900 | 315-345 |
| PREHEAT | Target | 3300 | 105 | | | |
| | Range | 3100-3465 | 75-135 | | | |
| WARM-UP | Target | 3300 | 105 | 40 | 850 | 330 |
| | Range | 3100-3465 | 75-135 | 35-45 | 750-950 | 300-360 |
| SOLUTION | Target | 3300 | 110 | 40 | 825 | 400 |
| | Range | 3100-3465 | 80-140 | 35-45 | 725-925 | 380-420 |
| SHUT DOWN | Target | 3300 | 105 | 40 | 850 | 330 |
| | Range | 3100-3465 | 75-135 | 35-45 | 750-950 | 300-360 |

Based on the drying curve generated for the demonstration batch, the following secondary drying conditions using a convection tray dryer were elected

| Temperature (° C.) | Relative Humidity (%) | Time at Condition (hr) | Bed Depth |
|---|---|---|---|
| 40° C. ± 5° C. | 15% ± 10% | ≥10 | ≤2.5 cm |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical solid dosage form for oral delivery of a compound of Formula (I),

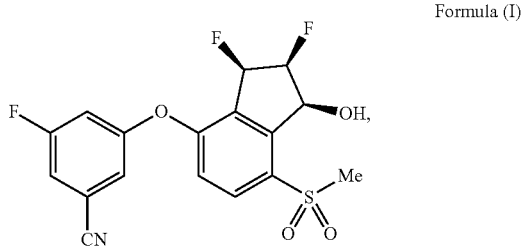 [SMILES: CS(=O)(=O)c1ccc(Oc2cc(F)cc(C#N)c2)c2c1[C@H](O)[C@H](F)[C@@H]2F]

Formula (I)

wherein the solid dosage form comprises
  a solid dispersion comprising the compound of Formula (I), a pharmaceutically acceptable polymer selected from the group consisting of Hypromellose acetate succinate (HPMCAS), cellulose acetate phthalate (CAP), and polyethylene glycol vinyl acetate vinylcaprolactam,
  one or more pharmaceutically acceptable excipients comprising a binder, a filler, a disintegrant and a lubricant, wherein the binder is a microcrystalline cellulose, and
  the solid dosage form is a capsule or a tablet.

2. The solid dosage form of claim 1, wherein the solid dosage form is a tablet.

3. The solid dosage form of claim 1, wherein the one or more pharmaceutically acceptable excipients further comprise a glidant.

4. The solid dosage form of claim 1, wherein the solid dispersion is present in an amount from 15% to 50% by weight of the solid dosage form.

5. The solid dosage form of claim 1, wherein the pharmaceutically acceptable polymer is HPMCAS.

6. The solid dosage form of claim 1, wherein the pharmaceutically acceptable polymer is present in an amount from 15% to 35% by weight of the solid dosage form.

7. The solid dosage form of claim 1, wherein the compound of Formula (I) is present in an amount from 1% to 15% by weight of the solid dosage form.

8. The solid dosage form of claim 1, comprising 5 mg to 100 mg of the compound of Formula (I).

9. The solid dosage form of claim 1, comprising about 10 mg of the compound of Formula (I).

10. The solid dosage form of claim 1, comprising about 40 mg of the compound of Formula (I).

11. The pharmaceutical solid dosage form of claim 1, wherein the one or more excipients further comprise mannitol, croscarmellose sodium and magnesium stearate.

12. The pharmaceutical solid dosage form of claim 1, wherein the pharmaceutical solid dosage form comprises, by weight of the solid dosage form:
  (a) 15% to 50% of a solid dispersion comprising the compound of Formula (I) and HMPCAS;
  (b) 20% to 50% of the microcrystalline cellulose;
  (c) 20% to 40% of a mannitol;
  (d) 1.0% to 5.0% of a croscarmellose sodium; and
  (e) 0.25% to 1.25% of magnesium stearate.

* * * * *